(12) United States Patent
Ma et al.

(10) Patent No.: US 8,183,381 B2
(45) Date of Patent: May 22, 2012

(54) N-LINKED HETEROCYCLIC RECEPTOR AGONISTS FOR THE TREATMENT OF DIABETES AND METABOLIC DISORDERS

(75) Inventors: Jingyuan Ma, Sunnyvale, CA (US); Christopher J. Rabbat, San Jose, CA (US); Jiangao Song, Sunnyvale, CA (US); Xin Chen, San Ramon, CA (US); Imad Nashashibi, San Jose, CA (US); Zuchun Zhao, Pleasanton, CA (US); Aaron Novack, San Jose, CA (US); Dong Fang Shi, Fremont, CA (US); Peng Cheng, Tianjin (CN); Yan Zhu, Foster City, CA (US); Alison Murphy, Milpitas, CA (US)

(73) Assignee: Metabolex Inc., Hayward, CA (US)

( * ) Notice: Subject to any disclaimer, the term of this patent is extended or adjusted under 35 U.S.C. 154(b) by 755 days.

(21) Appl. No.: 12/171,209

(22) Filed: Jul. 10, 2008

(65) Prior Publication Data

US 2009/0137590 A1    May 28, 2009

Related U.S. Application Data

(60) Provisional application No. 60/950,859, filed on Jul. 19, 2007.

(51) Int. Cl.
  *C07D 401/00* (2006.01)
(52) U.S. Cl. .................................... 546/275.4
(58) Field of Classification Search .............. 546/275.4
   See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,778,443 A * | 12/1973 | Arya | 546/275.4 |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,673,564 A | 6/1987 | Kawata et al. | |
| 4,894,235 A | 1/1990 | Kohne et al. | |
| 5,013,556 A | 5/1991 | Woodle et al. | |
| 5,340,591 A | 8/1994 | Nakano et al. | |
| 5,456,923 A | 10/1995 | Nakamichi et al. | |
| 5,707,646 A | 1/1998 | Yajima et al. | |
| 5,817,677 A | 10/1998 | Linz et al. | |
| 5,939,099 A | 8/1999 | Grabowski et al. | |
| 6,221,660 B1 | 4/2001 | Bonini et al. | |
| 6,468,756 B1 | 10/2002 | Bonini et al. | |
| 7,108,991 B2 | 9/2006 | Chen et al. | |
| 7,638,541 B2 * | 12/2009 | Chen et al. | 514/365 |
| 2002/0198223 A1 | 12/2002 | Allerton et al. | |
| 2003/0064990 A1 | 4/2003 | Denton et al. | |
| 2005/0165005 A1 | 7/2005 | Genevois-Borella et al. | |
| 2006/0135501 A1 | 6/2006 | Knox et al. | |
| 2006/0142262 A1 | 6/2006 | Jones et al. | |
| 2006/0155128 A1 | 7/2006 | Jones et al. | |
| 2009/0054475 A1 | 2/2009 | Chen et al. | |
| 2009/0270404 A1 | 10/2009 | Wilson et al. | |
| 2010/0087465 A1 | 4/2010 | Chen et al. | |
| 2010/0130511 A1 | 5/2010 | Chen et al. | |
| 2011/0152270 A1 | 6/2011 | Song et al. | |
| 2011/0160222 A1 | 6/2011 | Chen et al. | |

FOREIGN PATENT DOCUMENTS

| | | |
|---|---|---|
| CL | 2775-2002 | 6/2001 |
| CL | 2899-2000 | 7/2001 |
| CL | 2130-2008 | 1/2009 |
| CL | 2131-2008 | 1/2009 |
| CL | 2093-2008 | 5/2009 |
| CL | 2138-2008 | 10/2009 |
| CL | 2139-2008 | 10/2009 |
| EP | 0901786 | 3/1999 |
| EP | 1092727 A2 | 4/2001 |
| EP | 1129706 A2 | 9/2001 |
| EP | 1176147 A1 | 1/2002 |
| EP | 1422228 A1 | 5/2004 |
| EP | 1133559 B1 | 8/2005 |
| EP | 1584683 B1 | 7/2007 |
| EP | 1813606 A1 | 8/2007 |
| WO | WO 00/50562 A2 | 8/2000 |
| WO | WO 02/098223 A1 | 12/2002 |
| WO | WO 2004/037809 A1 | 5/2004 |
| WO | WO 2004/078413 A1 | 9/2004 |
| WO | WO 2004/113323 A1 | 12/2004 |
| WO | WO 2005/011654 A2 | 2/2005 |
| WO | WO 2005/061489 A1 | 7/2005 |
| WO | WO 2006/054652 A1 | 5/2006 |
| WO | WO 2006/076231 A2 | 7/2006 |
| WO | WO 2006/091428 A2 | 8/2006 |
| WO | WO 2006/124692 A2 | 11/2006 |
| WO | WO 2006/133216 A2 | 12/2006 |
| WO | WO 2007/003960 A1 | 1/2007 |
| WO | WO 2007/003961 A2 | 1/2007 |
| WO | WO 2007/023507 A2 | 3/2007 |

(Continued)

OTHER PUBLICATIONS

Deng et al. "A novel and efficient synthesis of 2,5-substituted 1,2,4-triazol-3-ones" Tetrahedron Letters, vol. 46, No. 46, 2005, pp. 7993-7996, XP005113190. "Report of the Expert Committee on the Diagnosis and Classification of Diabetes Mellitus", Diabetes Care, (1999) vol. 26 (Suppl 1): S5-19.
Ashcroft et al., "ATP-sensitive $K^+$ channels and insulin secretion: their role in health and disease." Diabetologia (1999) 42: 903-919.
Barrett-Conner, "Epidemiology, obesity, and non-insulin-dependent diabetes mellitus." Epidemol Rev (1989) 11: 172-181.
Bell et al., "Diabetes mellitus and genetically programmed defects in β-cell function." Nature (2001) 414: 788-791.
Bicklé, "Meglitinide analogues: a review of clinical data focused on recent trials." Diabetes Metab (2006) 32(2): 113-120.
Brubaker, "The Glucagon-Like Peptides Pleiotropic Regulators of Nutrient Homeostatsis." Ann N Y Acad Sci (2006) 1070: 10-26.
Cantin et al., "PDE-10A inhibitors as insulin secretagogues." Bioorg Med Chem Lett (2007) 17(10): 2869-2873).
Castro et al. "Enhancement of Oral Absorption in Selective 5-HT$_{1D}$ Receptor Agonists: Fluorinated 3-[3-(Piperidin-1-yl)propyl]indoles." J. Med. Chem. (1998) 41: 2667-2670.

(Continued)

Primary Examiner — Kevin E Weddington
(74) Attorney, Agent, or Firm — Foley & Lardner LLP

(57) ABSTRACT

Compounds and methods are provided for the treatment of, inter alia, Type II diabetes and other diseases associated with poor glycemic control.

10 Claims, 2 Drawing Sheets

FOREIGN PATENT DOCUMENTS

| | | |
|---|---|---|
| WO | WO 2007/035355 A2 | 3/2007 |
| WO | WO 2007023507 A2 * | 3/2007 |
| WO | WO 2007/039177 A2 | 4/2007 |
| WO | WO 2007/120702 A2 | 10/2007 |
| WO | WO 2008/008887 A2 | 1/2008 |
| WO | WO 2008/083238 A2 | 7/2008 |
| WO | WO 2008/109702 A1 | 9/2008 |
| WO | WO 2009/010429 | 1/2009 |
| WO | WO 2009/010761 | 1/2009 |
| WO | WO 2009/014637 | 1/2009 |
| WO | WO 2009/016516 | 2/2009 |
| WO | WO 2009/037394 | 3/2009 |
| WO | WO 2010/008739 A2 | 1/2010 |
| WO | WO 2010/029089 | 3/2010 |
| WO | WO 2011/041154 | 4/2011 |

OTHER PUBLICATIONS

Cavaghan et al., "Interactions between insulin resistance and insulin secretion in the development of glucose intolerance." *J Clin Invest* (2000) 106(3): 329-333.

Chiasson et al., "The Efficacy of Acarbose in the Treatment of Patients with Non-Insulin-dependent Diabetes Mellitus: A Multicenter Controlled Clinical Trial." *Ann Intern Med* (1994) 121(12): 928-935.

Choi et al., "Alterations in regulations of energy homeostasis in cyclic nucleotide phosphodiesterase 3B-null mice." *J Clin Invest* (2006) 116(12): 3240-3251.

Coniff et al., "Acarbose: A Review of US Clinical Experience." *Clin Ther* (1997) 19(1): 16-26.

Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." *Am J Med* (1995) 98: 443-451.

Drucker, "The role of gut hormones in glucose homeostasis." *J Clin Invest* (2007) 117(1): 24-32.

Elahi et al., "The insulinotropic actions of glucose-dependent insulinotropic polypeptide (GIP) and glucagon-like peptide-1 (7-37) in normal and diabetic subjects." *Regul Pept* (1994) 51: 63-74.

Farilla et al., "Glucagon-Like Peptide 1 Inhibits Cell Apoptosis and Improves glucose Responsiveness of Freshly Isolated Human Islets." *Endocrinology* (2003) 144(12): 5149-5158.

Farilla et al., "Glucagon-Like Peptide-1 Promotes Islet Cell Growth and Inhibits Apoptosis in Zucher Diabetic Rats." *Endocrinology* (2002) 143(11): 4397-4408.

Filipsson et al., "The Neuropeptide Pituitary Adenylate Cyclase-Activating Polypeptide and Islet Function." *Diabetes* (2001) 50(9): 1959-1969.

Flier, "Insulin Receptors and Insulin Resistance." *Ann Rev Med* (1983) 34: 145-160.

Friedrichsen et al., "Stimulation of pancreatic β-cell replication by incretins involves transcriptional induction of cyclin D1 via multiple signalling pathways." *J Endocrinol* (2006) 188(3): 481-492.

Furman et al., "Modulation of cyclic nucleotides and cyclic nucleotide phosphodiesterases in pancreatic islet β-cells and intestinal L-cells as targets for treating diabetes mellitus." *Curr Opin Investig Drugs* (2006) 7(10): 898-905.

Gilon et al., "Mechanisms and Physiological Significance of the Cholinergic Control of Pancreatic β-Cell Function." *Endocr Rev* (2001) 22(5): 565-604.

Gloyn et al., "Insights into the Structure and Regulation of Glucokinase from a Novel Mutation (V62M), Which Causes Maturity-onset Diabetes of the Young." *J Biol Chem* (2005) 280(14): 14105-14113.

González et al., "Investigational treatments for type 2 diabetes mellitus: exenatide and liraglutide." *Expert Opin Investig Drugs* (2006) 15(8): 887-895.

Gromada et al., "Glucagon-Like Peptide 1(7-36) Amide Stimulates Exocytosis in Human Pancreatic beta-Cells by Both Proximal and Distal Regulatory Steps in Stimulus-Secretion Coupling." *Diabetes* (1998) 47(1): 57-65.

Guertin et al., "Small Molecule Glucokinase Activators as Glucose Lowering Agents: A New Paradigm for Diabetes Therapy." *Curr Med Chem* (2006) 13(15): 1839-1843.

Haffner, "Management of Dyslipidemia in Adults With Diabetes." *Diabetes Care* (1998) 21(1): 160-178.

Han et al., "The Calcium/Calmodulin-dependent Phosphodiesterase PDE1C Down-regulates Glucose-induced Insulin Secretion." *J Biol Chem* (1999) 274(32): 22337-22344.

Hansen, "Towards Selective Kir6.2/SUR1 Potassium Channel Openers, Medicinal Chemistry and Therapeutic Perspectives." *Curr Med Chem* (2006) 13(4): 361-376.

Hansotia et al., "Extrapancreatic incretin receptors modulate glucose homeostasis, body weight, and energy expenditure." *J Clin Invest* (2007) 117(1): 143-152, Epub Dec. 21, 2006.

Härndahl et al., "Important Role of Phosphodiesterase 3B for the Stimulatory Action of cAMP on Pancreatic β-Cell Exocytosis and Release of Insulin." *J Biol Chem* (2002) 277(40): 37446-37455.

Hatakeyama et al., "Rapid glucose sensing by protein kinase A for insulin exocytosis in mouse pancreatic islets." *J Physiol* (2006) 570(Pt 2): 271-282.

Henquin, "Pathways in β-Cell Stiumulus-Secretion Coupling as Taragets fro Therepeutic Insulin Secretagogues." *Diabetes* (2004) 53, Suppl. 3, S48-S58.

Holz, "Perspectives in Diabetes Epac: A New cAMP-Binding Protein in Support of Glucagon-Like Peptide-1 Receptor-Mediated Signal Transduction in the Pancreatic β-Cell." *Diabetes* (2004) 53(1): 5-13.

Hussain et al., "Increased Pancreatic β-Cell Proliferation Mediated by CREB Binding Protein Gene Activation." *Mol Cell Biol* (2006) 26(20): 7747-7759.

Iwamoto et al., "Effect of Combination Therapy of Troglitazone and Sulphonylureas in Patients with Type 2 Diabetes Who Were Poorly Controlled by Sulphonylurea Therapy Alone." *Diabet Med* (1996) 13: 365-370.

Kahn, "The Importance of the β-Cell in the Pathogenesis of Type 2 Diabetes Mellitus." *Am J Med* (2000) 108 Suppl 6a, 2S-8S.

Kahn, "Type 2 Diabetes: When Insulin Secretion Fails to Compensate for Insulin Resistance." *Cell* (1998) 92: 593-596.

Kaplan et al., "Cardiovascular diseases" in Health and Human Behavior, pp. 206-242 (McGraw-Hill, New York 1993).

Kashima et al., "Critical Role of cAMP-GEFII Rim2 Complex in Incretin-potentiated Insulin Secretion." *J Biol Chem* (2001) 276(49): 46046-46053, Epub Oct. 11, 2001.

Kim et al., "Exendin-4 induction of cyclin D1 expression in INS-1 β-cells: involvement of cAMP-responsive element." *J Endocrinol* (2006) 188(3): 623-633.

Knowler et al., "Obesity in the Pima Indians: its magnitude and relationship with diabetes[1,2]." *Am J Clin Nutr* (1991) 53: 1543S-1551S.

Kwiterovich, "State-of-the-Art Update and Review: Clinical Trials of Lipid-Lowering Agents." *Am J Cardiol* (1998) 82(12A): 3U-17U.

Langer, "New Methods of Drug Delivery." *Science* (1990) 249: 1527-1533.

Levy et al., "Beta-cell Deterioration Determines the Onset and Rate of Progression of Secondary Dietary Failure in Type 2 Diabetes Mellitus: the 10-year Follow-up of the Belfast Diet Study." *Diabetes Med* (1998) 15: 290-296.

Li et al., "Glucagon-like Peptide-1 Receptor Signaling Modulates β Cell Apoptosis." *J Biol Chem* (2003) 278(1): 471-478.

Mahler et al., "Clinical Review 102 Type 2 Diabetes Mellitus: Update on Diagnosis, Pathophysiology, and Treatment." *J Clin Endocrinol Metab* (1999) 84(4): 1165-1171.

Matschinsky et al., "Perspectives in Diabetes the Network of Glucokinase-Expressing Cells in Glucose Homeostasis and the Potential of Glucokinase Activators for Diabetes Therapy." *Diabetes* (2006) 55(1): 1-12.

Matschinsky, "Glucokinase, Glucose Homeostasis, and Diabetes Mellitus." *Curr Diab Rep* (2005) 5(3): 171-176.

Meneilly et al., "The Effect of Glyburide on β-Cell Sensitivity to Glucose-Dependent Insulinotropic Polypeptide." *Diabetes Care* (1993) 16(1): 110-114.

Miura et al., "Glucagon-like peptide-1 induces a cAMP-dependent increase of $[Na^+]_i$ associated with insulin secretion in pancreatic β-cells." *Am J Physiol Endocrinol Metab* (2003) 285, E1001-E1009.

Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." *J Clin Invest* (1993) 91: 301-307.

Prentki et al., "Islet β cell Failure in type 2 dieabetes." *J Clin Invest* (2006) 116(7): 1802-1812.

Qader et al., "Expression of islet inducible nitric oxide synthase and inhibition of glucose-stimulated insulin release after long-term lipid infusion in the rat is counteracted by PACAP27." *Am J Physiol Endocrinol Metab* (2007) 292(5): E1447-E1455.

Reaven, "Insulin Resistance and Human Disease: A Short History." *J Basic & Clin Phys & Pharm* (1998) 9: 387-406.

Reimann et al., "Signaling Mechanisms Underlying the Release of Glucagon-Like Peptide 1." *Diabetes* (2006) 55(Suppl 2): S78-S85.

Rendell, "The Role of Sulphonylureas in the Management of Type 2 Diabetes Mellitus." *Drugs* (2004) 64(12): 1339-13.58.

Saltiel, "New Perspectives into the Molecular Pathogenesis and Treatment of Type 2 Diabetes." *Cell* (2001) 104: 517-529.

Saxena et al., "Genome-Wide Association Analysis Identifies Loci for Type 2 Diabetes and Triglyceride Levels." *Science* (2007) 316: 1331-1336.

Seino, "ATP-Sensitive Potassium Channels: A Model of Heteromultimeric Potassium Channel/Receptor Assemblies." *Annu Rev Physiol* (1999) 61: 337-362.

Shibasaki et al., "Interaction of ATP Sensor, cAMP Sensor, $Ca^{2+}$ Sensor, and Voltage-dependent $Ca^{2+}$ Channel in Insulin Granule Exocytosis." *J Biol Chem* (2004) 279(9): 7956-7961.

Steinthorsdottir et al., "A variant in CDKAL1 influences insulin response and risk of type 2 diabetes." *Nature Genetics* (2007) 39(6): 770-775.

Thorens et al., "Cloning and Functional Expression of the Human Islet GLP-1 Receptor: Demonstration that Exendin-4 is an Agonist and Exendin-(0-39) an Antagonist of the Receptor." *Diabetes* (1993) 42, 1678-1682.

Thorens, "GLUT2 in pancreatic and extra-pancreatic gluco-detection." *Mol Membr Biol* (2001) 18(4): 265-273.

Turner et al., "Glycemic Control With Diet, Sulfonylurea, Metformin, or Insulin in Patients With Type 2 Diabetes Mellitus: Progressive Requirement for Multiple Therapies (UKPDS 49)." *JAMA* (1999) 281(21): 2005-2012.

Turner et al., "Insulin resistance, impaired glucose tolerance and non-insulin-dependent diabetes, pathologic mechanisms and treatment: Current status and therapeutic possibilities." *Prog Drug Res* (1998) 51: 33-94.

United Kingdom Prospective Diabetes Study Group: "UKPDS 28: A Randomized Trial of Efficacy of Early Addition of Metformin in Sulfonylurea-Treated Type 2 Diabetes." *Diabetes Care* (1998) 21(1): 87-92.

Vilsbøll et al., "Reduced Postprandial Concentrations of Intact Biologically Active Glucagon-Like Peptide 1 in Type 2 Diabetic Patients." *Diabetes* (2001) 50: 609-613.

Walz et al., "Early and rapid development of insulin resistance, islet dysfunction and glucose intolerance after high-fat feeding in mice overexpressing phosphodiesterase 3B." *J Endocrinol* (2006) 189(3): 629-641.

Yamada et al., "Cytosolic $Ca^{2+}$ responses to sub-picomolar and nanomolar PACAP in pancreatic β-cells are mediated by VPAC2 and PAC1 receptors." *Regul Pept* (2004) 123(1-3): 147-153.

Zhou et al., "Overexpression of Repressive cAMP Response Element Modulators in High Glucose and Fatty Acid-treated Rat Islets." *J Biol Chem* (2003) 278(51): 51316-51323.

U.S. Appl. No. 13/006,298, filed Jan. 13, 2011, Song et al.

U.S. Appl. No. 13/032,513, filed Feb. 22, 2011, Chen et al.

Deacon, "Dipeptidyl peptidase 4 inhibition with sitagliptin: a new therapy for Type 2 diabetes." Expert Opinion on Investigational Drugs, 2007, 16(4):533-545.

Green et al., "Dipeptidyl peptidase IV (DPP IV) inhibitors: a newly emerging drug class for the treatment of type 2 diabetes." Diabetes Vasc. Dis. Res., 2006, 3:159-165.

Kahn, "The Importance of β-Cell Failure in the Development and Progression of Type 2 Diabetes." J. Clin. Endicrinol. Metab., 2001, 86:4047-4058.

Kim et al., "(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine: a potent, orally active dipeptidyl peptidase IV inhibitor for the treatment of type 2 diabetes." J. Med. Chem., 2005, 48(1):141-151.

Soga et al., "Lysophosphatidylcholine enhances glucose-dependent insulin secretion via an orphan G-protein-coupled receptor." Biochem. Biophys. Res. Commun., 2005, 326(4):744-751.

Still et al., "Rapid Chromatographic Techniques for Preparative Separation with Moderate Resolution." J. Org. Chem., 1978, 43(14):2923-2925.

U.S. Appl. No. 13/152,752, filed Jun. 3, 2011, Chen et al.

U.S. Appl. No. 13/165,651, filed Jun. 21, 2011, McWherter et al.

Chilean Examination Report dated Jun. 15, 2011 for Chilean Application No. 2042-2008.

* cited by examiner

Tissue map of rat IC-GPCR2

Tissue Map of mouse IC-GPCR2

SEQUENCE LISTING

<160> NUMBER OF SEQ ID NOS: 2

<210> SEQ ID NO 1
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | |
|---|---|---|
| atggaatcat ctttctcatt tggagtgatc cttgctgtcc tggcctccct catcattgct | 60 |
| actaacacac tagtggctgt ggctgtgctg ctgttgatcc acaagaatga tggtgtcagt | 120 |
| ctctgcttca ccttgaatct ggctgtggct gacaccttga ttggtgtggc catctctggc | 180 |
| ctactcacag accagctctc cagcccttct cggcccacac agaagaccct gtgcagcctg | 240 |
| cggatggcat ttgtcacttc ctccgcagct gcctctgtcc tcacggtcat gctgatcacc | 300 |
| tttgacaggt accttgccat caagcagccc ttccgctact tgaagatcat gagtgggttc | 360 |
| gtggccgggg cctgcattgc cgggctgtgg ttagtgtctt acctcattgg cttcctccca | 420 |
| ctcggaatcc ccatgttcca gcagactgcc tacaaagggc agtgcagctt ctttgctgta | 480 |
| tttcaccctc acttcgtgct gaccctctcc tgcgttggct tcttcccagc catgctcctc | 540 |
| tttgtcttct tctactgcga catgctcaag attgcctcca tgcacagcca gcagattcga | 600 |
| aagatggaac atgcaggagc catggctgga ggttatcgat ccccacggac tcccagcgac | 660 |
| ttcaaagctc tccgtactgt gtctgttctc attgggagct ttgctctatc ctggacccc | 720 |
| ttccttatca ctggcattgt gcaggtggcc tgccaggagt gtcacctcta cctagtgctg | 780 |
| gaacggtacc tgtggctgct cggcgtgggc aactccctgc tcaacccact catctatgcc | 840 |
| tattggcaga aggaggtgcg actgcagctc taccacatgg ccctaggagt gaagaaggtg | 900 |
| ctcacctcat tcctcctctt tctcttggcc aggaattgtg cccagagag cccagggaa | 960 |
| agttcctgtc acatcgtcac tatctccagc tcagagtttg atggctaa | 1008 |

<210> SEQ ID NO 2
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
                20                  25                  30

Ile His Lys Asn Asp Gly Val Ser Leu Cys Phe Thr Leu Asn Leu Ala
            35                  40                  45

Val Ala Asp Thr Leu Ile Gly Val Ala Ile Ser Gly Leu Leu Thr Asp
        50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ala Ser Val Leu Thr Val
                85                  90                  95

Met Leu Ile Thr Phe Asp Arg Tyr Leu Ala Ile Lys Gln Pro Phe Arg
                100                 105                 110

-continued

```
Tyr Leu Lys Ile Met Ser Gly Phe Val Ala Gly Ala Cys Ile Ala Gly
        115             120             125

Leu Trp Leu Val Ser Tyr Leu Ile Gly Phe Leu Pro Leu Gly Ile Pro
    130             135             140

Met Phe Gln Gln Thr Ala Tyr Lys Gly Gln Cys Ser Phe Phe Ala Val
145             150             155             160

Phe His Pro His Phe Val Leu Thr Leu Ser Cys Val Gly Phe Phe Pro
            165             170             175

Ala Met Leu Leu Phe Val Phe Phe Tyr Cys Asp Met Leu Lys Ile Ala
            180             185             190

Ser Met His Ser Gln Gln Ile Arg Lys Met Glu His Ala Gly Ala Met
    195             200             205

Ala Gly Gly Tyr Arg Ser Pro Arg Thr Pro Ser Asp Phe Lys Ala Leu
    210             215             220

Arg Thr Val Ser Val Leu Ile Gly Ser Phe Ala Leu Ser Trp Thr Pro
225             230             235             240

Phe Leu Ile Thr Gly Ile Val Gln Val Ala Cys Gln Glu Cys His Leu
            245             250             255

Tyr Leu Val Leu Glu Arg Tyr Leu Trp Leu Leu Gly Val Gly Asn Ser
        260             265             270

Leu Leu Asn Pro Leu Ile Tyr Ala Tyr Trp Gln Lys Glu Val Arg Leu
        275             280             285

Gln Leu Tyr His Met Ala Leu Gly Val Lys Lys Val Leu Thr Ser Phe
        290             295             300

Leu Leu Phe Leu Leu Ala Arg Asn Cys Gly Pro Glu Arg Pro Arg Glu
305             310             315             320

Ser Ser Cys His Ile Val Thr Ile Ser Ser Ser Glu Phe Asp Gly
            325             330             335
```

N-LINKED HETEROCYCLIC RECEPTOR AGONISTS FOR THE TREATMENT OF DIABETES AND METABOLIC DISORDERS

CROSS-REFERENCES TO RELATED APPLICATIONS

This application claims the benefit under 35 U.S.C. 119(e) of U.S. Provisional Application No. 60/950,859, filed 19 Jul. 2007, which is incorporated by reference in its entirety.

BACKGROUND OF THE INVENTION

Diabetes mellitus can be divided into two clinical syndromes, Type I and Type II diabetes mellitus. Type I diabetes, or insulin-dependent diabetes mellitus, is a chronic autoimmune disease characterized by the extensive loss of beta cells in the pancreatic islets of Langerhans (hereinafter referred to as "pancreatic islet cells" or "islet cells"), which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level). Although the exact trigger for this immune response is not known, patients with Type I diabetes have high levels of antibodies against pancreatic beta cells (hereinafter "beta cells"). However, not all patients with high levels of these antibodies develop Type I diabetes.

Type II diabetes, or non-insulin-dependent diabetes mellitus, develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type II diabetes (Kahn S E, *Am J Med* (2000) 108 Suppl 6a, 2S-8S).

The fasting hyperglycemia that characterizes Type II diabetes occurs as a consequence of the combined lesions of insulin resistance and beta cell dysfunction. The beta cell defect has two components: the first component, an elevation of basal insulin release (occurring in the presence of low, non-stimulatory glucose concentrations), is observed in obese, insulin-resistant pre-diabetic stages as well as in Type II diabetes. The second component is a failure to increase insulin release above the already elevated basal output in response to a hyperglycemic challenge. This lesion is absent in prediabetes and appears to define the transition from normo-glycemic insulin-resistant states to frank diabetes. There is currently no cure for diabetes. Conventional treatments for diabetes are very limited, and focus on attempting to control blood glucose levels in order to minimize or delay complications. Current treatments target either insulin resistance (metformin, thiazolidinediones ("TZDs")), or insulin release from the beta cell (sulphonylureas, exanatide). Sulphonylureas, and other compounds that act by depolarizing the beta cell, have the side effect of hypoglycemia since they cause insulin secretion independent of circulating glucose levels. One approve drug, Byetta (exanatide) stimulates insulin secretion only in the presence of high glucose, but is not orally available and must be injected. Januvia (sitagliptin) is another recently approved drug that increases blood levels of incretin hormones, which can increase insulin secretion, reduce glucagon secretion and have other less well characterized effects. However, Januvia and other dipeptidyl peptidases IV inhibitors may also influence the tissue levels of other hormones and peptides, and the long-term consequences of this broader effect have not been fully investigated. There is an unmet need for oral drugs that stimulate insulin secretion in a glucose dependent manner.

Progressive insulin resistance and loss of insulin secreting pancreatic beta cells are primary characteristics of Type II diabetes. Normally, a decline in the insulin sensitivity of muscle and fat is compensated for by increases in insulin secretion from the beta cell. However, loss of beta cell function and mass results in insulin insufficiency and diabetes (Kahn B B, *Cell* 92:593-596, 1998; Cavaghan M K, et al., *J Clin Invest* 106:329-333, 2000; Saltiel A R, *Cell* 104:517-529, 2001; Prentki M and Nolan C J, *J Clin Invest* 116:1802-1812 (2006); and Kahn S E, *J Clin Endicrinol Metab* 86:4047-4058, 2001). Hyperglycemia further accelerates the decline in beta cell function (UKPDS Group, *JAMA* 281: 2005-2012, 1999; Levy J, et al., *Diabetes Med* 15:290-296, 1998; and Zhou Y P, et al., *J Biol Chem* 278:51316-23, 2003). Several of the genes in which allelic variation is associated with an increased risk of Type II diabetes are expressed selectively in the beta cell (Bell G I and Polonsky K S, *Nature* 414:788-791 (2001); Saxena R, et al., *Science* (2007) Apr. 26; and Valgerdur Steinthorsdottir, et al., *Nature Genetics* (2007) Apr. 26).

Insulin secretion from the beta cells of pancreatic islets is elicited by increased levels of blood glucose. Glucose is taken up into the beta cell primarily by the beta cell and liver selective transporter GLUT2 (Thorens B, *Mol Membr Biol* 2001 October-December; 18(4):265-73). Once inside the cell, glucose is phosphorylated by glucokinase, which is the primary glucose sensor in the beta cell since it catalyzes the irreversible rate limiting step for glucose metabolism (Matschinsky F M, *Curr Diab Rep* 2005 June; 5(3):171-6). The rate of glucose-6-phosphate production by glucokinase is dependent on the concentration of glucose around the beta cell, and therefore this enzyme allows for a direct relationship between level of glucose in the blood and the overall rate of glucose oxidation by the cell. Mutations in glucokinase produce abnormalities in glucose dependent insulin secretion in humans giving further evidence that this hexokinase family member plays a key role in the islet response to glucose (Gloyn A L, et al., *J Biol Chem* 2005 Apr. 8; 280(14):14105-13, Epub 2005 Jan. 25). Small molecule activators of glucokinase enhance insulin secretion and may provide a route for therapeutic exploitation of the role of this enzyme (Guertin K R and Grimsby J, *Curr Med Chem* 2006; 13(15):1839-43; and Matschinsky F M, et al., *Diabetes* 2006 January; 55(1):1-12) in diabetes. Glucose metabolism via glycolysis and mitochondrial oxidative phosphorylation ultimately results in ATP production, and the amount of ATP produced in a beta cell is directly related to the concentration of glucose to which the beta cell is exposed.

Elevated ratios of ATP to ADP that occur in the presence of higher glucose result in the closure of the Kir6.2 channel via interaction with the SUR1 subunit of the channel complex. Closure of these channels on the plasma membrane of the beta cell results in de-polarization of the membrane and subsequent activation of voltage dependent calcium channels (VD-CCs) (Ashcroft F M, and Gribble F M, *Diabetologia* 42:903-919, 1999; and Seino S, *Annu Rev Physiol* 61:337-362, 1999). Calcium ion entry as well as release of calcium from intracellular stores triggers exocytosis of insulin granules, resulting is secretion of insulin into the blood stream. Agents which close the Kir6.2 channel such as sulphonylureas and metaglitinides (Rendell M, *Drugs* 2004; 64(12):1339-58; and Blickle J F, *Diabetes Metab* 2006 April; 32(2):113-20) also cause membrane depolarization, and therefore these agents stimulate insulin secretion in a glucose independent fashion. Potassium channel openers, such as diazoxide, inhibit insulin secretion by preventing elevated ATP/ADP ratios from closing the Kir6.2 channel (Hansen J B, *Curr Med Chem* 2006; 13(4):361-76). Calcium channel blockers, such as verapamil and nifedipine, can also inhibit insulin secretion (Henquin J C, (2004) *Diabetes* 53, S48-S58). Although sulfonylureas and metaglitinides are effective glucose lowering agents in the clinic, they act independently of blood glucose levels. Because they act independently of glucose levels, these drugs may result in hypoglycemia.

Glucose dependent insulin secretion from the beta cell is dependent on numerous neurotransmitters and blood-borne hormones, as well as local, intra-islet factors. CNS activation of the vagal innervation of the islet can lead to the release of small molecules such as acetylcholine and peptides such as vasoactive intestinal polypeptide (VIP), gastrin releasing peptide (GRP) and Pituitary Adenylate Cyclase Activating Peptide (PACAP). Acetylcholine activation of phospholipase C through the $G_{\alpha q}$-coupled GPCR M3 muscarinic receptor leads to release of Ca++ from intracellular stores (Gilon P and Henquin J C, *Endocr Rev* 2001 October; 22(5):565-604). Cholinergic agonists also lead to a subtle Na+-dependent plasma membrane depolarization that can work in concert with glucose-initiated depolarization to enhance insulin release (Gilon P and Henquin J C, *Endocr Rev* 2001 October; 22(5):565-604). VIP and PACAP each bind to an overlapping set of $G_\alpha$-coupled GPCRs (PAC1, VIPR1, and VIPR2) on the beta cell that lead to stimulation of adenylate cyclase and an increase in intracellular cAMP (Filipsson K, et al., *Diabetes* 2001 September; 50(9):1959-69; Yamada H, et al., *Regul Pept* 2004 Dec. 15; 123(1-3):147-53; and Qader S S, et al., *Am J Physiol Endocrinol Metab* 2007 May; 292(5):E1447-55).

Elevation of beta cell cAMP has a substantial potentiating effect on insulin secretion in the presence of stimulatory levels of glucose (see below). Unfortunately, many potentiators of glucose-stimulated insulin secretion also have effects outside of the islet which limit their ability to be used as diabetes therapeutics. For example, the best available selective muscarinic agonists which stimulate insulin secretion also stimulate multiple undesirable responses in multiple tissues (Rhoades R A and Tanner G A, eds. (2003) *Medical Physiology*, 2nd ed. Lippincott, Williams and Wilkins, ISBN 0-7817-1936-4). Likewise, VIP and PACAP receptors are present in multiple organ systems and mediate effects on the reproductive, immune and other diverse systems that make them less attractive as specific enhancers of glucose dependent insulin secretion.

Incretin hormones such as Glucagon-Like Peptide 1 (GLP-1) and Glucose-dependent Insulinotropic Polypeptide (GIP, also known as Gastric Inhibitory Polypeptide) also bind to specific $Galpha_s$-coupled GPCRs receptors on the surface of islet cells, including beta cells, and raise intracellular cAMP (Drucker D J, *J Clin Invest* 2007 January; 117(1):24-32). Although the receptors for these hormones are present in other cells and tissues, the overall sum of effects of these peptides appear to be beneficial to control of glucose metabolism in the organism (Hansotia T, et al., *J Clin Invest* 2007 January; 117(1):143-52, Epub 2006 Dec. 21). GIP and GLP-1 are produced and secreted from intestinal K and L cells, respectively, and these peptide hormones are released in response to meals by both direct action of nutrients in the gut lumen and neural stimulation resulting from food ingestion. GIP and GLP-1 have short half-lives in human circulation due to the action of the protease dipeptidyl-peptidase IV (DP-PIV), and inhibitors of this protease can lower blood glucose due to their ability to raise the levels of active forms of the incretin peptides. The glucose lowering that can be obtained with DPPIV inhibitors, however, is somewhat limited since these drugs are dependent on the endogenous release of the incretin hormones. Peptides (e.g., exanatide (Byetta)) and peptide-conjugates that bind to the GIP or GLP-1 receptors but are resistant to serum protease cleavage can also lower blood glucose substantially (Gonzalez C, et al., *Expert Opin Investig Drugs* 2006 August; 15(8):887-95), but these incretin mimetics must be injected and tend to induce a high rate of nausea and therefore are not ideal therapies for general use in the Type II diabetic population. The clinical success of DPPIV inhibitors and incretin mimetics, though far from ideal, do point to the potential utility of compounds that increase incretin activity in the blood or directly stimulate cAMP in the beta cell. Some studies have indicated that beta cell responsiveness to GIP is diminished in Type II diabetes (Nauck M A, et al., *J Clin Invest* 91:301-307 (1993); and Elahi D, et al., *Regul Pept* 51:63-74 (1994)). Restoration of this responsiveness (Meneilly G S, et al., *Diabetes Care* 1993 January; 16(1):110-4) may be a promising way to improve beta cell function in vivo.

Since increased incretin activity has a positive effect on glucose dependent insulin secretion and perhaps other mechanisms that lead to lower blood glucose, it is also of interest to explore therapeutic approaches to increasing incretin release from intestinal K and L cells. GLP-1 secretion appears to be attenuated in Type II diabetes (Vilsboll T, et al., *Diabetes* 50:609-613), so improving incretin release may ameliorate this component of metabolic dysregulation. Nutrients such as glucose and fat in the gut lumen prompt incretin secretion by interaction with apical receptors (Vilsboll T, et al., *Diabetes* 50:609-613). GLP-1 and GIP release can also result from neural stimulation; acetylcholine and GRP can enhance incretin release in a manner perhaps analogous to the effects of these neurotransmitters on the beta cell in regard to insulin secretion (Brubaker P, *Ann N Y Acad Sci* 2006 July; 1070:10-26; and Reimann F, et al., *Diabetes* 2006 December; 55(Suppl 2):S78-S85). Somatostatin, leptin and free fatty acids also appear to modulate incretin secretion (Brubaker P, *Ann N Y Acad Sci* 2006 July; 1070:10-26; and Reimann F, et al., *Diabetes* 2006 December; 55(Suppl 2):S78-S85). To date, however, there does not appear to be a way to selectively impact these pathways to promote incretin secretion for therapeutic benefit. There is a need for oral drugs that stimulate incretin secretion in the treatment of diabetes.

Incretins can also increase the rate of beta cell proliferation and decrease the apoptotic rates of beta cells in animal models (Farilla L, et al., *Endocrinology* 2002 November; 143(11): 4397-408) and human islets in vitro (Farilla L, et al., *Endocrinology* 2003 December; 144(12):5149-58). The net result of these changes is an increase in beta cell number and islet mass, and this should provide for increased insulin secretory capacity, which is another desired aim of anti-diabetic therapies. GLP-1 has also been shown to protect islets from the destructive effects of agents such as streptozotocin by blocking apoptosis (Li Y, et al., *J Biol Chem* 2003 Jan. 3; 278(1): 471-8). Cyclin D1, a key regulator of progression through the cell cycle, is up-regulated by GLP-1, and other agents that increase cAMP and PKA activity also have a similar effect (Friedrichsen B N, et al., *J Endocrinol* 2006 March; 188(3): 481-92; and Kim M J, et al., *J Endocrinol* 2006 March; 188(3):623-33). Increased transcription of the cyclin D1 gene occurs in response to PKA phosphorylation of CREB (cAMP-response element binding) transcription factors (Hussain M A, et al., *Mol Cell Biol* 2006 October; 26(20):

7747-59). There is a need for oral drugs that increase beta cell number and islet mass in the treatment of diabetes.

Beta cell cAMP levels may also be raised by inhibiting the degradation of this second messenger by phosphodiesterases to AMP (Furman B and Pyne N, *Curr Opin Investig Drugs* 2006 October; 7(10):898-905). There are several different cAMP phosphodiesterases in the beta cell, and many of these have been shown to serve as a brake on glucose-dependent insulin secretion. Inhibitors of cAMP phosphodiesterases have been shown to increase insulin secretion in vitro and in vivo, including PDE1C, PDE3B, PDE10 (Han P, et al., *J Biol Chem* 1999 Aug. 6; 274(32):22337-44; Hamdahl L, et al., *J Biol Chem* 2002 Oct. 4; 277 (40):37446-55; Walz H A, et al., *J Endocrinol* 2006 June; 189(3):629-41; Choi Y H, et al., *J Clin Invest* 2006 December; 116(12):3240-51; and Cantin L D, et al., *Bioorg Med Chem Lett* 2007 May 15; 17(10):2869-73), but so far, no PDEs have been found to have the cell type selectivity necessary to avoid undesirable effects. However, this remains an area of active investigation due to the potential for amplification of the effects of incretins and other agents that stimulate adenylate cyclase.

There appear to be multiple mechanisms by which cAMP elevation in the beta cell can enhance glucose dependent insulin secretion. Classically, many of the intracellular effects of cAMP are mediated by the cAMP-dependent protein kinase (protein kinase A, PKA) (Hatakeyama H, et al., *J Physiol* 2006 Jan. 15; 570(Pt 2):271-82). PKA consists of a complex of two regulatory and two catalytic domains; binding of cAMP to the catalytic domains releases the catalytic domains and results in increased protein phosphorylation activity. One of the downstream effects of this kinase activity is enhanced efficiency of insulin exocytosis (Gromada J, et al., *Diabetes* 1998 January; 47(1):57-65). Another cAMP binding protein is Epac, a guanine nucleotide exchange factor (GEF) (Kashima Y, et al., *J Biol Chem* 2001 Dec. 7; 276(49): 46046-53, Epub 2001 Oct. 11; and Shibasaki T, et al., *J Biol Chem* 2004 Feb. 27; 279(9):7956-61), which mediates a cAMP-dependent, but PKA-independent, increase in insulin exocytosis. Epac activated by cAMP may also enhance of release of intracellular Ca++ (Holz G G, *Diabetes* 2004 January; 53(1):5-13). The effects of cAMP on insulin secretion are dependent on elevated glucose levels, so raising cAMP in the pancreatic beta cell is an important goal for therapeutics of Type II diabetes.

Agents that raise intracellular cAMP levels in the beta cell increase insulin secretion in a glucose dependent manner (Miura Y and Matsui H, *Am J Physiol Endocrinol Metab* (2003) 285, E1001-E1009). One mechanism for raising cAMP is by the action of G-protein coupled cell surface receptors, which stimulate the enzyme adenylate cyclase to produce more cAMP. The GLP-1 receptor, which is the target of exanatide, is an example of such a receptor (Thorens B, et al., *Diabetes* (1993) 42, 1678-1682). There is a need for oral drugs that increase intracellular levels of cAMP in the treatment of diabetes.

BRIEF SUMMARY OF THE INVENTION

Quite surprisingly, we now find that novel agonists of another G-protein coupled receptor ("GPCR"), IC-GPCR2 can raise intracellular cAMP levels (see In Vitro Activity Table 1 in Biological Example 1). IC-GPCR2 is also referred to as RUP3 and GPR119. Such raised cAMP levels increase insulin secretion in a glucose dependent manner (see Biological Examples 2 and 3) and thus provide a useful treatment for, inter alia, Type II diabetes. The novel agonists described in this invention are orally active (see Biological Example 3), providing a significant differentiating feature to exanatide. Biological Example 4 shows the tissue specific expression of GPR119. Additionally, Biological Example 5 describes methods to determine the effect of GPR119 agonists on the secretion of incretins. Biological Example 6 shows methods of determining improvements in diabetes parameters widely accepted by skilled artisans in an animal diabetes model using ZDF rats. We have also found that nucleic acid probes corresponding to IC-GPCR2 are highly enriched in pancreatic islets (the majority of which are beta cells), and are not detected in any other tissue examined (see FIGS. 1 and 2). This surprising occurrence means that the novel agonists described in the current invention will be useful in diagnosing diseases effecting pancreatic islets (including beta cells) such as diabetes. Agonists of IC-GPCR2 capable of raising intracellular cAMP levels have now been identified using a cell-based screen (see Biological Example 1).

The present invention provides compounds represented by Formula I:

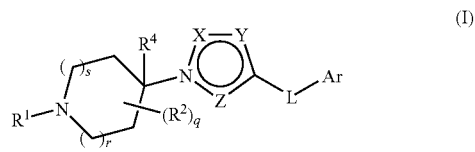

as well as pharmaceutical compositions containing those compounds.

The present invention further provides compounds represented by Formula II:

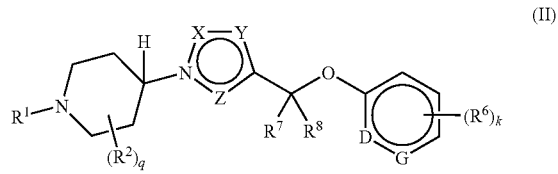

as well as pharmaceutical compositions containing compounds of Formula II.

Also provided are methods of treating diseases such as Type II diabetes and other diseases and conditions using one or more of these compounds or compositions, as described in or more of these compounds or compositions, as described in further detail below. The invention also provides methods of raising intracellular levels of cyclic AMP (cAMP) by using one or more of the compounds described herein. Further, the compounds may be used to stimulate insulin production and stimulate secretion of insulin, glucagon-like peptide 1 (GLP1), and glucose dependent insulinotropic polypeptide (GIP) in a mammal, in particular a human. Additionally, the compounds described herein are useful in lowering blood glucose when administered to a subject in need of treatment to lower blood glucose.

In a related aspect, the present invention provides methods of diagnosing a number of diseases and conditions using labeled compounds of Formula I.

DETAILED DESCRIPTION OF THE INVENTION

Abbreviations and Definitions

Figure 1:
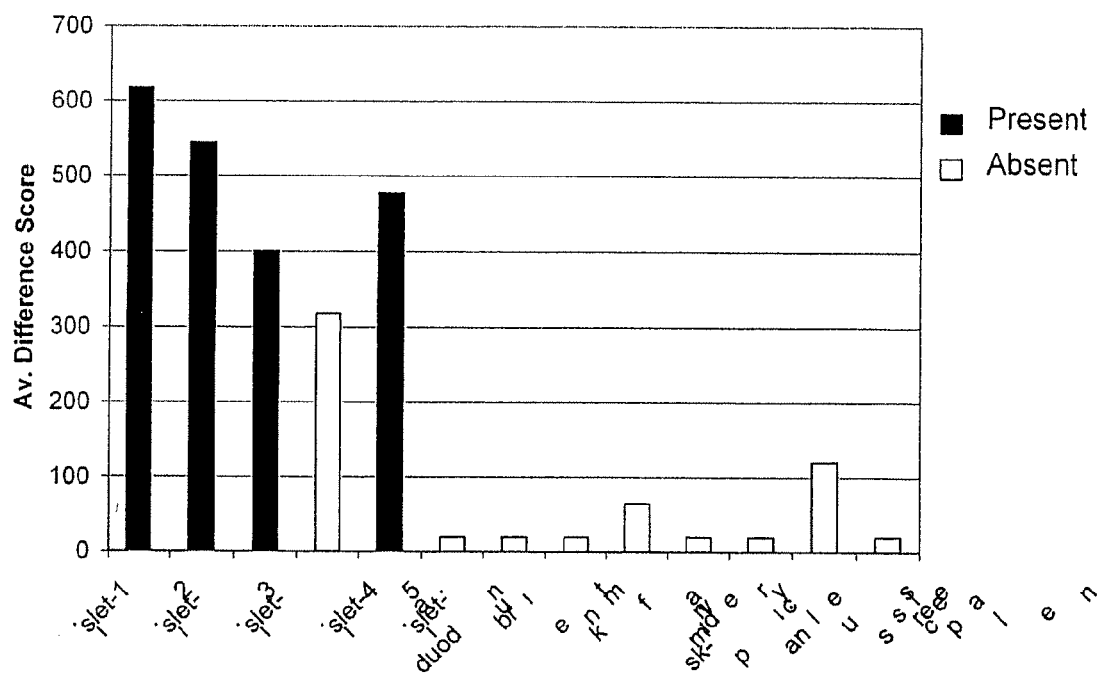
FIG. 1 illustrates rat islet chip hybridization results demonstrating the islet enrichment of IC-GPCR2 mRNA relative to other tissues. Chips were hybridized with equivalent amounts of cRNA from five sets of isolated rat islets, as well as the rat tissues: brain, duodenum, adipose (fat), kidney, liver, skeletal muscle, pancreas and spleen. The "Average Difference" score reflects the relative abundance of the IC-GPCR2 mRNA in each of the tissues. The Affymetrix GeneChip analysis package called the IC-GPCR2 mRNA are "Present" in four of five islet samples and "Absent" in each of the other tissues.
Figure 2:
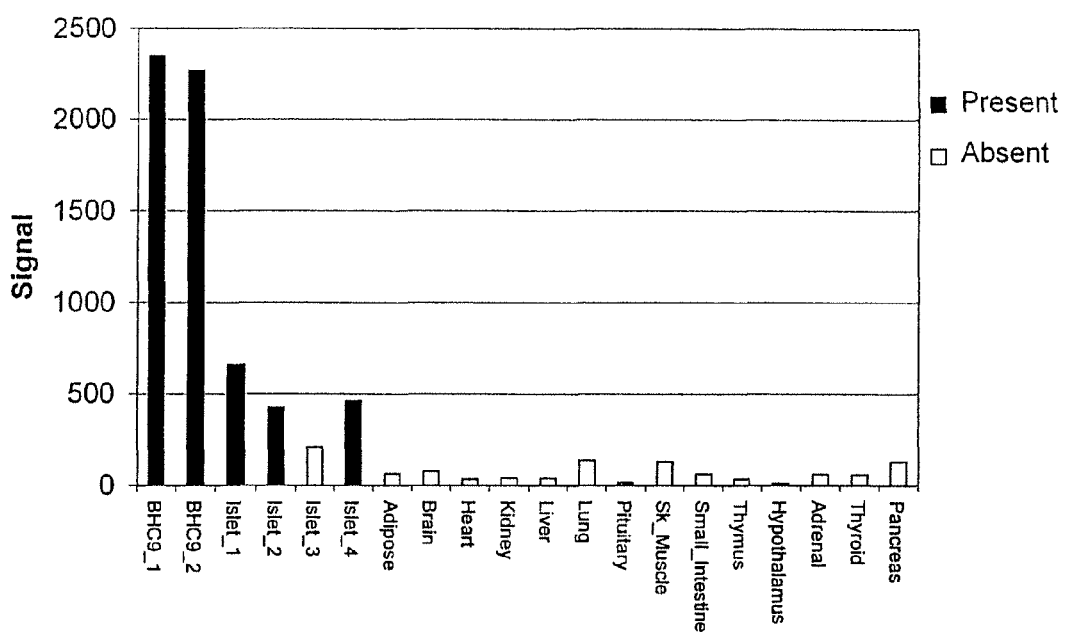
FIG. 2 illustrates mouse islet chip hybridization results demonstrating the islet enrichment of IC-GPCR2 mRNA relative to other tissues. Chips were hybridized with equivalent amounts of cRNA from a pancreatic beta cell line (betaHC9), four sets of isolated mouse islets, as well as the mouse tissues: adipose (fat), brain, heart, kidney, liver, lung, pituitary, skeletal muscle, small intestine, thymus, hypothalamus, adrenal, thyroid and pancreas. The "Signal" score reflects the relative abundance of the IC-GPCR2 mRNA in each of the tissues. The Affymetrix GeneChip analysis package called the IC-GPCR2 mRNA are "Present" in betaHC9, and three of four islet samples. The Affymetrix GeneChip analysis package called the IC-GPCR2 mRNA "Absent" in each of the other tissues.

The abbreviations used herein are conventional, unless otherwise defined: AcOH: acetic acid; nBuLi: n-butyllithium; $Cs_2CO_3$: cesium carbonate; $CH_2Cl_2$ or DCM: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMSO: dimethyl sulfoxide; $Et_3N$: triethylamine; EtOAc: ethyl acetate; $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; MeCN: acetonitrile; MeI: methyl iodide; MeOH: methanol; $MgSO_4$: magnesium sulfate; $MgCO_3$: magnesium carbonate; MsCl: mesyl chloride; $NaHSO_3$: sodium hydrogen sulfite; mCPBA: metachloroperoxybenzoic acid; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; $SOCl_2$: thionyl chloride; THF: tetrahydrofuran; TLC: thin layer chromatography.

Unless otherwise stated, the following terms used in the specification and claims have the meanings given below.

"Alkyl" refers to monovalent saturated aliphatic hydrocarbyl groups having from 1 to 10 carbon atoms and, in some embodiments, from 1 to 6 carbon atoms. "$C_{u\text{-}v}$alkyl" refers to alkyl groups having from u to v carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkylidene" or "alkylene" refers to divalent saturated aliphatic hydrocarbyl groups having from 1 to 10 carbon atoms and, in some embodiments, from 1 to 6 carbon atoms. "($C_{u\text{-}v}$)alkylene" refers to alkylene groups having from u to v carbon atoms. The alkylidene and alkylene groups include branched and straight chain hydrocarbyl groups. For example "($C_{1\text{-}6}$)alkylene" is meant to include methylene, ethylene, propylene, 2-methylpropylene, pentylene, and the like.

"Substituted alkylidene" or "substituted alkylene" refers to an alkylidene group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and in some embodiments from 2 to 6 carbon atoms or 2 to 4 carbon atoms and having at least one site of vinyl unsaturation (>C=C<). For example, ($C_{u\text{-}v}$)alkenyl refers to alkenyl groups having from u to v carbon atoms and is meant to include for example, ethenyl, propenyl, 1,3-butadienyl, and the like.

"Substituted alkenyl" refers to alkenyl groups having from 1 to 3 substituents and, in some embodiments, 1 to 2 substituents, selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined as herein and with the proviso that any hydroxy or thiol substitution is not attached to an acetylenic carbon atom.

"Alkenylene" refers to divalent alkenyl groups having from 2 to 10 carbon atoms and, in some embodiments, from 2 to 6 carbon atoms. "$(C_{u\text{-}v})$alkenylene" refers to alkenylene groups having from u to v carbon atoms.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2\text{-}C_6)$alkynyl is meant to include ethynyl, propynyl, and the like.

"Substituted alkynyl" refers to alkynyl groups having from 1 to 3 substituents and, in some embodiments, from 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkynylene" refers to divalent alkynyl groups having from 2 to 10 carbon atoms and, in some embodiments, from 2 to 6 carbon atoms. "$(C_{u\text{-}v})$alkynylene" refers to alkynylene groups having from u to v carbon atoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —$NR^{20}$C(O)H, —$NR^{20}$C(O)alkyl, —$NR^{20}$C(O)substituted alkyl, —$NR^{20}$C(O)cycloalkyl, —$NR^{20}$C(O)substituted cycloalkyl, —$NR^{20}$C(O)alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —$S(O)_2$-alkyl, —$S(O)_2$-substituted alkyl, —$S(O)_2$-alkenyl, —$S(O)_2$-substituted alkenyl, —$S(O)_2$-cycloalkyl, —$S(O)_2$-substituted cylcoalkyl, —$S(O)_2$-aryl, —$S(O)_2$-substituted aryl, —$S(O)_2$-heteroaryl, —$S(O)_2$-substituted heteroaryl, —$S(O)_2$-heterocyclyl, and —$S(O)_2$-substituted heterocyclyl and wherein $R^{21}$ and $R^{22}$ are optionally joined together with the nitrogen bound thereto to form a heterocyclyl or substituted heterocyclyl group, provided that $R^{21}$ and $R^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{21}$ is hydrogen and $R^{22}$ is alkyl, the substituted amino group is sometimes referred to herein as alkylamino. When $R^{21}$ and $R^{22}$ are alkyl, the substituted amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)$NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, substituted alkoxy, amino, substituted amino, and acylamino, and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{20}$C(O)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —S(O)$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—S(O)$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{20}$—S(O)$_2$NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{25}$)NR$^{23}$R$^{24}$ where R$^{25}$, R$^{23}$, and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3 or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Arylalkyl" or "Aryl($C_1$-$C_z$)alkyl" refers to the radical —$R^uR^v$ where $R^u$ is an alkylene group (having eight or fewer main chain carbon atoms) and $R^v$ is an aryl group as defined herein. Thus, "arylalkyl" refers to groups such as, for example, benzyl, and phenylethyl, and the like. Similarly, "Arylalkenyl" means a radical —$R^uR^v$ where $R^u$ is an alkenylene group and $R^v$ is an aryl group as defined herein, e.g., styrenyl, 3-phenyl-2-propenyl, and the like.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —$N_3$.

"Hydrazino" refers to the group —$NHNH_2$.

"Substituted hydrazino" refers to the group —$NR^{26}NR^{27}R^{28}$ where $R^{26}$, $R^{27}$, and $R^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —$S(O)_2$-alkyl, —$S(O)_2$-substituted alkyl, —$S(O)_2$-alkenyl, —$S(O)_2$-substituted alkenyl, —$S(O)_2$-cycloalkyl, —$S(O)_2$-substituted cylcoalkyl, —$S(O)_2$-aryl, —$S(O)_2$-substituted aryl, —$S(O)_2$-heteroaryl, —$S(O)_2$-substituted heteroaryl, —$S(O)_2$-heterocyclic, and —$S(O)_2$-substituted heterocyclic and wherein $R^{27}$ and $R^{28}$ are optionally joined, together with the nitrogen bound thereto to form a heterocyclic or substituted heterocyclic group, provided that $R^{27}$ and $R^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "carbonitrile" refers to the group —CN.

"Carbonyl" refers to the divalent group —C(O)— which is equivalent to —C(=O)—.

"Carboxyl" or "carboxy" refers to —C(O)OH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —$NR^{20}$—C(O)O-alkyl, —$NR^{20}$—C(O)O-substituted alkyl, —$NR^{20}$—C(O)O-alkenyl, —$NR^{20}$—C(O)O-substituted alkenyl, —$NR^{20}$—C(O)O-alkynyl, —$NR^{20}$—C(O)O-substituted alkynyl, —$NR^{20}$—C(O)O-aryl, —$NR^{20}$—C(O)O-substituted aryl, —$NR^{20}$—C(O)O-cycloalkyl, —$NR^{20}$—C(O)O-substituted cycloalkyl, —$NR^{20}$—C(O)O-heteroaryl, —$NR^{20}$—C(O)O-substituted heteroaryl, —$NR^{20}$—C(O)O-heterocyclic, and —$NR^{20}$—C(O)O-substituted heterocyclic wherein $R^{20}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "$C_{u-v}$cycloalkyl" refers to cycloalkyl groups having u to v carbon atoms as ring members. "$C_{u-v}$cycloalkenyl" refers to cycloalkenyl groups having u to v carbon atoms as ring members.

"Cycloalkenyl" refers to a partially saturated cycloalkyl ring having at least one site of >C=C< ring unsaturation.

"Substituted cycloalkyl" refers to a cycloalkyl group, as defined herein, having from 1 to 8, or 1 to 5, or in some embodiments 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are as defined herein. The term "substituted cycloalkyl" includes substitutes cycloalkenyl groups.

"Cycloalkyloxy" refers to —O-cycloalkyl wherein cycloalkyl is as defined herein.

"Substituted cycloalkyloxy refers to —O-(substituted cycloalkyl) wherein substituted cycloalkyl is as defined herein.

"Cycloalkylthio" refers to —S-cycloalkyl wherein substituted cycloalkyl is as defined herein.

"Substituted cycloalkylthio" refers to —S-(substituted cycloalkyl) wherein substituted cycloalkyl is as defined herein.

"Guanidino" refers to the group —NHC(=NH)NH$_2$.

"Substituted guanidino" refers to —NR$^{29}$C(=NR$^{29}$)N(R$^{29}$)$_2$ where each R$^{29}$ is independently selected from the group consisting of hydrogen, alkyl, substituted alkyl, aryl, substituted aryl, heteroaryl, substituted heteroaryl, heterocyclyl, and substituted heterocyclyl and two R$^{29}$ groups attached to a common guanidino nitrogen atom are optionally joined together with the nitrogen bound thereto to form a heterocyclic or substituted heterocyclic group, provided that at least one R$^{29}$ is not hydrogen, and wherein said substituents are as defined herein.

"Halo" or "halogen" refers to fluoro, chloro, bromo and iodo.

"Haloalkyl" refers to substitution of alkyl groups with 1 to 5 or in some embodiments 1 to 3 halo groups.

"Haloalkoxy" refers to substitution of alkoxy groups with 1 to 5 or in some embodiments 1 to 3 halo groups.

"Hydroxy" or "hydroxyl" refers to the group —OH.

"Heteroaryl" refers to an aromatic group of from 1 to 14 carbon atoms and 1 to 6 heteroatoms selected from the group consisting of oxygen, nitrogen, and sulfur and includes a 5 to 18 member ring or ring system that includes a single ring (e.g., imidazolyl) or multiple rings (e.g., benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g., 1,2,3,4-tetrahydroquinolin-6-yl and 5,6,7,8-tetrahydroquinolin-3-yl). In one embodiment, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"Substituted heteroaryl" refers to heteroaryl groups that are substituted with from 1 to 8, or in some embodiments 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy refers to the group —O-(substituted heteroaryl) wherein heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein heteroaryl is as defined herein.

"Heterocycle" or "heterocyclic" or "heterocyclo" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the term "heterocyclic", "heterocycle", "heterocyclo", "heterocycloalkyl" or "heterocyclyl" applies when there is at least one ring heteroatom and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In one embodiment, the nitrogen and/or sulfur atom(s) of the heterocyclic group are optionally oxidized to provide for the N-oxide, sulfinyl, sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Substituted heterocycle" or "substituted heterocyclic" or "substituted heterocyclo" or "substituted heterocycloalkyl" or "substituted heterocyclyl" refers to heterocyclic groups, as defined herein, that are substituted with from 1 to 5 or in some embodiments 1 to 3 of the substituents as defined for substituted cycloalkyl.

"Heterocyclyloxy" refers to the group —O-heterocyclyl wherein heterocyclyl is as defined herein.

"Substituted heterocyclyloxy" refers to the group —O-(substituted heterocyclyl) wherein heterocyclyl is as defined herein.

"Heterocyclylthio" refers to the group —S-heterocyclyl wherein heterocyclyl is as defined herein.

"Substituted heterocyclylthio" refers to the group —S-(substituted heterocyclyl) wherein heterocyclyl is as defined herein.

Examples of heterocycle and heteroaryl groups include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

"Oxide" refers to products resulting from the oxidation of one or more heteroatoms. Examples include N-oxides, sulfoxides, and sulfones.

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown here attached to bonds marked with wavy lines is substituted with a spirocycloalkyl group:

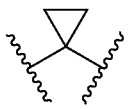

"Sulfonyl" refers to the divalent group —S(O)$_2$—.

"Substituted sulfonyl" refers to the group —S(O)$_2$-alkyl, —S(O)$_2$-substituted alkyl, —S(O)$_2$-alkenyl, —S(O)$_2$-substituted alkenyl, —S(O)$_2$-alkynyl, —S(O)$_2$-substituted alkynyl, —S(O)$_2$-cycloalkyl, —S(O)$_2$-substituted cycloalkyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-S(O)$_2$—, phenyl-S(O)$_2$—, and 4-methylphenyl-S(O)$_2$—.

"Sulfonyloxy" refers to the group —OS(O)$_2$-alkyl, —OS(O)$_2$-substituted alkyl, —OS(O)$_2$-alkenyl, —OS(O)$_2$-substituted alkenyl, —OS(O)$_2$-cycloalkyl, —OS(O)$_2$-substituted cylcoalkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any forms of the compounds within the generic and subgeneric formulae, such as an oxide, ester, prodrug, pharmaceutically acceptable salt, or solvate. Unless specified otherwise, the term further includes the racemates, stereoisomers, and tautomers of the compound or compounds.

"Racemates" refers to a mixture of enantiomers.

"Solvate" or "solvates" of a compound refer to those compounds, where compounds are as defined above, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans.

"Stereoisomer" or "stereoisomers" refer to compounds that differ in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th ed., J March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a patient. Prodrugs of a compound of the present invention are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound I is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a patient (e.g., by allowing an orally administered compound to be more readily absorbed into the blood) or which enhance delivery of the parent compound to a biological compartment (e.g., the brain or lymphatic system) relative to the parent species. Prodrugs include ester, amide, carbamate (e.g., N,N-dimethylaminocarbonyl) forms of hydroxy functional groups of compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the ACS Symposium Series, and in Edward B. Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium. When the molecule contains a basic functionality, pharmaceutically acceptable salts include acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in P. Heinrich Stahl, Camille G. Wermuth (Eds.), Handbook of Pharmaceutical Salts Properties, Selection, and Use; 2002.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

"Patient" refers to mammals and includes humans and non-human mammals. Examples of patients include, but are not limited to mice, rats, hamsters, guinea pigs, pigs, rabbits, cats, dogs, goats, sheep, cows, and humans.

The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, monkeys).

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991) and Harrison and Harrison, et al., COMPENDIUM OF SYNTHETIC ORGANIC METHODS, Vols. 1-8 (John Wiley and Sons 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, and possesses acceptable toxicities. Acceptable carriers or excipients include those that are acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing or reducing the risk of developing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A preferred embodiment of the invention is treatment of a disease that consists of relieving the disease.

The term "diagnosing" refers to determining the presence or absence of a particular disease or condition. Additionally, the term refers to determining the level or severity of a particular disease or condition, as well as monitoring of the disease or condition to determine its response to a particular therapeutic regimen.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven G M, *J Basic & Clin Phys & Pharm* (1998) 9:387-406 and Flier J, *Ann Rev Med* (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

The term "diabetes mellitus" or "diabetes" means a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are Type I diabetes and Type II diabetes. As described above, Type I diabetes is generally the result of an absolute deficiency of insulin, the hormone that regulates glucose utilization. Type II diabetes often occurs in the presence of normal, or even elevated levels of insulin and can result from the inability of tissues to respond appropriately to insulin. Most Type II diabetic patients are insulin resistant and have a relative deficiency of insulin, in that insulin secretion can not compensate for the resistance of peripheral tissues to respond to insulin. In addition, many Type II diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of Type I or Type II diabetes.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "abdominal obesity" is defined by a cutoff point of waist circumference $\geqq 102$ cm in men and $\geqq 80$ cm in women, as recommended by the third report of the national cholesterol education program expert panel on detection, evaluation, and treatment of high blood cholesterol in adults (NCEP/ATP Panel III).

The guidelines for diagnosis of Type II diabetes, impaired glucose tolerance, and gestational diabetes have been outlined by the American Diabetes Association (see, e.g., The Expert Committee on the Diagnosis and Classification of Diabetes Mellitus, Diabetes Care, (1999) Vol 2 (Suppl 1):S5-19).

The term "secretagogue" means a substance or compound that stimulates secretion. For example, an insulin secretagogue is a substance or compound that stimulates secretion of insulin.

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications that generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, e.g., cardiovascular disease and peripheral vascular disease. Cardiovascular disease refers to diseases of blood vessels of the heart. See, e.g., Kaplan R M, et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels.

The term "modulate" refers to the treating, prevention, suppression, enhancement or induction of a function or condition. For example, compounds can modulate Type II diabetes by increasing insulin in a human, thereby suppressing hyperglycemia.

The term "triglyceride(s)" ("TGs"), as used herein, incorporates its common usage. TGs consist of three fatty acid molecules esterified to a glycerol molecule. TGs serve to store fatty acids that are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "hyperlipidemia" includes, but is not limited to, the following:

(1) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels.

Risk factors for hyperlipidemia include, but are not limited to, the following: (1) disease risk factors, such as a history of Type I diabetes, Type II diabetes, Cushing's syndrome, hypothyroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index ("BMI") greater than 27.8 kg/m$^2$ for men and 27.3 kg/m$^2$ for women (BMI equals weight (kg)/height (m$^2$). Obesity is linked to a variety of medical conditions including diabetes and hyperlipidemia. Obesity is also a known risk factor for the development of Type II diabetes (see, e.g., Barrett-Conner E, *Epidemol Rev* (1989) 11:172-181; and Knowler, et al., *Am J Clin Nutr* (1991) 53:1543-1551).

The term "pancreas" refers to a gland organ in the digestive and endocrine system of vertebrates, including mammals. The pancreas secretes both digestive enzymes and hormones such as insulin, GLP-1 and GIP as well as other hormones.

The term "islet" or "islet of Langerhans" refers to endocrine cells of the pancreas that are grouped together in islets and secrete insulin and other hormones.

The term "beta cell" refers to cells found in the islet of Langerhans that secrete insulin, amylin, and other hormones.

The term "endocrine cell" refers to cells that secrete hormones into the blood stream. Endocrine cells are found in various glands and organ systems of the body including the pancreas, intestines, and other organs.

The term "L cell" refers to gut endocrine cells that produce GLP-1.

The term "K cell" refers to gut endocrine cells that produce GIP.

The term "incretin" refers to a group of hormones that increases insulin secretion in response to food intake. Incretins include GLP-1 and GIP.

The term "insulin" refers to a polypeptide hormone that regulates glucose metabolism. Insulin binds to insulin receptors in insulin sensitive cells and mediates glucose uptake. Insulin is used to treat Type I diabetes and may be used to treat Type II diabetes.

The term "GLP-1" or "glucagon-like peptide" is a peptide hormone primarily produced by L cells. GLP-1 increases insulin secretion, decreases glucagon secretion, increases beta cell mass and insulin gene expression, inhibits acid secretion and gastric emptying in the stomach, and decreases food intake by increasing satiety.

The term "GIP" or "gastric inhibitory peptide" or "glucose dependent insulinotropic polypeptide" refers to a peptide hormone produced primarily by K cells. GIP stimulates insulin secretion. GIP also has significant effects on lipid metabolism.

The term "cAMP" or "cyclic AMP" or "cyclic adenosine monophosphate" refers to an intracellular signaling molecule involved in many biological processes, including glucose and lipid metabolism.

The term "agonist" refers to a compound that binds to a receptor and triggers a response in a cell. An agonist mimics the effect of an endogenous ligand, a hormone for example, and produces a physiological response similar to that produced by the endogenous ligand.

The term "partial agonist" refers to a compound that binds to a receptor and triggers a partial response in a cell. A partial agonist produces only a partial physiological response of the endogenous ligand.

General

The present invention derives from the discovery of compounds that act as agonists of IC-GPCR2 (Seq. ID 1) using a cell-based screen. A stable CHO cell line expressing IC-GPCR2 under the control of the CMV promoter was used and cAMP levels were measured in the cells using a homogeneous time resolved fluorescence assay. With a parental CHO cell line as a control, increased cAMP levels could be measured and compounds identified that, like exanatide, raise cAMP in cells (see In Vitro Activity Table in Biological Example 1). Since elevated intracellular cAMP levels in the beta cell increase insulin secretion in a glucose dependant manner (see Biological Examples 2 and 3), the present invention is useful for the treatment of, inter alia, Type II diabetes and other diseases associated with poor glycemic control. The novel agonists described in this invention are orally active (see Biological Example 3), providing a significant differentiating feature to exanatide. Additionally, the islet specific expression of the receptor for the novel agonists of the present invention (see Biological Example 4) also make the present invention useful for the diagnosis of, inter alia, diabetes and other diseases associated with beta cell health.

Embodiments of the Invention

Compounds

The compounds of the present invention are represented by Formula I:

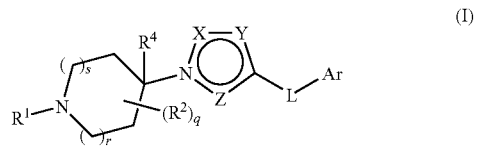

(I)

wherein, the letters X, Y and Z are each independently selected from N and C(R$^3$). The subscript q is 0, 1, 2, 3 or 4; the subscript r is 0, 1, 2 or 3; the subscript s is 0, 1, 2, or 3, and the sum of r+s is ≦4. The letter L is —(CH$_2$)$_n$— wherein n is 2, 3 or 4 and optionally at least one CH$_2$ is replaced by O, N(R$^5$), S, S(O) or S(O)$_2$, and any remaining CH$_2$ is optionally substituted with one or two substituents selected from the group consisting of halo, C$_{1-4}$alkyl, C$_{3-6}$cycloalkyl and C$_{1-4}$haloalkyl. Ar is an aryl or heteroaryl group, wherein the aryl or heteroaryl group is optionally substituted with from one, two, three, four or five R$^6$ substituents.

In one embodiment, Ar is a six-membered aryl optionally substituted with from 1 to 3 R$^6$ substituents or a heteroaryl, optionally substituted with from 1 to 3 R$^6$ substituents. In another embodiment, Ar is selected from the group consisting of optionally substituted phenyl, optionally substituted pyridyl, optionally substituted pyrimidinyl, optionally substituted pyrazinyl, and optionally substituted pyridazinyl.

Turning next to the R groups, $R^1$ is selected from the group consisting of H, $C_{1-10}$alkyl, $C_{1-10}$substituted alkyl, $C_{3-7}$cycloalkyl, $C_{3-7}$substituted cycloalkyl, $C_{2-10}$alkenyl, $C_{2-10}$alkynyl, —$X^1$—C(O)$R^a$, —$X^1$—C(O)O$R^a$, —$X^1$—C(O)N$R^a R^b$, —S(O)$_2 R^a$, a 4- to 7-membered heterocyclyl group, aryl and a 5- to 10-membered heteroaryl group, wherein each of said cycloalkyl group, heterocyclyl group, aryl group and heteroaryl group is optionally substituted with from one, two, three or four substituents independently selected from the group consisting of halo, $C_{1-10}$alkyl, $C_{1-10}$substituted alkyl, $C_{3-7}$cycloalkyl, $C_{2-10}$alkenyl, $C_{2-10}$alkynyl, aryl, heteroaryl, —CN, —N$R^a$C(O)$R^b$, —N$R^a$C(O)N$R^a R^b$, —NO$_2$, —O$R^a$, —N$R^a R^b$, —C(O)$R^a$, —C(O)O$R^a$, —C(O)N$R^a R^b$, —S$R^a$, —S(O)$R^a$, —S(O)$_2 R^a$, —N$R^a$S(O)$_2 R^b$, and —S(O)$_2$N$R^a R^b$, or optionally $R^a$ and $R^b$ are combined to form a 4-, 5- or 6-membered ring, and $X^1$ is selected from the group consisting of a bond, $C_{1-4}$alkylene, $C_{2-6}$alkenylene, $C_{2-6}$alkynylene, —C(O)—, and —C(O)(CH$_2$)$_{1-4}$—, wherein the aliphatic portions of $X^1$ are optionally substituted with one, two or three groups selected from the group consisting of halo, $C_{1-4}$alkyl, and $C_{1-4}$substituted alkyl. In one embodiment, $R^1$ is selected from the group consisting of —$X^1$—C(O)$R^a$, —$X^1$—C(O)O$R^a$, optionally substituted aryl group and optionally substituted heteroaryl group. In another embodiment, $R^1$ is —C(O)O$R^a$, pyrimidine optionally substituted with from one to two substituents independently selected from the group consisting of halo, $C_{3-6}$cycloalkyl, $C_{1-10}$alkyl, and $C_{1-10}$substituted alkyl, or oxadiazole optionally substituted with from one to two substituents independently selected from the group consisting of halo, $C_{3-6}$cycloalkyl, $C_{1-10}$alkyl, and $C_{1-10}$substituted alkyl.

Each $R^2$ is independently selected from the group consisting of halo, $C_{-5}$alkyl, $C_{1-5}$substituted alkyl, $C_{3-7}$cycloalkyl, $C_{3-7}$substituted cycloalkyl, —C(O)$R^a$, —C(O)O$R^a$, —C(O)N$R^a R^b$, —O$R^a$, —N$R^a R^b$, —N$R^a$C(O)$R^b$, —S(O)$R^a$, —S(O)$_2 R^a$ and —S(O)$_2$N$R^a R^b$, and wherein when the subscript q is 2, 3, or 4, two $R^2$ groups can optionally cyclize to form a ring.

Each $R^3$ is independently selected from the group consisting of H, halo, $C_{1-4}$alkyl, $C_{1-4}$haloalkyl, $C_{3-7}$cycloalkyl, aryl and —O$R^a$.

$R^4$ is selected from the group consisting of H, halo, $C_{1-6}$alkyl, and $C_{1-6}$substituted alkyl.

$R^5$ is selected from the group consisting of H, $C_{1-4}$alkyl, $C_{1-4}$haloalkyl, $C_{3-6}$cycloalkyl, —C(O)$R^a$ and —S(O)$_2 R^a$.

Each $R^6$ is independently selected from the group consisting of H, halo, $C_{1-10}$alkyl, $C_{1-10}$substituted alkyl, $C_{3-7}$cycloalkyl, $C_{3-7}$substituted cycloalkyl, $C_{2-10}$alkenyl, $C_{2-10}$alkynyl, —CN, —NO$_2$, —O$R^a$, —N$R^a R^b$, —C(O)$R^a$, —C(O)O$R^a$, —C(O)N$R^a R^b$, —N$R^a$C(O)$R^b$, —N$R^a$C(O)O$R^b$, —N$R^a$C(O)N$R^a R^b$, —S$R^a$, —S(O)$R^a$, S(O)$_2 R^a$, —N$R^a$S(O)$R^b$, —N$R^a$S(O)$_2 R^b$, —S(O)$_2$N$R^a R^b$, a 4- to 7-membered heterocyclyl group, aryl and a 5- to 10-membered heteroaryl group, wherein each of said heterocyclyl groups, said aryl and heteroaryl groups are optionally substituted with from one to four substituents independently selected from halo, oxo, $C_{1-4}$alkyl, $C_{1-4}$haloalkyl, $C_{3-7}$cycloalkyl, —CN, —NO$_2$, —O$R^a$, —N$R^a R^b$, —C(O)$R^a$, —C(O)O$R^a$, —C(O)N$R^a R^b$, N$R^a$C(O)$R^b$, N$R^a$C(O)O$R^b$, —N$R^a$C(O)N$R^a R^b$, —S$R^a$, —S(O)$R^a$, —S(O)$_2 R^a$, —N$R^a$S(O)$R^b$, —N$R^a$S(O)$_2 R^b$ and —S(O)$_2$N$R^a R^b$ or optionally $R^a$ and $R^b$ are combined to form a 4-, 5- or 6-membered ring. In one embodiment, each $R^6$ is independently selected from the group consisting of H, halo, —N$R^a R^b$, —N$R^a$C(O)$R^b$, —S(O)$R^a$, —S(O)$_2 R^a$, $C_{1-3}$alkyl, $C_{1-3}$haloalkyl, substituted heteroaryl and unsubstituted heteroaryl. In one preferred embodiment, each $R^6$ independently selected from the group consisting of H, fluoro, chloro, methyl, ethyl, —CF$_3$, imidazolyl, pyrazolyl, triazolyl, tetrazolyl, —S(O)$R^a$, and —S(O)$_2 R^a$.

For each of the above groups, each $R^a$ and $R^b$ is independently selected from the group consisting of H, $C_{1-10}$alkyl, $C_{1-10}$haloalkyl, $C_{3-10}$cycloalkyl, heterocyclyl, $C_{2-10}$alkenyl, $C_{2-10}$alkynyl, aryl, 5- to 6-membered heteroaryl and aryl$C_{1-4}$alkyl; and wherein the aliphatic portions of each of said $R^a$ and $R^b$ is optionally substituted with from one to three groups selected from the group consisting of halo, —O$R''$, —OC(O)$R''$, —OC(O)N($R''$)$_2$, —S$R''$, —S(O)$R''$, —S(O)$_2 R''$, —S(O)$_2$N($R''$)$_2$, —N$R''$S(O)$_2 R''$, —C(O)N($R''$)$_2$, —C(O)$R''$, —N$R''$C(O)$R''$, —N$R''$C(O)N($R''$)$_2$, —C(O)O$R''$, —N$R''$C(O)O$R''$, —CN, —NO$_2$, —N($R''$)$_2$ and —N$R''$S(O)$_2$N($R''$)$_2$, wherein each $R''$ is independently H, $C_{1-3}$haloalkyl or an unsubstituted $C_{1-6}$alkyl; and wherein the aryl and heteroaryl portions are optionally substituted with from one to three groups selected from halo, —O$R'''$, —OC(O)N($R'''$)$_2$, —S$R'''$, —S(O)$R'''$, —S(O)$_2 R'''$, —S(O)$_2$N($R'''$)$_2$, —N$R'''$S(O)$_2 R'''$, —C(O)N($R'''$)$_2$, —C(O)$R'''$, —N$R'''$C(O)$R'''$, —N$R'''$C(O)N($R'''$)$_2$, —C(O)O$R'''$, —N$R'''$C(O)O$R'''$, —CN, —NO$_2$, —N($R'''$)$_2$ and —N$R'''$S(O)$_2$N($R'''$)$_2$, wherein each $R'''$ is independently H, $C_{1-3}$haloalkyl or an unsubstituted $C_{1-6}$alkyl.

The compounds provided herein also include any pharmaceutically acceptable salts, solvates, stereoisomers, tautomers, and esters of the compounds as well as any isotopically labeled isomers thereof. In general, the compounds useful in the methods described herein are those compounds of the formula above, wherein the molecular weight of the compound is less than 1200, more preferably less than about 1000, still more preferably less than about 800 and still more preferably from about 200 to about 600.

The ring having X, Y and Z as ring substituents will, in one group of embodiments, be a ring in which one of X, Y or Z is N. In another group of embodiments, two of X, Y and Z are N. In still another group of embodiments, the ring is one in which all three of X, Y and Z are N. A further group of embodiments comprises compounds in which X, Y, and Z are all C($R^3$). Representations of these embodiments are provided as:

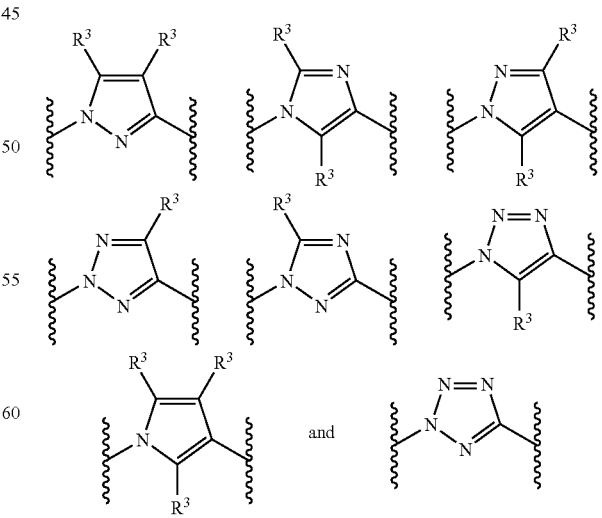

wherein the wavy lines indicate the positions of attachment to either L or to the carbon atom bearing $R^4$.

In one group of preferred embodiments, the ring having X, Y and Z is selected from:

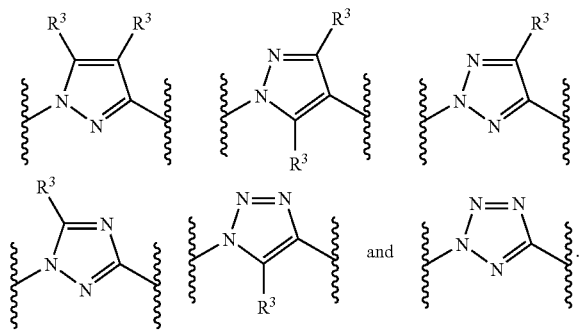

and

For each of the above groups of embodiments, an additional set of embodiments are those in which subscript r is 1, subscript s is 0 or 1, subscript q is 0, 1 or 2 and Ar is phenyl, optionally substituted with from 1 to 3 $R^6$ substituents. Still another set of embodiments are those in which subscript r is 1, subscript s is 0 or 1, subscript q is 0 and Ar is selected from the group consisting of pyridyl, pyrimidinyl and pyrazinyl, each of which is optionally substituted with from 1, 2 or 3 $R^6$ substituents. In one embodiment, the compounds of Formula I are those compounds in which the subscript n is 2. Yet another set of embodiments are those in which subscript r is 1, subscript s is 0 or 1, subscript q is 0, 1 or 2, and subscript n is 2. In still another set of embodiments, subscript r is 1, subscript s is 0 or 1, subscript q is 0, 1 or 2, subscript n is 2 and one $CH_2$ is replaced by O.

In another group of embodiments of Formula I, subscript r is 1; subscript s is 0 or 1; subscript q is 0, 1 or, 2; subscript n is 2 and one of $CH_2$ is replaced by O, S or $N(R^5)$; $R^4$ is selected from H, F, $CH_3$ and OH; and the ring having X, Y and Z is selected from pyrazole, imidazole, 1,2,3-triazole and 1,2,4-triazole. Preferably, Ar is phenyl, optionally substituted with from 1 to 3 $R^6$ substituents. More preferably, Ar is substituted with from 1 to 2 $R^6$ substituents independently selected from the group consisting of halo, $C_{1-10}$alkyl, $C_{1-10}$haloalkyl, —CN, —$NO_2$, —$OR^a$, —$NR^aR^b$, —$C(O)R^a$, —$C(O)OR^a$, —$C(O)NR^aR^b$, —$NR^aC(O)R^b$, —$NR^aC(O)OR^b$, —$SR^a$, —$S(O)R^a$, —$S(O)_2R^a$, —$NR^aSR^b$, —$NR^aS(O)R^b$, —$NR^aS(O)_2R^b$, —$S(O)_2NR^aR^b$, a 4- to 5-membered heterocyclo group, aryl, and a 5- to 6-membered heteroaryl group. In some embodiments, each $R^6$ is independently selected from the group consisting of halo, $OR^a$, —$NR^aR^b$, $NR^aC(O)R^b$, —$NR^aC(O)OR^b$, —$SR^a$, —$S(O)R^a$, —$S(O)_2R^a$, —$NR^aSR^b$, —$NR^aS(O)R^b$, —$NR^aS(O)_2R^b$, —$S(O)_2NR^aR^b$, a 4- to 5-membered heterocyclo group, aryl, and a 5- to 6-membered heteroaryl group. Within each of the groups of embodiments and preferred embodiments, one group of further preferred embodiments are those in which $R^1$ is a 5- to 10-membered heteroaryl group, and is optionally substituted with from one to two substituents independently selected from halo, $C_{1-10}$alkyl, $C_{1-10}$haloalkyl, $C_{3-7}$cycloalkyl, $C_{2-10}$alkenyl, $C_{2-10}$alkynyl, aryl, heteroaryl, CN, $NO_2$, —$OR^a$, —$NR^aR^b$, —$C(O)OR^a$, —$C(O)NR^aR^b$, —$NR^aC(O)R^b$, —$NR^aC(O)OR^b$, —$SR^a$, —$S(O)R^a$, —$S(O)_2R^a$, —$NR^aSR^b$, —$NR^aS(O)R^b$, —$NR^aS(O)_2R^b$, and —$S(O)_2NR^aR^b$. Still further preferred are those embodiments in which $R^1$ is a pyridine or pyrimidine, and is optionally substituted with from one to two substituents independently selected from halo, $C_{1-10}$alkyl, $C_{1-10}$haloalkyl, $C_{3-7}$cycloalkyl, $C_{2-10}$alkenyl, $C_{2-10}$alkynyl, aryl, heteroaryl, CN, $NO_2$, —$OR^a$, —$NR^aR^b$, —$C(O)R^a$, —$C(O)OR^a$, —$C(O)NR^aR^b$, —$NR^aC(O)R^b$, —$NR^aC(O)OR^b$, —$SR^a$, —$S(O)R^a$, —$S(O)_2R^a$, —$NR^aSR^b$, —$NR^aS(O)R^b$, —$NR^aS(O)_2R^b$, and —$S(O)_2NR^aR^b$. In still another group of embodiments, $R^1$ is selected from the group consisting of —$X^1$—C(O)$R^a$, —$X^1$—C(O)O$R^a$, $X^1$—C(O)NR$^a$R$^b$ and —$S(O)_2R^a$.

In another aspect, this invention provides a compound represented by Formula II:

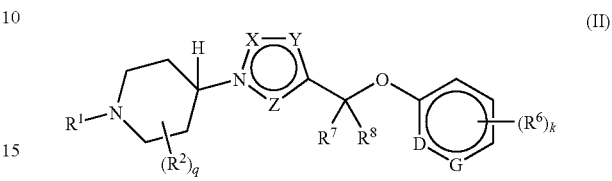

(II)

wherein, the letters X, Y, Z, D and G are each independently selected from the group consisting of N and $C(R^3)$. The subscript q is 0, 1, 2, 3 or 4. The subscript k is 1, 2 or 3.

$R^1$ is selected from the group consisting of H, $C_{1-10}$alkyl, $C_{1-10}$substituted alkyl, $C_{3-7}$cycloalkyl, $C_{3-7}$substituted cycloalkyl, $C_{2-10}$alkenyl, $C_{2-10}$alkynyl, —$X^1$—C(O)$R^a$, —$X^1$—C(O)O$R^a$, —$X^1$—C(O)NR$^a$R$^b$, —$S(O)_2R^a$, a 4- to 7-membered heterocyclyl group, aryl and a 5- to 10-membered heteroaryl group, wherein each of said cycloalkyl group, heterocyclyl group, aryl group and heteroaryl group is optionally substituted with from 1 to 4 substituents independently selected from the group consisting of halo, $C_{1-10}$alkyl, $C_{1-10}$substituted alkyl, $C_{3-7}$cycloalkyl, $C_{2-10}$alkenyl, $C_{2-10}$alkynyl, aryl, heteroaryl, —CN, —$NR^aC(O)R^b$, —$NR^aC(O)NR^aR^b$, —$NO_2$, —$OR^a$, —$NR^aR^b$, —$C(O)R^a$, —$C(O)OR^a$, —$C(O)NR^aR^b$, —$SR^a$, —$S(O)R^a$, —$S(O)_2R^a$, —$NR^aS(O)_2R^b$, and —$S(O)_2NR^aR^b$, or optionally $R^a$ and $R^b$ are combined to form a 4-, 5- or 6-membered ring, and $X^1$ is selected from the group consisting of a bond, $C_{1-4}$alkylene, $C_{2-6}$alkenylene, $C_{2-6}$alkynylene, —C(O)—, and —C(O)($CH_2$)$_{1-4}$—, wherein the aliphatic portions of $X^1$ are optionally substituted with one to three groups selected from the group consisting of halo, $C_{1-4}$alkyl, and $C_{1-4}$substituted alkyl.

Each $R^2$ is independently selected from the group consisting of halo, $C_{1-5}$alkyl, $C_{1-5}$ substituted alkyl, $C_{3-7}$cycloalkyl, —$C(O)R^a$, —$C(O)OR^a$, —$C(O)NR^aR^b$, —$OR^a$, —$NR^aR^b$, —$NR^aC(O)R^b$, —$S(O)R^aR^b$, —$S(O)_2R^a$ and —$S(O)_2NR^aR^b$, and wherein when the subscript q is 2, 3 or 4, two $R^2$ groups can optionally cyclize to form a ring.

Each $R^3$ is independently selected from the group consisting of H, halo, $C_{1-4}$alkyl, $C_{1-4}$haloalkyl, $C_{3-7}$cycloalkyl, aryl and $OR^a$.

Turning now to $R^6$, each $R^6$ is independently selected from the group consisting of H, halo, $C_{1-10}$alkyl, $C_{1-10}$substituted alkyl, $C_{3-7}$cycloalkyl, $C_{2-10}$alkenyl, $C_{2-10}$alkynyl, —CN, —$NO_2$, —$OR^a$, —$NR^aR^b$, —$C(O)R^a$, —$C(O)OR^a$, —$C(O)NR^aR^b$, —$NR^aC(O)R^b$, —$NR^aC(O)OR^b$, —$NR^aC(O)NR^aR^b$, —$SR^a$, —$S(O)R^a$, $S(O)_2R^a$, —$NR^aS(O)R^b$, —$NR^aS(O)_2R^b$, —$S(O)_2NR^aR^b$, a 4- to 7-membered heterocyclyl group, aryl and a 5- to 10-membered heteroaryl group, wherein each of said heterocyclyl groups, said aryl and heteroaryl groups are optionally substituted with from one to four substituents independently selected from halo, oxo, $C_{1-4}$alkyl, $C_{1-4}$haloalkyl, $C_{3-7}$cycloalkyl, —CN, —$NO_2$, —$OR^a$, —$NR^aR^b$, —$C(O)R^a$, —$C(O)OR^a$, —$C(O)NR^aR^b$, —$NR^aC(O)R^b$, —$NR^aC(O)_2R^b$, —NR AC(O)NR$^a$R$^b$, —$SR^a$, —$S(O)R^a$, —$S(O)_2R^a$, —$NR^aS(O)_2R^b$, and —$S(O)_2NR^aR^b$ or optionally $R^a$ and $R^b$ are combined to form a 4-, 5- or 6-membered ring.

Each $R^a$ and $R^b$ is independently selected from the group consisting of H, $C_{1-10}$alkyl, $C_{1-10}$haloalkyl, $C_{3-10}$cycloalkyl, heterocyclyl, $C_{2-10}$alkenyl, $C_{2-10}$alkynyl, aryl, 5- to 6-membered heteroaryl and aryl$C_{1-4}$alkyl; and wherein the aliphatic portions of each of said $R^a$ and $R^b$ is optionally substituted with from one to three groups selected from the group consisting of halo, —OR″, —OC(O)R″, —OC(O)N(R″)$_2$, —SR″, —S(O)R″, —S(O)$_2$R″, —S(O)$_2$N(R″)$_2$, —NR″S(O)$_2$R″, —C(O)N(R″)$_2$, —C(O)R″, —NR″C(O)R″, —NR″C(O)N(R″)$_2$, —C(O)OR″, —NR″C(O)OR″, —CN, —NO$_2$, —N(R″)$_2$ and —NR″S(O)$_2$N(R″)$_2$, wherein each R″ is independently H, $C_{1-3}$haloalkyl or an unsubstituted $C_{1-6}$alkyl.

Each $R^7$ and $R^8$ is independently selected from the group consisting of hydrogen, $C_{1-6}$alkyl, $C_{1-6}$haloalkyl, $C_{3-7}$cycloalkyl.

One embodiment of the present invention are compounds in which q is 0 or 1, and/or one or both $R^7$ and $R^8$ are hydrogen.

In one embodiment, the ring having X, Y, and Z in Formula II is a ring in which X, Y, and Z are all CR$^3$. Alternatively, one of X, Y, and Z, is N or two of X, Y, and Z are N, or three of X, Y, and Z are N. Representations of some of these embodiments are provided below:

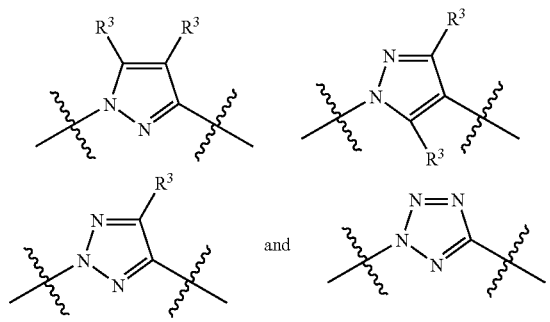

wherein, the wavy lines indicate the position of attachment to either the piperidinyl group or the aryloxymethyl group.

A further embodiment provides compounds in which R$^3$ is hydrogen and/or one or both R$^7$ and R$^8$ of Formula II are hydrogen.

Another embodiment provides compounds of Formula II wherein R$^1$ is selected from the group consisting of —X$^1$—C(O)R$^a$, —X$^1$—C(O)OR$^a$, optionally substituted aryl and optionally substituted heteroaryl group. Alternatively, R$^1$ is —C(O)OR$^a$, pyrimidine optionally substituted with from one to two substituents independently selected from the group consisting of halo, $C_{3-6}$cycloalkyl, $C_{3-6}$substituted cycloalkyl, $C_{1-10}$alkyl, and $C_{1-10}$substituted alkyl, or oxadiazole optionally substituted with from one to two substituents independently selected from the group consisting of halo, $C_{3-6}$cycloalkyl, $C_{1-10}$alkyl, and $C_{1-10}$substituted alkyl.

Yet another group of embodiments provides compounds in which subscript k is 1 or 2. Additionally, in an embodiment of Formula II wherein subscript k is 1 or 2, each R$^6$ is independently selected from the group consisting of halo, —NR$^a$R$^b$, —NR$^a$C(O)R$^b$, —S(O)R$^a$, —S(O)$_2$R$^a$, $C_{1-3}$alkyl, $C_{1-3}$haloalkyl, substituted heteroaryl and unsubstituted heteroaryl. Further, in an embodiment of Formula II wherein subscript k is 1 or 2, each R$^6$ is independently selected from the group consisting of H, fluoro, chloro, methyl, ethyl, —CF$_3$, imidazolyl, triazolyl, tetrazolyl, —S(O)R$^a$, and —S(O)$_2$R$^a$.

One embodiment of the invention provides compounds of Formula II wherein R$^1$ is a heteroaryl group optionally substituted with from one to two substituents selected from the group consisting of halo, $C_{1-6}$alkyl, and $C_{1-6}$haloalkyl, and each R$^6$ is independently selected from the group consisting of halo, —NR$^a$R$^b$, —NR$^a$C(O)R$^b$, —S(O)R$^a$, —S(O)$_2$R$^a$, $C_{1-3}$alkyl, $C_{1-3}$haloalkyl substituted heteroaryl and unsubstituted heteroaryl.

Compounds of Formula II are also provided wherein R$^1$ is a substituted pyrimidinyl or substituted oxadiazolyl group, and each R$^6$ is independently selected from the group consisting of fluoro, chloro, methyl, ethyl, —CF$_3$, imidazolyl, triazolyl, tetrazolyl, —S(O)R$^a$, and —S(O)$_2$R$^a$.

Yet another embodiment provides compounds of Formula II wherein k is 2, R$^1$ is a pyrimidinyl group optionally substituted with from one to two substituents selected from the group consisting of halo, $C_{1-6}$alkyl, and $C_{1-6}$haloalkyl, and each R$^6$ is independently selected from the group consisting of H, fluoro, chloro, methyl, ethyl, —CF$_3$, imidazolyl, triazolyl, tetrazolyl, —S(O)R$^a$, and —S(O)$_2$R$^a$.

In one embodiment of the present invention are compounds of Formula II wherein q is 0, k is 2, both R$^7$ and R$^8$ are hydrogen, R$^1$ is a heteroaryl group optionally substituted with from one to two substituents selected from the group consisting of halo, $C_{1-6}$alkyl, and $C_{1-6}$haloalkyl, and each R$^6$ is independently selected from the group consisting of hydrogen, halo, —SR$^a$, —S(O)R$^a$, —S(O)$_2$R$^a$, —S(O)$_2$NR$^a$R$^b$, substituted heteroaryl and unsubstituted heteroaryl.

Yet another embodiment of the present invention are compounds of Formula II wherein q is 0, k is 2, both R$^7$ and R$^8$ are hydrogen, R$^1$ is an unsubstituted pyrimidinyl or a substituted pyrimidinyl substituted with from one to two substituents selected from the group consisting of halo, $C_{1-6}$alkyl, and $C_{1-6}$haloalkyl, and each R$^6$ is independently selected from the group consisting of hydrogen, halo, —SR$^a$, —S(O)R$^a$, —S(O)$_2$R$^a$, —S(O)$_2$NR$^a$R$^b$, substituted heteroaryl and unsubstituted heteroaryl.

Still another embodiment of the present invention are compounds of Formula II wherein q is 0, k is 2, both R$^7$ and R$^8$ are hydrogen, R$^1$ is an unsubstituted pyrimidinyl or a substituted pyrimidinyl substituted with from one to two substituents selected from the group consisting of halo, $C_{1-6}$alkyl, and $C_{1-6}$haloalkyl, and each R$^6$ is independently selected from the group consisting of hydrogen, halo, —SR$^a$, —S(O)R$^a$, —S(O)$_2$R$^a$, —S(O)$_2$NR$^a$R$^b$, and tetrazolyl.

Preparation of Compounds of the Invention

The compounds of the present invention can be prepared in a number of ways familiar to one skilled in the art of organic synthesis. The synthetic route of compounds in the present invention is not limited to the methods outlined below or as provided in the Examples. Individual compounds may require manipulation of the conditions in order to accommodate various functional groups and may require appropriate use of protecting groups. Purification, if necessary, can be accomplished on a silica gel column eluted with the appropriate organic solvent system. Also, reverse phase HPLC or recrystallization may be employed.

Compositions and Methods of Treatment

In accordance with the present invention methods of treating a disease or condition selected from the group consisting of Type I diabetes, Type II diabetes and metabolic syndrome are provided. The method comprises administering to a subject in need of such treatment an effective amount of a compound of the present invention.

In another aspect, methods of raising intracellular levels of cyclic AMP in a cell expressing GPR119 are provided. The method comprises exposing a cell that expresses GPR119 to a compound of the invention. Cyclic AMP levels are determined by the methods disclosed in the Example sections herein.

In one embodiment, the cell that expresses GPR119 is a pancreatic cell, an islet cell, or a beta cell, an intestinal endocrine cell, an L cell or a K cell.

Another aspect of the invention provides a method of stimulating insulin production in a mammal, in particular a human. The method comprises administering an effective amount of a compound of the invention to the mammal. In response to administration of a compound to the subject, insulin is produced by the beta cells. Biological Example 2 provides detailed methods by which a skilled artisan can measure insulin secretion in laboratory animals in response to administration of a compound of the invention.

In another aspect, the invention provides a method of stimulating insulin secretion in a mammal, in particular a human. The method comprises administering an effective amount of a compound of the invention to the mammal. In response to administration of a compound to the subject, insulin is secreted into the blood stream by the beta cells. Biological Example 2 provides methods of determining insulin secretion in rats.

A further aspect of the invention provides a method of stimulating glucose-dependent insulin secretion in a mammal, in particular a human. The method comprises administering an effective amount of a compound of the invention to the mammal. After administration to the subject, insulin is secreted into the blood stream by the beta cells in a glucose-dependent manner. Biological Example 3 provides methods and data that show the blood glucose lowering effects of the compounds of the invention.

In another embodiment, the invention provides methods of lowering blood glucose in a mammal, preferably a human. The method comprises administering an effective amount of a compound of the invention to the mammal. In response to administration of a compound to the subject, blood glucose levels are lowered. The method further comprises steps to measure blood glucose levels before and after administration of a compound of the invention. Blood glucose levels are easily measured by numerous commercially available glucose monitoring devices that measure blood glucose from samples of blood or urine. Blood glucose can also be measured by commercially available glucometers that do not require blood or urine samples. Biological Example 5 provides methods that teach how to measure improvements in diabetes parameters, including blood glucose monitoring.

Another aspect of the invention provides a method of stimulating incretin production in a mammal, in particular a human. The method comprises administering an effective amount of a compound of the invention to the mammal. In response to administration of a compound to the subject, glucagon-like peptide 1 and glucose-dependent insulinotropic polypeptide is produced by the intestinal endocrine cells. Biological Example 4 provides detailed methods by which a skilled artisan can measure incretin production in laboratory animals in response to administration of a compound of the invention.

In accordance with the present invention, a therapeutically effective amount of a compound of Formula I can be used for the preparation of a pharmaceutical composition useful for treating Type II diabetes and/or lowering the plasma level of glucose. In addition, a therapeutically effective amount of a compound of Formula I can be used for the preparation of a pharmaceutical composition useful for treating other indications that include diabetes as a component, such as metabolic syndrome, as well as indications that can be improved as a result of increased insulin production (such as the early stages of Type I diabetes).

The compositions of the invention can include compounds of Formula I, pharmaceutically acceptable salts thereof, or a hydrolysable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type II diabetes.

The compounds of Formula I that are used in the methods of the present invention can be incorporated into a variety of formulations for therapeutic administration. More particularly, the compounds of Formula I can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

The compounds of Formula I can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. Compounds of Formula I can be administered alone, in combination with each other, or they can be used in combination with other known compounds (see Combination Therapy below).

Suitable formulations for use in the present invention are found in Remington's Pharmaceutical Sciences (Mack Publishing Company (1985) Philadelphia, Pa., 17th ed.), which is incorporated herein by reference. Moreover, for a brief review of methods for drug delivery, see, Langer, Science (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds of Formula I can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethyl sulfoxide ("DMSO") also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays, animal models, or microdosing of human subjects.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are preferred. The data obtained from these cell culture assays and animal studies can be used in formulating a dosage range that is not toxic for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition (see, e.g., Fingl, et al., 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 100 mg. A more preferred unit dose is between 1 mg to about 20 mg. Such unit doses can be administered more than once a day, for example 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 20 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner N, et al., *Prog Drug Res* (1998) 51:33-94; Haffner S, *Diabetes Care* (1998) 21:160-178; and DeFronzo R, et al. (eds.), *Diabetes Reviews* (1997) Vol. 5 No. 4). A number of studies have investigated the benefits of combination therapies with oral agents (see, e.g., Mahler R, *J Clin Endocrinol Metab* (1999) 84:1165-71; United Kingdom Prospective Diabetes Study Group: UKPDS 28, *Diabetes Care* (1998) 21:87-92; Bardin C W, (ed.), CURRENT THERAPY IN ENDOCRINOLOGY AND METABOLISM, 6th Edition (Mosby—Year Book, Inc., St. Louis, Mo. 1997); Chiasson J, et al., *Ann Intern Med* (1994) 121:928-935; Coniff R, et al., *Clin Ther* (1997) 19:16-26; Coniff R, et al., *Am J Med* (1995) 98:443-451; and Iwamoto Y, et al., *Diabet Med* (1996) 13:365-370; Kwiterovich P, *Am J Cardiol* (1998) 82(12A): U-17U). These studies indicate that diabetes modulation can be further improved by the addition of a second agent to the therapeutic regimen. Combination therapy includes administration of a single pharmaceutical dosage formulation that contains a compound having the general structure of Formula I and one or more additional active agents, as well as administration of a compound of Formula I and each active agent in its own separate pharmaceutical dosage formulation. For example, a compound of Formula I and a DPPIV inhibitor can be administered to the human subject together in a single oral dosage composition, such as a tablet or capsule, or each agent can be administered in separate oral dosage formulations. Where separate dosage formulations are used, a compound of Formula I and one or more additional active agents can be administered at essentially the same time (i.e., concurrently), or at separately staggered times (i.e., sequentially). Combination therapy is understood to include all these regimens.

An example of combination therapy can be seen in modulating (preventing the onset of the symptoms or complications associated with) diabetes (or treating, preventing or reducing the risk of developing, diabetes and its related symptoms, complications, and disorders), wherein the compounds of Formula I can be effectively used in combination with, for example, biguanides (such as metformin); thiazolidinediones (such as ciglitazone, pioglitazone, troglitazone, and rosiglitazone); dipeptidyl-peptidase-4 ("DPPIV") inhibitors (such as vildagliptin and sitagliptin); glucagonlike peptide-1 ("GLP-1") receptor agonists (such as exanatide) (or GLP-1 mimetics); PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, $DHEA-SO_4$); antiglucocorticoids; $TNF\alpha$ inhibitors; $\alpha$-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretogogues (such as repaglinide, gliquidone, and nateglinide); insulin (or insulin mimetics); glucagon receptor antagonists; gastric inhibitory peptide ("GIP"); or GIP mimetics; as well as the active agents discussed below for treating obesity, hyperlipidemia, atherosclerosis and/or metabolic syndrome.

Another example of combination therapy can be seen in treating obesity or obesity-related disorders, wherein the compounds of Formula I can be effectively used in combination with, for example, phenylpropanolamine, phenteramine; diethylpropion; mazindol; fenfluramine; dexfenfluramine; phentiramine, β-3 adrenoceptor agonist agents; sibutramine; gastrointestinal lipase inhibitors (such as orlistat); and leptins. Other agents used in treating obesity or obesity-related disorders wherein the compounds of Formula I can be effectively used in combination with, for example, cannabinoid-1

("CB-1") receptor antagonists (such as rimonabant); PPAR delta agonists or partial agonists; dual PPAR alpha, PPAR delta agonists or partial agonists; dual PPAR delta, PPAR gamma agonists or partial agonists; pan PPAR agonists or partial agonists; neuropeptide Y; enterostatin; cholecytokinin; bombesin; amylin; histamine $H_3$ receptors; dopamine $D_2$ receptors; melanocyte stimulating hormone; corticotrophin releasing factor; galanin; and gamma amino butyric acid (GABA).

Still another example of combination therapy can be seen in modulating hyperlipidemia (treating hyperlipidemia and its related complications), wherein the compounds of Formula I can be effectively used in combination with, for example, statins (such as atorvastatin, fluvastatin, lovastatin, pravastatin, and simvastatin), CETP inhibitors (such as torcetrapib); a cholesterol absorption inhibitor (such as ezetimibe); PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; fenofibric acid derivatives (such as gemfibrozil, clofibrate, fenofibrate, and bezafibrate); bile acid-binding resins (such as colestipol or cholestyramine); nicotinic acid; probucol; betacarotene; vitamin E; or vitamin C.

A further example of combination therapy can be seen in modulating atherosclerosis, wherein a compound of Formula I is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin); an HMG-CoA synthase inhibitor; a squalene epoxidase inhibitor; or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide); anti-oxidant vitamins, such as vitamin C and E and beta carotene; a β-blocker; an angiotensin II antagonist; an angiotensin converting enzyme inhibitor; PPAR alpha agonists or partial agonists; PPAR delta agonists or partial agonists; PPAR gamma agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; and a platelet aggregation inhibitor, such as fibrinogen receptor antagonists (i.e., glycoprotein IIb/IIIa fibrinogen receptor antagonists) and aspirin. As noted above, the compounds of Formula I can be administered in combination with more than one additional active agent, for example, a combination of a compound of Formula I with an HMG-CoA reductase inhibitor (e.g., atorvastatin, fluvastatin, lovastatin, pravastatin, and simvastatin) and aspirin, or a compound of Formula I with an HMG-CoA reductase inhibitor and a β-blocker.

Additionally, an effective amount of a compound of Formula I and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor; an HMG-CoA synthase inhibitor; a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; CETP inhibitors such as torcetrapib; a cholesterol absorption inhibitor such as ezetimibe; PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; niacinamide; a cholesterol absorption inhibitor; a bile acid sequestrant anion exchange resin; a LDL receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, β-3 adrenergic receptor agonists; sulfonylureas, biguanides, α-glucosidase inhibitors, other insulin secretogogues, and insulin can be used together for the preparation of a pharmaceutical composition useful for the above-described treatments.

An additional example of combination therapy can be seen in modulating metabolic syndrome (or treating metabolic syndrome and its related symptoms, complications and disorders), wherein the compounds of Formula I can be effectively used in combination with, for example, the active agents discussed above for modulating or treating diabetes, obesity, hyperlipidemia, atherosclerosis, and/or their respective related symptoms, complications and disorders.

In a further embodiment, a compound of the present invention can be administered in combination with halofenic acid, an ester of halofenic acid, or another prodrug of halofenic acid, preferably with (−)-(4-chlorophenyl)-(3-trifluoromethylphenoxy)-acetic acid 2-acetylaminoethyl ester.

Methods of Diagnosis and/or Imaging

Compounds of the present invention are also useful in methods of diagnosis and/or imaging. Many direct methods are available to evaluate an agent's biodistribution in the body such as magnetic resonance imaging ("MRI"), positron emission tomography ("PET"), and single photon emission computed tomography ("SPECT"). Each of these methods can detect the distribution of a compound within the body if that compound contains an atom with the appropriate nuclear properties. MRI detects paramagnetic nuclei; PET and SPECT detect the emission of particles from the decay of radionuclei.

Most therapeutic agents are not able to be detected by these techniques without modification. Thus, for PET it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K F Hubner, et al., Chapter 2). Another useful isotope, $^{18}F$, has a half-life of 110 minutes. This allows sufficient time for incorporation into a radiolabeled tracer, for purification and for administration into a human or animal subject. $^{18}$F labeled compounds have been used in studies of glucose metabolism and localization of glucose uptake associated with brain activity. For example, $^{18}$F-L-fluorodopa and other dopamine receptor analogs have also been used in mapping dopamine receptor distribution.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $^{123}$I, a γ-emitter with a 13.3 hour half life. Compounds labeled with $^{123}$I can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs.

In the context of the present invention, methods are provided for diagnosing a disease or condition selected from Type I diabetes and Type II diabetes, the method comprising
(a) administering to a subject having, or at risk for, such a disease or condition an imaging amount of a compound of the invention, wherein the compound is isotopically labeled; and
(b) imaging the subject to determine the number, mass or volume of pancreatic beta cells or islet endocrine cells; or to assess the function of pancreatic beta cells or islet endocrine cells.

Preferably, the compound is labeled with $^{11}$C or $^{14}$C. In other preferred embodiments, the imaging is conducted via PET or SPECT.

Kits

In addition, the present invention provides for kits with unit doses of the compounds of Formula I, either in oral or injectable doses. In addition to the containers containing the unit doses will be an informational package insert describing the use and attendant benefits of the drugs in treating Type II diabetes, obesity, hyperlipidemia, atherosclerosis and metabolic syndrome, and/or their respective related symptoms, complications and disorders. Preferred compounds and unit doses are those described herein above.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXAMPLES

General Methods. All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on E. Merck silica gel 60 (240-400 mesh) according to the protocol of Still, Kahn, and Mitra (J. Org. Chem. 1978, 43, 2923). Thin layer chromatography was performed using precoated plates purchased from E. Merck (silica gel 60 PF$_{254}$, 0.25 mm) and spots were visualized with long-wave ultraviolet light followed by an appropriate staining reagent.

Nuclear magnetic resonance ("NMR") spectra were recorded on a Varian Inova-400 resonance spectrometer. $^1$H NMR chemical shifts are given in parts per million (δ) downfield from tetramethylsilane ("TMS") using TMS or the residual solvent signal (CHCl$_3$=δ 7.24, DMSO=δ 2.50) as internal standard. $^1$H NMR information is tabulated in the following format: number of protons, multiplicity (s, singlet; d, doublet; t, triplet; q, quartet; m, multiplet), coupling constant(s) (J) in Hertz, and, in selected cases, position assignment. The prefix app is occasionally applied in cases where the true signal multiplicity was unresolved and br indicates the signal in question was broadened.

The compounds were named using ChemBioDraw Ultra Version 11.0.

LCMS analysis was performed using a PE SCIEX API 2000 spectrometer with a Phenomenex Luna 5 micron C$_{18}$ column.

The compounds of the present invention can be prepared by methodology in the Reaction Scheme below, and with specific reagents and conditions provided in each of the examples below.

Reaction Schemes

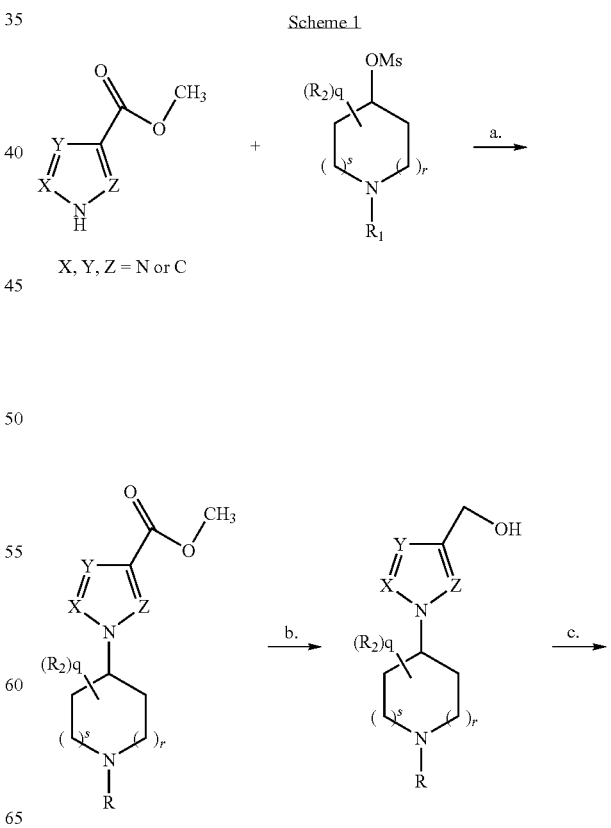

-continued

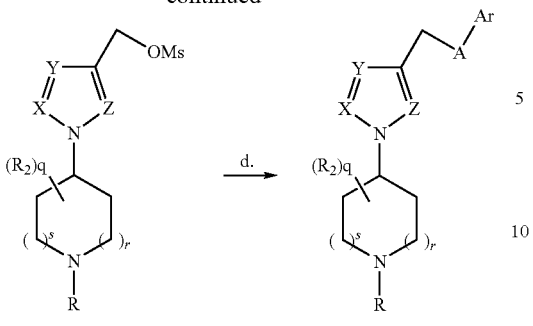

Reagents and conditions: a. DMF, 90° C., 72 h; b. LiAlH₄, THF; c. MsCl, NEt₃, CH₂Cl₂; d. CsCO₃, HA-Ar, CH₃CN, 82° C., 4 h.

Scheme 2

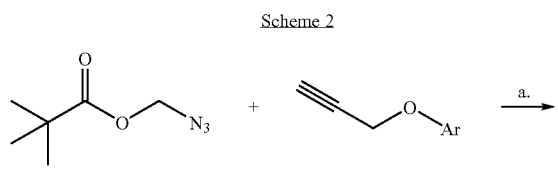

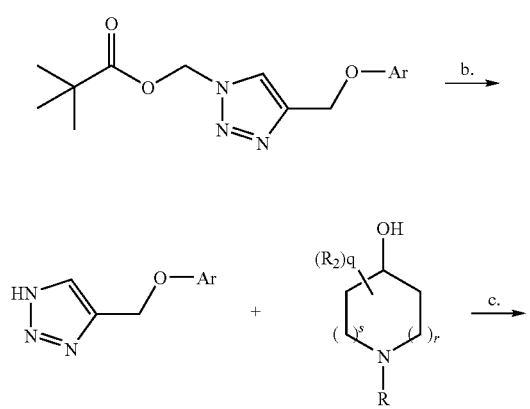

Reagents and conditions: a. sodium ascorbate, cat. CuSO₄, ᵗBuOH/H₂O (1:1 v/v), 72 h, rt; b. NaOH, 10:1 MeOH/THF, 1-4 h; c. PPh₃, DIAD, THF, 0° C.-rt, 4 h.

Preparation of Intermediate 1: 4-(3-Methanesulfonyloxymethyl-[1,2,4]triazol-1-yl)-piperidine-1-carboxylic acid tert-butyl ester

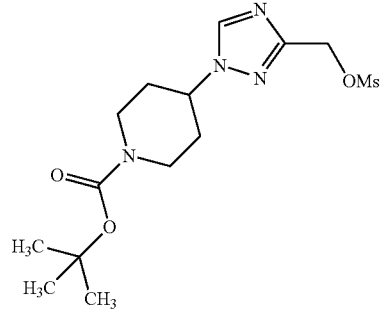

Step 1: 4-(3-Methoxycarbonyl-[1,2,4]triazol-1-yl)-piperidine-1-carboxylic acid tert-butyl ester

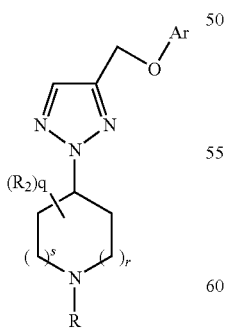

To a solution of 1H-[1,2,4]triazole-3-carboxylic acid ethyl ester (1.05 g, 8.23 mmol) in dimethylformamide (50 mL) was added sodium hydride (60%, 0.395 g, 9.88 mmol). The solution was stirred at room temperature for 20 minutes followed by 1 hour at 70° C. 4-methanesulfonyloxy-piperidine-1-carboxylic acid tert-butyl ester (2.3 g, 8.23 mmol) was then added in a single portion and heated at 70° C. for 40 hours. The solution was cooled to 0° C. and the salt precipitate was removed by filtration. The filtrate was diluted with dichloromethane and washed with water, brine, dried over sodium sulfate, filtered and concentrated in vacuo. The residue was purified by flash chromatograph on silica gel with Hexanes and EtOAc to afford the desired product. ¹H NMR (CDCl₃): δ 8.18 (1H, s), 4.40 (1H, m), 4.22 (2H, m), 3.96 (3H, s), 2.82 (2H, m), 2.12 (2H, m), 1.94 (2H, m), 1.41 (9H, s).

Step 2: 4-(3-Hydroxymethyl-[1,2,4]triazol-1-yl)-piperidine-1-carboxylic acid tert-butyl ester

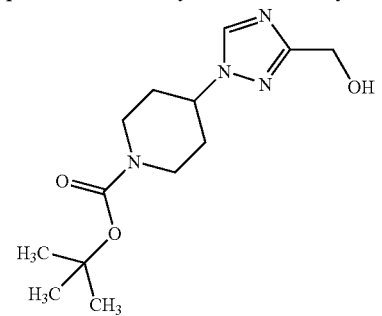

To a solution of 4-(3-ethoxycarbonyl-[1,2,4]triazol-1-yl)-piperidine-1-carboxylic acid tert-butyl ester (from Step 1, 0.64 g, 2.06 mmol) in THF (10 mL) at 0° C. was added lithium aluminum hydride (0.078 g, 2.06 mmol). The solution was allowed to warm to room temperature and stirred for 4 hours. The solution was diluted with THF, cooled to 0° C., and 1 mL of water was added followed by 1 mL of 15% NaOH and 3 mL of water. The solution was allowed to warm to room temperature and stirred for 15 minutes. MgSO$_4$ was then added and the solution was stirred an additional 15 minutes, filtered and concentrated in vacuo. The residue was purified by flash chromatograph on silica gel with MeOH and CH$_2$Cl$_2$ to afford the desired product. $^1$H NMR (CDCl$_3$): δ 8.03 (1H, s), 4.79 (2H, d), 4.25 (3H, m), 2.95 (2H, m), 2.58 (1H, t), 2.19 (2H, m), 1.98 (2H, m), 1.43 (9H, s).

Step 3: 4-(3-Methanesulfonyloxymethyl-[1,2,4]triazol-1-yl)-piperidine-1-carboxylic acid tert-butyl ester

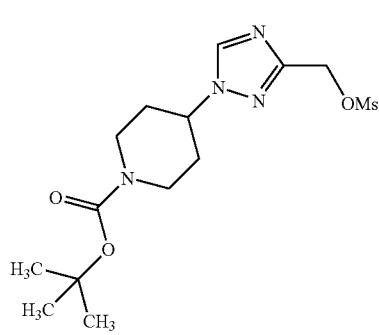

To a solution of 4-(3-hydroxymethyl-[1,2,4]triazol-1-yl)-piperidine-1-carboxylic acid tert-butyl ester (from Step 2 above, 0.181 g, 0.641 mmol) and triethylamine (0.134 mL, 0.961 mmol) in dichloromethane (5 mL) at 0° C. was added methanesulfonylchloride (0.055 mL, 0.705 mmol). The resulting solution was stirred at room temperature for 1 hour. The solvent was removed in vacuo to yield the desired product as a light yellow oil that was used without further purification.

Preparation of Intermediate 2: 4-(4-Methanesulfonyloxymethyl-[1,2,3]triazol-2-yl)-piperidine-1-carboxylic acid tert-butyl ester

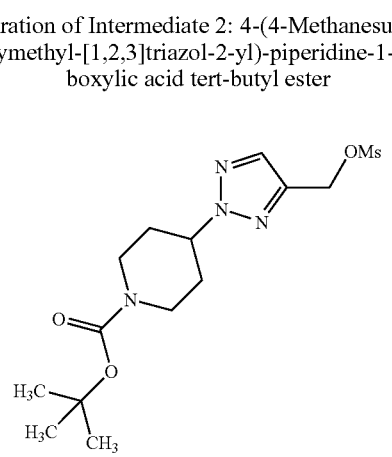

Intermediate 2 was prepared manner similar to that described in Intermediate 1 above from 1,2,3-triazole-4-carboxylic acid methyl ester which can be prepared from azidotrimethylsilane and methyl propiolate as described in patent EP1422228 A1.

Preparation of Intermediate 3: 4-(4-Methanesulfonyloxymethyl-pyrazol-1-yl)-piperidine-1-carboxylic acid tert-butyl ester

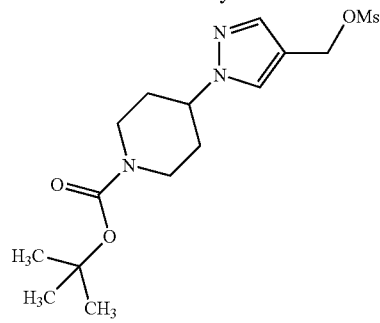

Intermediate 3 was prepared manner similar to that described in Intermediate 1 above from commercial available ethyl 4-pyrazolecarboxylate.

Preparation of Intermediate 4: 4-(3-Methanesulfonyloxymethyl-pyrazol-1-yl)-piperidine-1-carboxylic acid tert-butyl ester

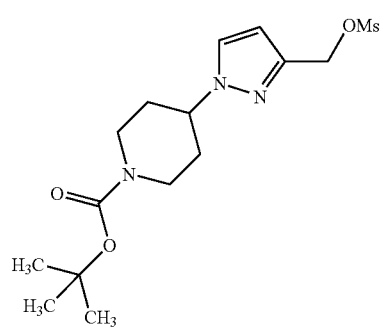

Intermediate 4 was prepared manner similar to that described in Intermediate 1 above from 1H-pryazole-3-carboxylic acid methyl ester which was prepared from commercial available 1H-pryazole-3-carboxylic acid.

Preparation of Intermediate 5: 4-(5-Methanesulfonyloxymethyl-tetrazol-2-yl)-piperidine-1-carboxylic acid tert-butyl ester

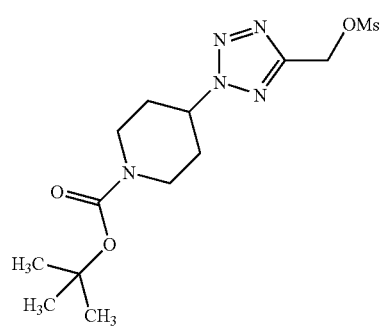

Intermediate 5 was prepared manner similar to that described in Intermediate 1 above from commercially available 1H-tetrazole-5-carboxylic acid ethyl ester sodium salt.

Preparation of Intermediate 6: 4-[3-(2-Fluoro-4-methanesulfonyl-phenoxymethyl)-[1,2,4]triazol-1-yl]-piperidine hydrochloride

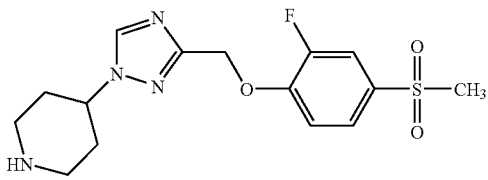

A solution of 4-[3-(2-fluoro-4-methanesulfonyl-phenoxymethyl)-[1,2,4]triazol-1-yl]-piperidine-1-carboxylic acid tert-butyl ester (see Example 1, 0.249 g, 2.74 mmol) in methanol (10 mL) was treated with 10 mL of 4N HCl in dioxane. The resulting solution was stirred at room temperature for 30 minutes and the solvent was removed in vacuo to afford the desired product as an HCl salt which was used without further purification.

Preparation of Intermediate 7: 4-[4-(2-Fluoro-4-methanesulfonyl-phenoxymethyl)-[1,2,3]triazol-2-yl]-piperidine hydrochloride

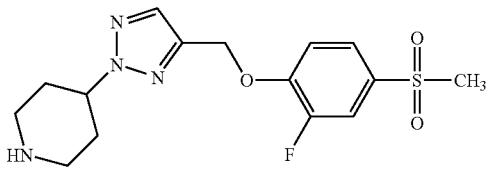

Intermediate 7 was prepared manner similar to that described in Intermediate 6.

Preparation of Intermediate 8: 4-[4-(2-Fluoro-4-tetrazol-1-yl-phenoxymethyl)-[1,2,3]triazol-2-yl]-piperidine hydrochloride

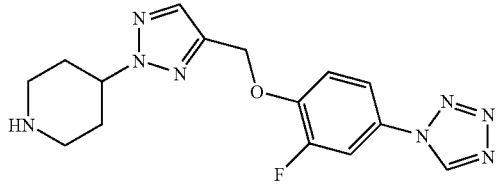

Intermediate 8 was prepared manner similar to that described in Intermediate 6

Preparation of Intermediate 9: 4-[4-(4-Tetrazol-1-yl-phenoxymethyl)-[1,2,3]triazol-2-yl]-piperidine hydrochloride

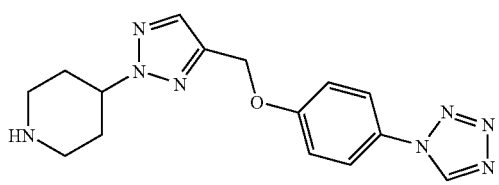

Intermediate 9 was prepared manner similar to that described in Intermediate 6.

Preparation of Intermediate 10: 4-[5-(2-Fluoro-4-methanesulfonyl-phenoxymethyl)-tetrazol-2-yl]-piperidine hydrochloride

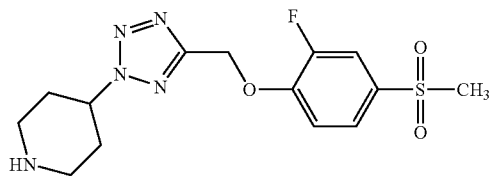

Intermediate 10 was prepared in a manner similar to that described in Intermediate 6 using.

Preparation of Intermediate 11: 4-[4-(2-Fluoro-4-tetrazol-1-yl-phenoxymethyl)-pyrazol-1-yl]-piperidine hydrochloride

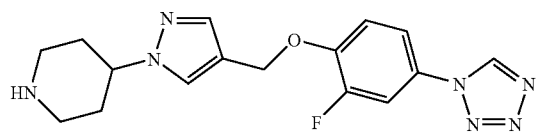

Intermediate 11 was prepared in a manner similar to that described in Intermediate 6.

Preparation of Intermediate 12: 4-[4-(4-Tetrazol-1-yl-phenoxymethyl)-pyrazol-1-yl]-piperidine hydrochloride

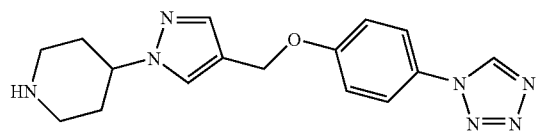

Intermediate 12 was prepared in a manner similar to that described in Intermediate 6.

Preparation of Intermediate 13: 5-((2H-1,2,3-Triazol-4-yl)methoxy)-2-(1H-tetrazol-1-yl)pyridine

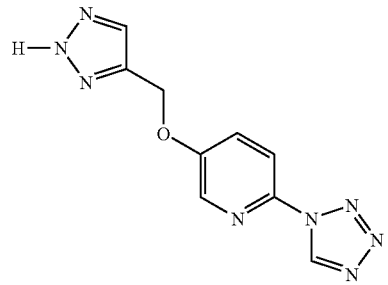

Step 1: 6-(1H-Tetrazol-1-yl)pyridin-3-ol

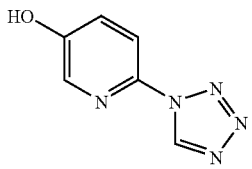

NaN₃ (2.89 g, 44 mmol) and triethylorthoformate (7.4 ml, 44 mmol) were added to commercially available 6-aminopyridin-3-ol (3.5 g, 32 mmol) in AcOH (50 mL). The reaction mixture was heated to 100° C. for 1-3 hours. The reaction was cooled to room temperature and left to stand overnight. The precipitate was filtered, washed with EtOAc (150 mL) and dried in vacuo. The crude product was obtained as a beige solid and used in the next step without further purification.

Step 2: 5-(Prop-2-ynyloxy)-2-(1H-tetrazol-1-yl)pyridine

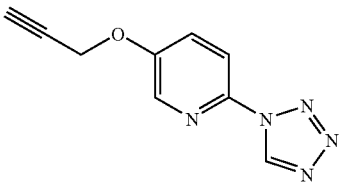

To a flask under N₂ fitted with a reflux condenser was added 6-tetrazol-1-yl-pyridin-3-ol (2.25 g, 13.7 mmol) and N,N-dimethylformamide (8.2 mL). Potassium carbonate (3.79 g, 27.4 mmol, 2 eq.), potassium iodide (0.143 g, 0.86 mmol, 0.06 eq.) and propargyl chloride (1.98 mL, 17.9 mmol, 1.3 eq.) were added and heated at 80° C. for three hours. The reaction was cooled to room temperature and 10 mL of water was added to affect precipitation. The solid was filtered off, washed with water and dried overnight. The expected product was used in the next step without further purification. $^1$H NMR (DMSO-$d_6$): δ 10.08 (1H, s), 8.36 (1H, d, J=3.0 Hz), 8.01 (1H, d, J=9 Hz), 7.79 (1H, dd, J=3.0, 9.0 Hz), 5.01 (2H, s), 3.71 (1H, s).

Step 3: (4-((6-(1H-Tetrazol-1-yl)pyridin-3-yloxy)methyl)-1H-1,2,3-triazol-1-yl)methyl pivalate

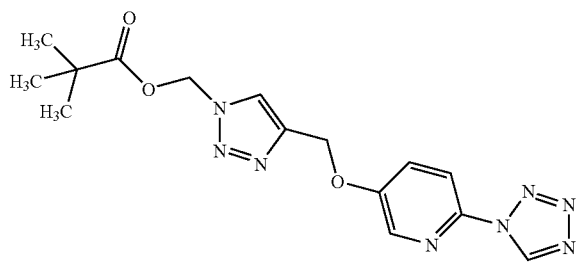

To a solution of azidomethyl pivalate (4.26 g, 27.1 mmol) in 1:1 tert-butanol water (90 mL total) was added 5-(prop-2-ynyloxy)-2-(1H-tetrazol-1-yl)pyridine (5.45 g, 27.1 mmol), sodium ascorbate (1.4 mL of a 1M solution in water) and copper sulfate (1.4 mL of a 1M solution in water). The solution was stirred at room temperature for 72 hours. Water was added and the suspension was extracted with ethyl acetate. The organic layer was separated, dried over sodium sulfate, filtered and concentrated in vacuo to afford the expected product which was used in the next step without further purification. $^1$H NMR (DMSO-$d_6$): δ 10.07 (1H, s), 8.43-8.41 (2H, m), 8.00 (1H, d, J=8.8 Hz), 7.88 (1H, dd, J=3.2, 8.8 Hz), 6.32 (2H, s), 5.38 (2H, s), 1.08 (9H, s).

Step 4: 5-((2H-1,2,3-Triazol-4-yl)methoxy)-2-(1H-tetrazol-1-yl)pyridine

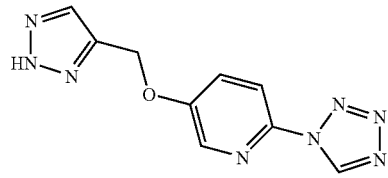

To a solution of (4-((6-(1H-tetrazol-1-yl)pyridin-3-yloxy)methyl)-1H-1,2,3-triazol-1-yl)methyl pivalate (10 g, 27.9 mmol) in MeOH (60 mL) and THF (6 mL) was added sodium hydroxide (61.5 mL of a 1M solution in water). The mixture was stirred for 30 minutes and hydrochloric acid was added (61.5 mL of a 1M solution in water). The resulting solution was extracted with ethyl acetate, separated, dried over sodium sulfate, filtered and concentrated in vacuo to afford the expected product which was used in subsequent steps without further purification. $^1$H NMR (DMSO-$d_6$): δ 10.07 (1H, s), 8.43-8.41 (2H, m), 8.00 (1H, d, J=8.8 Hz), 7.88 (1H, dd, J=3.2, 8.8 Hz), 6.32 (2H, s), 5.38 (2H, s), 1.08 (9H, s).

Preparation of Intermediate 14: 1-(3-cyclopropyl-1,2,4-oxadiazol-5-yl)piperidin-4-ol

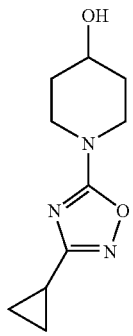

The title compound was synthesized in a manner similar to that described in WO2008/008887 A2, example 16, page 84.

Preparation of Intermediate 15: 5-((2-(Piperidin-4-yl)-2H-1,2,3-triazol-4-yl)methoxy)-2-(1H-tetrazol-1-yl)pyridine hydrochloride

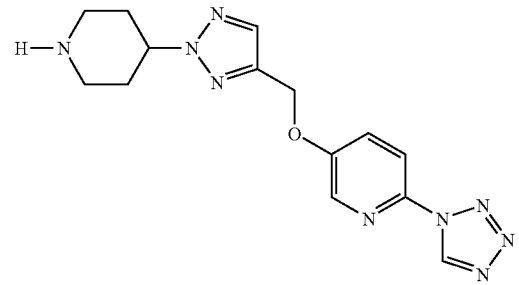

Intermediate 15 was prepared in a manner similar to that described in Intermediate 6.

Preparation of Intermediate 16: 1-(4-((2H-1,2,3-Triazol-4-yl)methoxy)-3-fluorophenyl)-1H-tetrazole

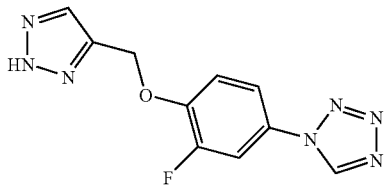

This intermediate was synthesized from commercially available 4-amino-2-fluorophenol in a manner similar to that described for Intermediate 13 above.

Preparation of Intermediate 17: cis-1-(5-Ethylpyrimidin-2-yl)-3-fluoropiperidin-4-ol

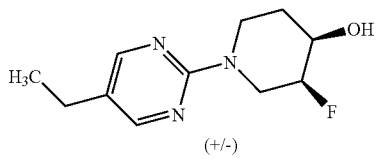
(+/-)

Step 1: 1-(5-Ethylpyrimidin-2-yl)piperidin-4-one

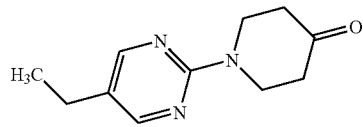

The title compound was synthesized from piperidin-4-one and 2-chloro-5-ethylpyrimidine manner similar to that described in Example 9.

Step 2: cis-1-(5-Ethylpyrimidin-2-yl)-3-fluoropiperidin-4-ol

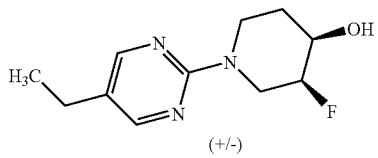
(+/-)

The title compound was synthesized from piperidin-4-one and 2-chloro-5-ethylpyrimidine in a manner similar to that described in *J. Med. Chem.* 1998, 41, 2667-2670.

Preparation of Intermediate 18: cis-tert-Butyl 3-fluoro-4-hydroxypiperidine-1-carboxylate

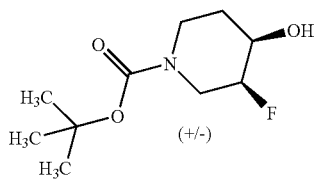
(+/-)

The title compound was synthesized as described in *J. Med. Chem.* 1998, 41, 2667-2670.

Preparation of Intermediate 19: trans-3-Fluoro-4-(4-((2-fluoro-4-(1H-tetrazol-1-yl)phenoxy)methyl)-2H-1,2,3-triazol-2-yl)piperidine hydrochloride

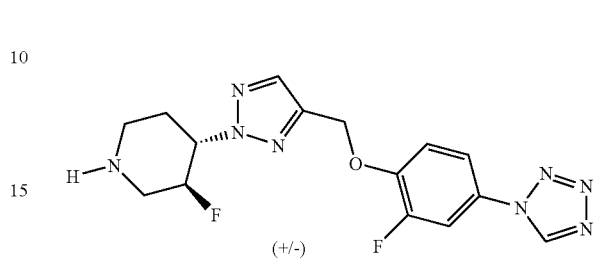
(+/-)

Intermediate 19 was prepared in a manner similar to that described in Intermediate 6.

Preparation of Intermediate 20: 1-(5-(Trifluoromethyl)pyrimidin-2-yl)piperidin-4-ol

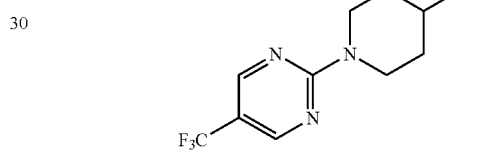

To a solution of 4-hydroxypiperidine (6.18 g, 61 mmol), and potassium carbonate (11.0 g, 80 mmol) in N,N dimethylformamide (150 mL) was added 2-(methylsulfonyl)-5-(trifluoromethyl)pyrimidine (12.3 g, 54 mmol) and stirred at room temperature for 18 h. To the reaction mixture was added 300 mL of water and the heterogeneous mixture was stirred for an additional 10 minutes. The white solid was filtered and washed with water to afford the desired product.

Preparation of Intermediate 21: 5-((2-(3-Methylpiperidin-4-yl)-2H-1,2,3-triazol-4-yl)methoxy)-2-(1H-tetrazol-1-yl)pyridine

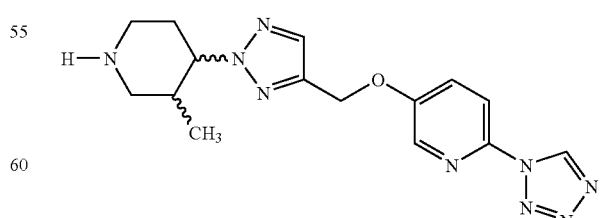

Intermediate 21 was prepared in a manner similar to that described in Intermediate 6 above in a mixture of four stereoisomers.

Preparation of Intermediate 22:
1-(5-Chloropyrimidin-2-yl)piperidin-4-ol

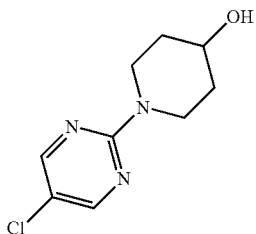

Intermediate 22 was prepared from 2,5-dichloropyrimidine and 4-hydroxypiperidine in a manner similar to that described in Intermediate 20.

Preparation of Intermediate 23:
1-(5-Chloropyrimidin-2-yl)piperidin-4-yl methanesulfonate

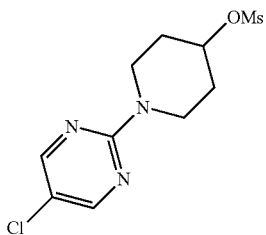

Intermediate 23 was prepared from Intermediate 22 in a manner similar to that described in Intermediate 1, Step 3.

Preparation of Intermediate 24: (2-(1-(5-Chloropyrimidin-2-yl)piperidin-4-yl)-2H-1,2,3-triazol-4-yl)methyl methanesulfonate

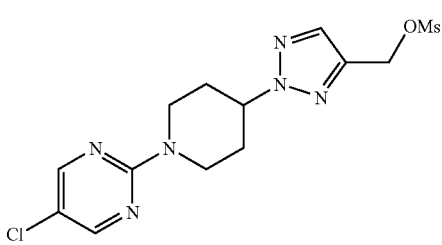

Intermediate 24 was prepared from 1-(5-chloropyrimidin-2-yl)piperidin-4-yl methanesulfonate (Intermediate 23) and 1,2,3-triazole-4-carboxylic acid methyl ester (prepared from azidotrimethylsilane and methyl propiolate as described in patent EP1422228 A1) in a manner similar to that described in Intermediate 1.

Preparation of Intermediate 25: 1-(5-(Trifluoromethyl)pyrimidin-2-yl)piperidin-4-yl methanesulfonate

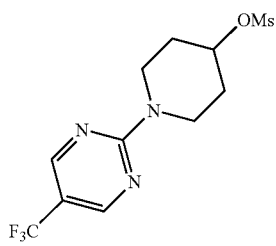

Intermediate 25 was prepared from Intermediate 20 in a manner similar to that described in Intermediate 1, Step 3.

Preparation of Intermediate 26: (2-(1-(5-(Trifluoromethyl)pyrimidin-2-yl)piperidin-4-yl)-2H-1,2,3-triazol-4-yl)methyl methanesulfonate

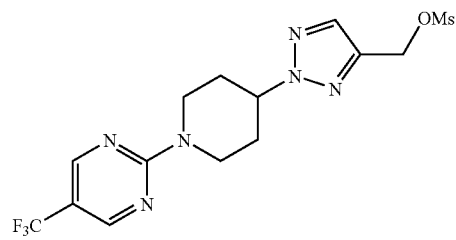

Intermediate 26 was prepared from 1-(5-(trifluoromethyl)pyrimidin-2-yl)piperidin-4-yl methanesulfonate (Intermediate 25) and 1,2,3-triazole-4-carboxylic acid methyl ester (prepared from azidotrimethylsilane and methyl propiolate as described in patent EP1422228 A1) in a manner similar to that described in Intermediate 1.

Preparation of Intermediate 27: (2-(1-(5-(Trifluoromethyl)pyrimidin-2-yl)piperidin-4-yl)-2H-1,2,3-triazol-4-yl)methanol

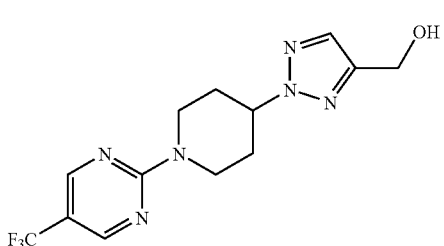

Intermediate 27 was prepared from 1-(5-(trifluoromethyl)pyrimidin-2-yl)piperidin-4-yl methanesulfonate (Intermediate 25) and 1,2,3-triazole-4-carboxylic acid methyl ester (prepared from azidotrimethylsilane and methyl propiolate as described in patent EP1422228 A1) in a manner similar to that described in Intermediate 1 through Step 2.

Preparation of Intermediate 28: 1-(5-Ethylpyrimidin-2-yl)piperidin-4-ol

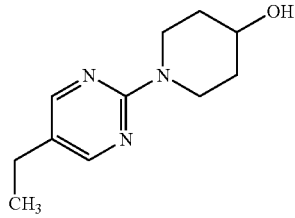

Intermediate 28 was prepared from 2-chloro-5-ethylpyrimidine and 4-hydroxypiperidine in a manner similar to that described in Intermediate 20.

Preparation of Intermediate 29: 1-(5-Ethylpyrimidin-2-yl)piperidin-4-yl methanesulfonate

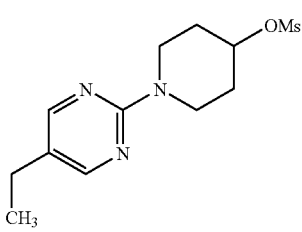

Intermediate 29 was prepared from Intermediate 28 in a manner similar to that described in Intermediate 1, Step 3.

Preparation of Intermediate 30: (2-(1-(5-Ethylpyrimidin-2-yl)piperidin-4-yl)-2H-1,2,3-triazol-4-yl) methyl methanesulfonate

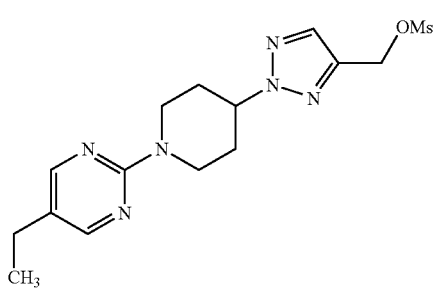

Intermediate 30 was prepared from 1-(5-ethylpyrimidin-2-yl)piperidin-4-yl methanesulfonate (Intermediate 29) and 1,2,3-triazole-4-carboxylic acid methyl ester (prepared from azidotrimethylsilane and methyl propiolate as described in patent EP1422228A1) in a manner similar to that described in Intermediate 1.

Preparation of Intermediate 31: 4-(3-((2-fluoro-4-(1H-tetrazol-1-yl)phenoxy)methyl)-1H-pyrazol-1-yl)piperidine hydrochloride

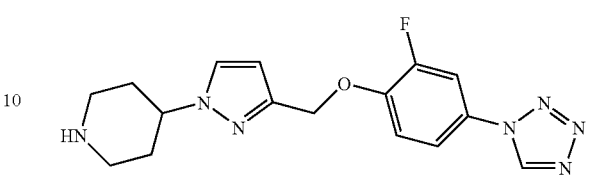

Intermediate 31 was prepared in a manner similar to that described in Intermediate 6.

Example 1

4-[3-(2-Fluoro-4-methanesulfonyl-phenoxymethyl)-[1,2,4]triazol-1-yl]-piperidine-1-carboxylic acid tert-butyl ester

A mixture of 4-(3-methanesulfonyloxymethyl-[1,2,4]triazol-1-yl)-piperidine-1-carboxylic acid tert-butyl ester (Intermediate 1, 0.222 g, 0.641 mmol), 2-Fluoro-4-methanesulfonyl-phenol (0.122 g, 0.641 mmol) and $CsCO_3$ (0.250 g, 0.769 mmol) in acetonitrile (10 mL) was heated under reflux for 4 hours. After cooling, the solution was filtered through a pad of celite and the solvent was removed in vacuo. The residue was purified by flash chromatography on silica gel with Hexanes and EtOAc to afford the desired product. $^1$H NMR ($CDCl_3$): δ 8.15 (1H, s), 7.62 (2H, m), 7.37 (1H, m), 5.25 (2H, s), 4.25 (3H, m), 3.05 (3H, s), 2.85 (2H, m), 2.18 (2H, m), 1.97 (2H, m), 1.43 (9H, s).

The compounds in Examples 2-8 were synthesized from one of Intermediates 2-5 with the corresponding phenol in a manner similar to that described in Example 1. One skilled in the art of organic synthesis will appreciate that conditions such as solvent (DMF, $CH_3CN$), temperature, base ($NEt_3$, $^iPr_2NEt$, $K_2CO_3$, $NaHCO_3$, $Na_2CO_3$, $Cs_2CO_3$) and concentration can be selected through routine experimentation to optimize yields. Additionally, alternative coupling methods can be used that are well known in the art of organic synthesis.

Example 2

4-[4-(2-Fluoro-4-tetrazol-1-yl-phenoxymethyl)-[1,2,3]triazol-2-yl]-piperidine-1-carboxylic acid tert-butyl ester

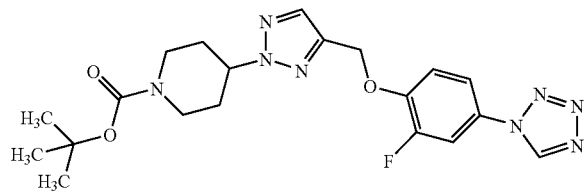

¹H NMR (CDCl₃): δ 8.92 (1H, s), 7.72 (1H, s), 7.52 (1H, d), 7.42 (1H, d), 7.31 (1H, m), 5.30 (2H, s), 4.61 (1H, m), 4.20 (2H, m), 2.99 (2H, m), 2.16-2.08 (4H, m), 1.48 (9H, s).

Example 3

4-[4-(4-Tetrazol-1-yl-phenoxymethyl)-[1,2,3]triazol-2-yl]-piperidine-1-carboxylic acid tert-butyl ester

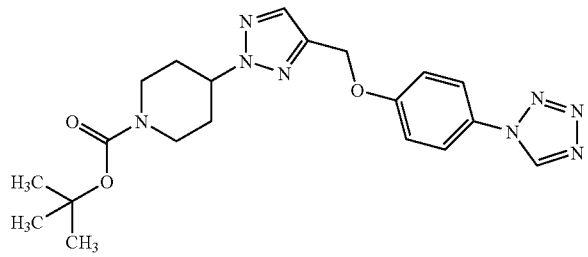

¹H NMR (CDCl₃): δ 8.98 (1H, s), 7.7 (1H, s), 7.64 (2H, m), 7.18 (2H, m), 5.23 (2H, s), 4.63 (1H, m), 4.2 (2H, m), 3 (2H, m), 2.22-2.08 (4H, m), 1.48 (9H, s).

Example 4

4-[4-(2-Fluoro-4-methanesulfonyl-phenoxymethyl)-[1,2,3]triazol-2-yl]-piperidine-1-carboxylic acid tert-butyl ester

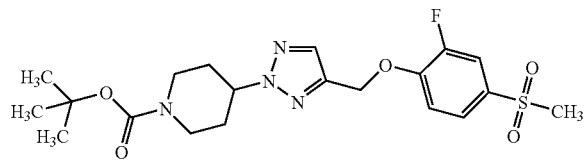

¹H NMR (CDCl₃): δ 7.73-7.65 (3H, m), 7.27 (1H, m), 5.3 (2H, s), 4.61 (1H, m), 4.2 (2H, m), 3.05 (3H, m), 2.95 (2H, m), 2.2-2.1 (4H, m), 1.48 (9H, s).

Example 5

4-[5-(2-Fluoro-4-methanesulfonyl-phenoxymethyl)-tetrazol-2-yl]-piperidine-1-carboxylic acid tert-butyl ester

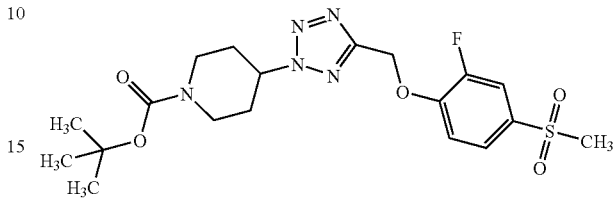

¹H NMR (CDCl₃): δ 7.72-7.62 (2H, m), 7.33 (1H, t), 5.46 (2H, s), 4.87 (1H, m), 4.2 (2H, m), 3.03 (3H, s), 2.95 (2H, m), 2.35-2.1 (4H, m), 1.46 (9H, s).

Example 6

4-[3-(2-Fluoro-4-tetrazol-1-yl-phenoxymethyl)-pyrazol-1-yl]-piperidine-1-carboxylic acid tert-butyl ester

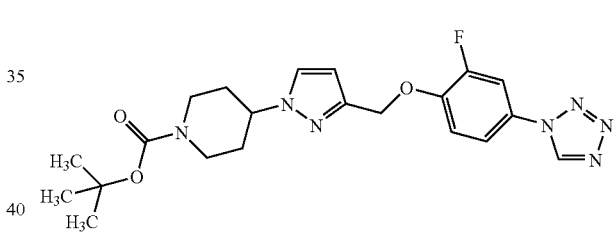

¹H NMR (CDCl₃): δ 8.79 (1H, s), 7.28~7.36 (4H, m), 6.24 (1H, s), 5.08 (2H, s), 4.11 (3H, m), 2.74 (2H, m), 1.97 (2H, m), 1.77 (2H, m), 1.36 (9H, s).

Example 7

4-[4-(2-Fluoro-4-tetrazol-1-yl-phenoxymethyl)-pyrazol-1-yl]-piperidine-1-carboxylic acid tert-butyl ester

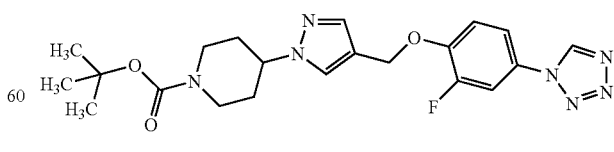

¹H NMR (CDCl₃): δ 8.92 (1H, s), 7.59 (1H, s), 7.55 (1H, s), 7.50 (1H, m), 7.42 (1H, m), 7.20 (1H, m), 5.10 (2H, s), 4.25 (3H, m), 2.87 (2H, m), 2.12 (2H, m), 1.89 (2H, m), 1.46 (9H, s).

Example 8

4-[4-(4-Tetrazol-1-yl-phenoxymethyl)-pyrazol-1-yl]-piperidine-1-carboxylic acid tert-butyl ester

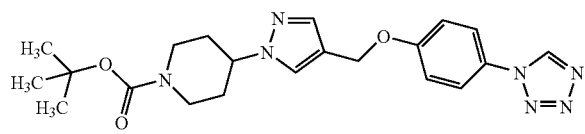

¹H NMR (CDCl₃): δ 8.92 (1H, s), 7.60 (3H, m), 7.54 (1H, s), 7.11 (1H, m), 5.02 (2H, s), 4.25 (3H, m), 2.87 (2H, m), 2.12 (2H, m), 1.88 (2H, m), 1.46 (9H, s).

tion in vacuo. The residue was chromatographed on silica gel (1:1 Hex/EtOAc) to afford the desired product. ¹H NMR (CDCl₃): δ 8.22 (2H, s), 8.17 (1H, s), 7.68 (2H, m), 7.38 (1H, m), 5.28 (2H, s), 4.92 (2H, d), 4.47 (1H, m), 3.08 (3H, s), 2.94 (2H, m), 2.48 (2H, q), 2.27 (1H, m), 2.18 (1H, m), 1.98 (2H, m), 1.20 (3H, t).

The compounds in Examples 10-20 were synthesized from one of Intermediates 7-12 with the corresponding substituted 2-fluoropyrimidine, 2-chloropyrimidine, 2-bromopyrimidine, 2-iodopyrimidine, 2-(methylsulfinyl)pyrimidine or 2-(methylsulfonyl)pyrimidine in a manner similar to that described in Example 9. One skilled in the art of organic synthesis will appreciate that conditions such as solvent (DMF, CH₃CN), temperature, base (NEt₃, ⁱPr₂NEt, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 9

5-Ethyl-2-{4-[3-(2-fluoro-4-methanesulfonyl-phenoxymethyl)-[1,2,4]triazol-1-yl]-piperidin-1-yl}-pyrimidine

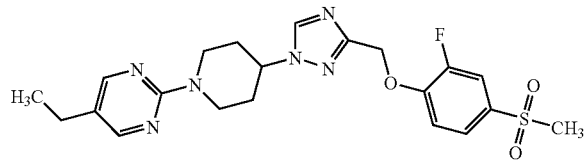

A mixture of 4-[3-(2-fluoro-4-methanesulfonyl-phenoxymethyl)-[1,2,4]triazol-1-yl]-piperidine hydrochloride salt (Intermediate 6, 0.100 g, 0.256 mmol), potassium carbonate (0.106 g, 0.768 mmol) and 2-chloro-5-ethyl-pyrimidine (0.062 mL, 0.512 mmol) in dimethylformamide (2 mL) was heated at 90° C. for 4 hours or until the starting material was consumed. The reaction was cooled to room temperature, the solution was diluted with water and extracted with ethyl acetate. The organic layer was separated, washed with water and brine, dried over sodium sulfate, filtered and concentra-

Example 10

5-Ethyl-2-{4-[4-(2-fluoro-4-methanesulfonyl-phenoxymethyl)-[1,2,3]triazol-2-yl]-piperidin-1-yl}-pyrimidine

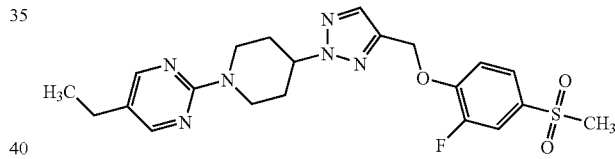

¹H NMR (CDCl₃): δ 8.21 (2H, s), 7.68 (3H, m), 7.28 (1H, m), 5.28 (2H, s), 4.82 (3H, m), 3.19 (2H, t), 3.02 (3H, s), 2.45 (2H, q), 2.23 (2H, m), 2.18 (2H, m), 1.20 (3H, t).

Example 11

5-Butyl-2-{4-[4-(2-fluoro-4-methanesulfonyl-phenoxymethyl)-[1,2,3]triazol-2-yl]-piperidin-1-yl}-pyrimidine

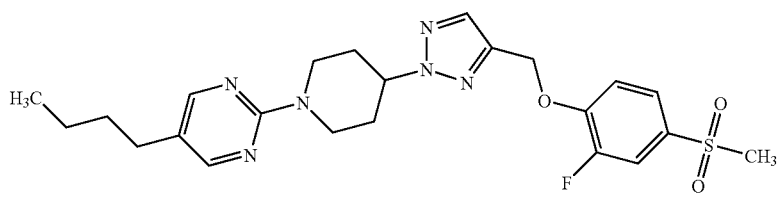

¹H NMR (CDCl₃): δ 8.17 (2H, s), 7.68 (3H, m), 7.27 (1H, m), 5.30 (2H, s), 4.81-4.70 (3H, m), 3.16 (2H, t), 3.05 (3H, s), 2.44 (2H, t), 2.26 (2H, m), 2.16 (2H, m), 1.53 (2H, m), 1.32 (2H, m), 0.95 (3H, q).

Example 12

5-Ethyl-2-{4-[4-(2-fluoro-4-tetrazol-1-yl-phenoxymethyl)-[1,2,3]triazol-2-yl]-piperidin-1-yl}-pyrimidine

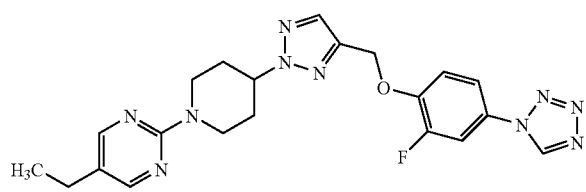

¹H NMR (CDCl₃): δ 8.92 (1H, s), 8.20 (2H, s), 7.71 (1H, s), 7.52 (1H, dd), 7.42 (1H, m), 7.30 (1H, d), 5.30 (2H, s), 4.80-4.70 (3H, m), 3.17 (2H, m), 2.48 (2H, q), 2.28-2.11 (4H, m), 1.21 (3H, t).

Example 13

5-Chloro-2-{4-[4-(2-fluoro-4-methanesulfonyl-phenoxymethyl)-[1,2,3]triazol-2-yl]-piperidin-1-yl}-pyrimidine

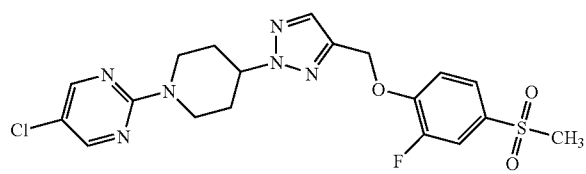

¹H NMR (CDCl₃): δ 8.25 (2H, s), 7.69 (3H, m), 7.28 (1H, m), 5.30 (2H, s), 4.76 (3H, m), 3.22 (2H, m), 3.04 (3H, s), 2.28-2.13 (4H, m).

Example 14

2-{4-[4-(2-Fluoro-4-methanesulfonyl-phenoxymethyl)-[1,2,3]triazol-2-yl]-piperidin-1-yl}-5-trifluoromethyl-pyrimidine

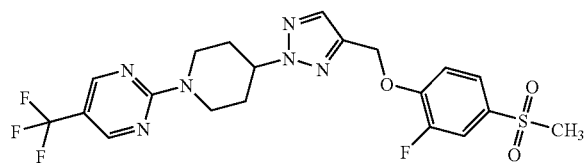

¹H NMR (CDCl₃): δ 8.50 (2H, s), 7.68 (3H, m), 7.27 (1H, m), 5.30 (2H, s), 4.78 (3H, m), 3.29 (2H, m), 3.04 (3H, s), 2.31-2.20 (4H, m).

Example 15

2-{4-[4-(2-Fluoro-4-tetrazol-1-yl-phenoxymethyl)-[1,2,3]triazol-2-yl]-piperidin-1-yl}-5-trifluoromethyl-pyrimidine

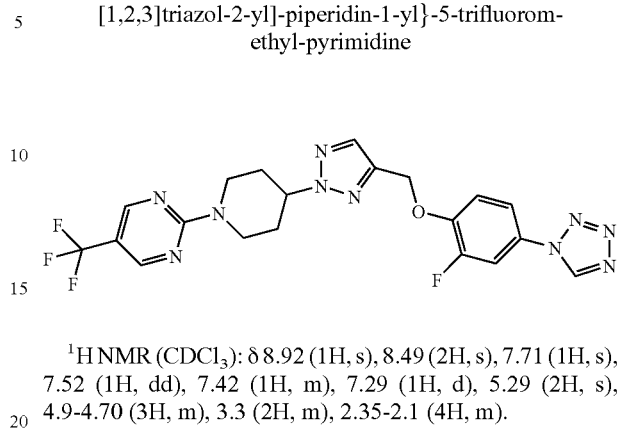

¹H NMR (CDCl₃): δ 8.92 (1H, s), 8.49 (2H, s), 7.71 (1H, s), 7.52 (1H, dd), 7.42 (1H, m), 7.29 (1H, d), 5.29 (2H, s), 4.9-4.70 (3H, m), 3.3 (2H, m), 2.35-2.1 (4H, m).

Example 16

5-Chloro-2-{4-[4-(2-fluoro-4-tetrazol-1-yl-phenoxymethyl)-[1,2,3]triazol-2-yl]-piperidin-1-yl}-pyrimidine

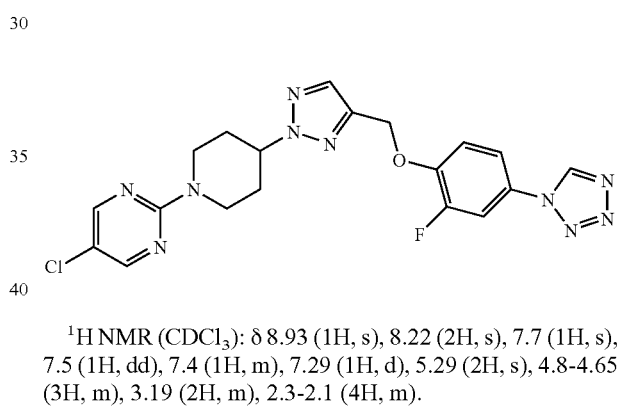

¹H NMR (CDCl₃): δ 8.93 (1H, s), 8.22 (2H, s), 7.7 (1H, s), 7.5 (1H, dd), 7.4 (1H, m), 7.29 (1H, d), 5.29 (2H, s), 4.8-4.65 (3H, m), 3.19 (2H, m), 2.3-2.1 (4H, m).

Example 17

5-Chloro-2-{4-[5-(2-fluoro-4-methanesulfonyl-phenoxymethyl)-tetrazol-2-yl]-piperidin-1-yl}-pyrimidine

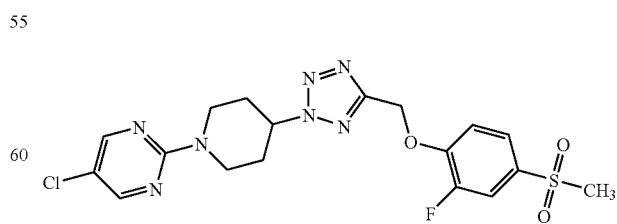

¹H NMR (CDCl₃): δ 8.24 (2H, s), 7.72-7.6 (2H, m), 7.33 (1H, t), 5.47 (2H, s), 5 (1H, m), 4.8-4.7 (2H, m), 3.24 (2H, m), 3.03 (3H, s), 2.36-2.28 (2H, m), 2.25-2.14 (2H, m).

Example 18

2-(4-(4-((4-(1H-tetrazol-1-yl)phenoxy)methyl)-1H-pyrazol-1-yl)piperidin-1-yl)-5-ethylpyrimidine

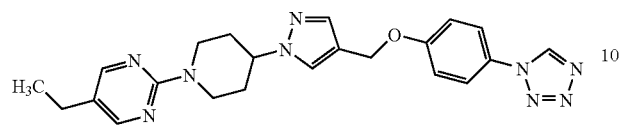

¹H NMR (CDCl₃): δ 8.90 (1H, s), 8.19 (2H, s), 7.60-7.55 (3H, m), 7.54 (1H, s), 7.10 (2H, J=9.2 Hz, d), 5.02 (2H, s), 4.87 (2H, m), 4.40 (1H, m), 3.04 (2H, m), 2.47 (2H, J=7.2 Hz, q), 2.23 (2H, m), 1.96 (2H, m), 1.20 (3H, J=7.2 Hz, t).

Example 19

5-Ethyl-2-(4-(4-((2-fluoro-4-(1H-tetrazol-1-yl)phenoxy)methyl)-1H-pyrazol-1-yl)piperidin-1-yl)pyrimidine

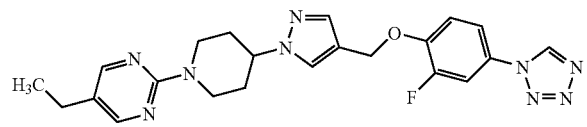

¹H NMR (CDCl₃): δ 8.92 (1H, s), 8.18 (2H, s), 7.58 (1H, s), 7.55 (1H, s), 7.49 (1H, m), 7.40 (1H, m), 7.19 (1H, m), 5.10 (2H, s), 4.86 (2H, m), 4.39 (1H, m), 3.03 (2H, m), 2.47 (2H, J=7.6 Hz, q), 2.21 (2H, m), 1.95 (2H, m), 1.19 (3H, J=7.6 Hz, t).

Example 20

2-{4-[4-(2-Fluoro-4-tetrazol-1-yl-phenoxymethyl)-[1,2,3]triazol-2-yl]-piperidin-1-yl}-5-methyl-pyrimidine

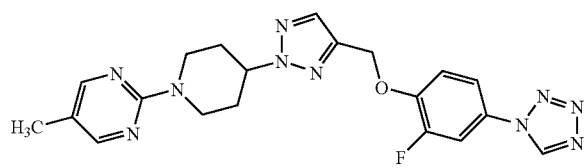

¹H NMR (CDCl₃): δ 8.86 (1H, s), 8.14 (2H, s), 7.64 (1H, s), 7.44 (1H, d), 7.35 (1H, d), 7.23 (1H, d), 5.23 (2H, s), 4.67 (2H, m), 4.15 (1H, m), 3.14 (2H, m), 2.21-2.12 (4H, m), 2.09 (3H, s).

Example 21

4-[4-(4-Methanesulfonyl-phenoxymethyl)-[1,2,3]triazol-1-yl]-piperidine-1-carboxylic acid tert-butyl ester

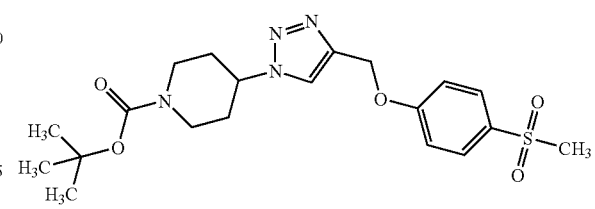

Step 1: Preparation of 1-methanesulfonyl-4-prop-2-ynyloxy-benzene

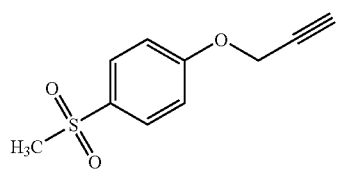

A mixture of 4-methylsulfonyl-phenol, propargyl bromide and K₂CO₃ was refluxed overnight. After cooling, the mixture was filtered through a pad of celite. The filtrate was concentrated in vacuo. The crude solid product was purified on silica gel to give the desired product as a pale yellow solid. ¹H NMR (CDCl₃): δ 7.9 (2H, d), 7.12 (2H, d), 4.79 (2H, d), 3.05 (3H, s), 2.58 (1H, t).

Step 2: Preparation of 4-azido-piperidine-1-carboxylic acid tert-butyl ester

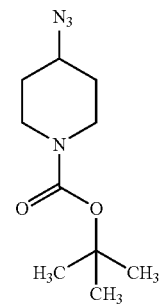

A mixture of 4-methanesulfonyloxy-piperidine-1-carboxylic acid tert-butyl ester and sodium azide in DMF was stirred at 60° C. overnight. The mixture was poured into water and the resulting mixture was extracted with EtOAc. The organic phase was separated and washed with water and brine, dried over Na₂SO₄, filtered and concentrated in vacuo to give the desired product as a pale yellow oil, which was used without further purification. ¹H NMR (CDCl₃): δ 7.9 (2H, d), 7.12 (2H, d), 4.79 (2H, d), 3.05 (3H, s), 2.58 9 (1H, t).

Step 3: Preparation of 4-[4-(4-Methanesulfonyl-phenoxymethyl)-[1,2,3]triazol-1-yl]-piperidine-1-carboxylic acid tert-butyl ester

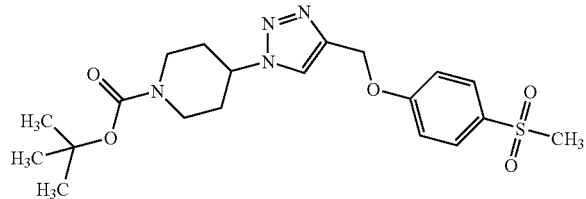

4-Azido-piperidine-1-carboxylic acid tert-butyl ester (1 eq) and 1-methanesulfonyl-4-prop-2-ynyloxy-benzene (1 eq) were suspended in H₂O/t-BuOH (1:1). Sodium ascorbate (0.1 eq) was added followed by CuSO₄.5H₂O (0.01 eq). The mixture was stirred vigorously overnight. The mixture was diluted with water and a precipitate formed. The precipitate was collected by filtration and purified on silica gel to give the desired product. ¹H NMR (CDCl₃): δ 7.88 (2H, d), 7.67 (1H, s), 7.14 (2H, d), 5.29 (2H, s), 4.64 (1H, m), 4.28 92H, m), 3.05 (3H, s), 2.94 (2H, m), 2.2 (2H, m), 1.96 (2H, m), 1.48 (9H, s).

The compounds in Examples 22-23 were synthesized from Intermediate 15 with the corresponding substituted 2-methanesulfonyl-pyrimidine or 2-iodopyrimidine in a manner similar to that described in Example 9. One skilled in the art of organic synthesis will appreciate that conditions such as solvent (DMF, CH₃CN), temperature, base (NEt₃, ⁱPr₂NEt, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 22

2-{4-[4-(6-Tetrazol-1-yl-pyridin-3-yloxymethyl)-[1,2,3]triazol-2-yl]-piperidin-1-yl}-5-trifluoromethyl-pyrimidine

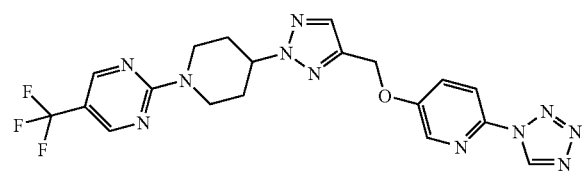

¹H NMR (DMSO-d₆): δ 10.06 (1H, s), 8.7 (2H, s), 8.4 (1H, d), 7.99 (1H, d), 7.94 (1H, s), 7.86 (1H, dd), 5.34 (2H, s), 4.92 (1H, m), 4.68 (2H, m), 3.33 (2H, m), 2.22 (2H, m), 1.94 (2H, m).

Example 23

5-Chloro-2-{4-[4-(6-tetrazol-1-yl-pyridin-3-yloxymethyl)-[1,2,3]triazol-2-yl]-piperidin-1-yl}-pyrimidine

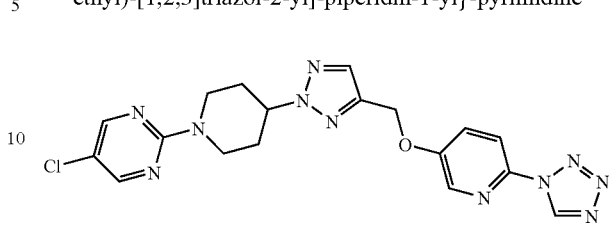

¹H NMR (CDCl₃): δ 9.44 (1H, s), 8.27 (1H, s), 8.26 (2H, s), 8.02 (1H, d), 7.71 (1H, s), 7.56 (1H, dd), 5.28 (2H, s), 4.75 (3H, m), 3.23 (2H, m), 2.29 (2H, m), 2.15 (2H, m).

The compounds listed in Examples 24-28 are synthesized in a manner similar to that described in Example 9 by using substituted 5-chloro-oxadiazoles in place of substituted 2-chloropyrimidines.

Example 24

1-[3-(1-Fluoro-1-methyl-ethyl)-[1,2,4]oxadiazol-5-yl]-4-[4-(2-fluoro-4-tetrazol-1-yl-phenoxymethyl)-[1,2,3]triazol-2-yl]-piperidine

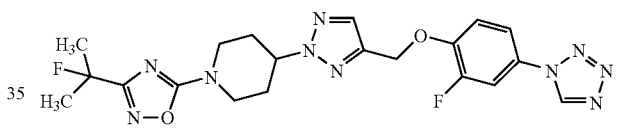

Example 25

1-(3-Cyclopropyl-[1,2,4]oxadiazol-5-yl)-4-[4-(2-fluoro-4-tetrazol-1-yl-phenoxymethyl)-[1,2,3]triazol-2-yl]-piperidine

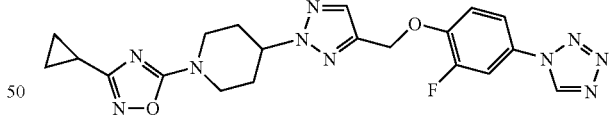

Example 26

4-[4-(2-Fluoro-4-tetrazol-1-yl-phenoxymethyl)-[1,2,3]triazol-2-yl]-1-(3-isopropyl-[1,2,4]oxadiazol-5-yl)-piperidine

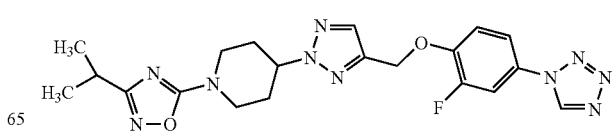

Example 27

5-{2-[1-(3-Isopropyl-[1,2,4]oxadiazol-5-yl)-piperidin-4-yl]-2H-[1,2,3]triazol-4-ylmethoxy}-2-tetrazol-1-yl-pyridine

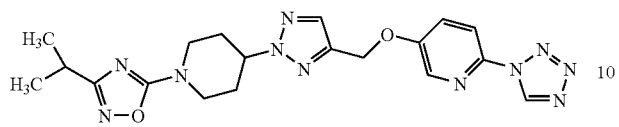

Example 28

5-(2-{1-[3-(1-Fluoro-1-methyl-ethyl)-[1,2,4]oxadiazol-5-yl]-piperidin-4-yl}-2H-[1,2,3]triazol-4-ylmethoxy)-2-tetrazol-1-yl-pyridine

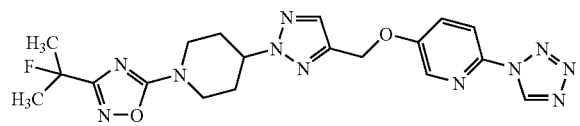

Example 29

5-{2-[1-(3-Cyclopropyl-[1,2,4]oxadiazol-5-yl)-piperidin-4-yl]-2H-[1,2,3]triazol-4-ylmethoxy}-2-tetrazol-1-yl-pyridine

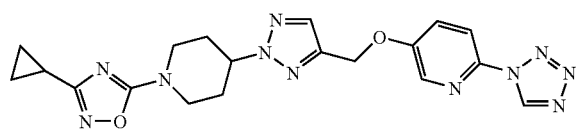

To a solution of 5-((2H-1,2,3-triazol-4-yl)methoxy)-2-(1H-tetrazol-1-yl)pyridine (0.500 g, 2.05 mmol) (Intermediate 13), in THF (4 mL) was added 4-(3-cyclopropyl-1,2,4-oxadiazol-5-yl)cyclohexanol (Intermediate 14), polymer supported triphenylphosphine (1.05 g, 3.07 mmol) and diisopropylazodicarboxylate (0.603 mL, 3.07 mmol). The suspension was stirred for 16 hours and filtered through a pad of celite. The filtrate was concentrated in vacuo and chromatographed on silica gel (1:1 hexanes/ethyl acetate) to obtain the expected product. $^1$H NMR (CDCl$_3$): δ 9.45 (1H, s), 8.28 (1H, s), 7.03 (1H, d), 7.72 (1H, s), 7.58 (1H, dd), 5.28 (2H, s), 4.72 (1H, m), 4.17 (2H, m), 3.34 (2H, m), 2.27 (4H, m), 1.89 (1H, m).

The compounds in Examples 30-34 were synthesized from one of Intermediates 6-12, 15 or 19 with the corresponding substituted 2-fluoropyrimidine, 2-chloropyrimidine, 2-bromopyrimidine, 2-iodopyrimidine, 2-(methylsulfinyl)pyrimidine or 2-(methylsulfonyl)pyrimidine in a manner similar to that described in Example 9. One skilled in the art of organic synthesis will appreciate that conditions such as solvent (DMF, CH$_3$CN), temperature, base (NEt$_3$, $^i$Pr$_2$NEt, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 30

5-Fluoro-2-(4-(4-((2-fluoro-4-(1H-tetrazol-1-yl)phenoxy)methyl)-2H-1,2,3-triazol-2-yl)piperidin-1-yl)pyrimidine

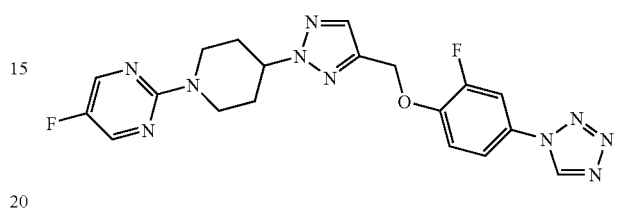

$^1$H NMR (CDCl$_3$): δ 8.91 (1H, s), 8.21 (2H, s), 7.72 (1H, s), 7.46 (1H, d), 7.41 (1H, d), 7.23 (1H, m), 5.23 (2H, s), 4.72 (3H, m), 3.19 (2H, m), 2.22 (2H, m), 2.19 (2H, m).

Example 31

2-(4-(4-((6-(1H-tetrazol-1-yl)pyridin-3-yloxy)methyl)-2H-1,2,3-triazol-2-yl)piperidin-1-yl)-5-fluoropyrimidine

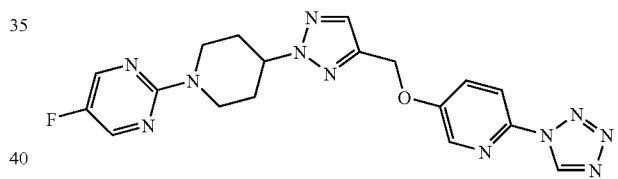

$^1$H NMR (CDCl$_3$): δ 9.43 (1H, s), 8.23 (1H, d), 8.21 (2H, s), 8.01 (1H, d), 7.71 (1H, s), 7.59 (1H, dd), 5.23 (2H, s), 4.77 (3H, m), 3.20 (2H, m), 2.29 (2H, m), 2.18 (2H, m).

Example 32

2-(4-(4-((6-(1H-tetrazol-1-yl)pyridin-3-yloxy)methyl)-2H-1,2,3-triazol-2-yl)piperidin-1-yl)-5-ethylpyrimidine

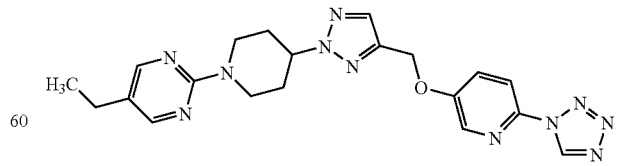

$^1$H NMR (CDCl$_3$): δ 9.44 (1H, s), 8.27 (1H, d), 8.20 (2H, s), 8.02 (1H, d), 7.70 (1H, s), 7.59 (1H, dd), 5.28 (2H, s), 4.77 (3H, m), 3.20 (2H, m), 2.50 (2H, q), 2.22 (2H, m), 2.14 (2H, m), 1.20 (3H, t).

Example 33

5-Chloro-2-((trans)-3-fluoro-4-(4-((2-fluoro-4-(1H-tetrazol-1-yl)phenoxy)methyl)-2H-1,2,3-triazol-2-yl)piperidin-1-yl)pyrimidine

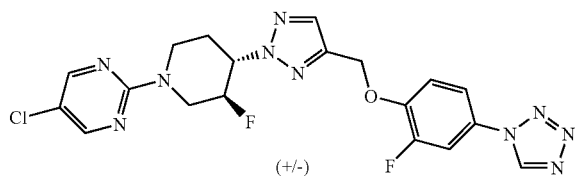

$^{1}$H NMR (CDCl$_{3}$): δ 8.93 (1H, s), 8.28 (2H, s), 7.77 (1H, s), 7.52 (1H, dd), 7.41 (1H, dd), 7.27 (1H, m), 5.31 (2H, s), 5.08 (1H, m), 4.91 (1H, m), 4.75 (2H, m), 3.23 (2H, m), 2.26 (2H, m).

Example 34

2-((trans)-3-Fluoro-4-(4-((2-fluoro-4-(1H-tetrazol-1-yl)phenoxy)methyl)-2H-1,2,3-triazol-2-yl)piperidin-1-yl)-5-(trifluoromethyl)pyrimidine

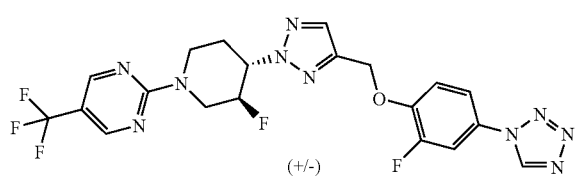

$^{1}$H NMR (CDCl$_{3}$): δ 8.91 (1H, s), 8.54 (2H, s), 7.77 (1H, s), 7.52 (1H, dd), 7.41 (1H, d), 7.27 (1H, m), 5.31 (2H, s), 5.10 (1H, m), 4.93 (1H, m), 4.82 (2H, m), 3.34 (2H, m), 2.26 (2H, m).

Example 35

Isopropyl 4-(4-((6-(1H-tetrazol-1-yl)pyridin-3-yloxy)methyl)-2H-1,2,3-triazol-2-yl)piperidine-1-carboxylate

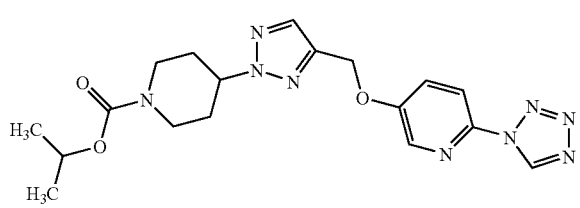

To a suspension of 5-((2-(piperidin-4-yl)-2H-1,2,3-triazol-4-yl)methoxy)-2-(1H-tetrazol-1-yl)pyridine (Intermediate 15) (0.300 g, 0.917 mmol) in ethyl acetate (3 mL) was added triethylamine (0.169 mL, 1.22 mmol) and isopropyl chloroformate (1.10 mL, 1M solution in toluene, 1.10 mmol). The resulting solution was stirred for 1 hour. Water was added and the solution was extracted with ethyl acetate. The organic layer was separated, dried over sodium sulfate, filtered and concentrated in vacuo. The residue was chromatographed on silica gel (1:1 hexanes/ethyl acetate) to obtain the expected product. $^{1}$H NMR (CDCl$_{3}$): δ 9.45 (1H, s), 8.28 (1H, d), 8.03 (1H, d), 7.71 (1H, s), 7.58 (1H, dd), 5.28 (2H, s), 4.95 (1H, m), 4.64 (1H, m), 4.22 (1H, m), 2.21 (2H, m), 2.14 (2H, m), 1.26 (6H, d).

Example 36

Isopropyl 4-(4-((2-fluoro-4-(methylsulfonyl)phenoxy)methyl)-2H-1,2,3-triazol-2-yl)piperidine-1-carboxylate

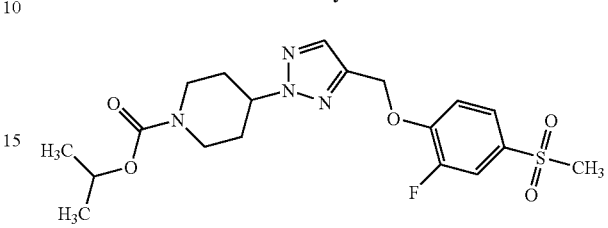

The title compound was synthesized using 4-[4-(2-Fluoro-4-methanesulfonyl-phenoxymethyl)-[1,2,3]triazol-2-yl]-piperidine (Intermediate 7) and isopropyl chloroformate in a manner similar to that described in Example 35. $^{1}$H NMR (CDCl$_{3}$): δ 7.66 (3H, m), 7.27 (1H, m), 5.30 (2H, s), 4.94 (1H, m), 4.63 (1H, m), 4.20 (2H, m), 3.04 (3H, s), 2.19 (2H, m), 2.17 (2H, m), 1.25 (6H, d).

Example 37

Isopropyl 4-(4-((2-fluoro-4-(1H-tetrazol-1-yl)phenoxy)methyl)-2H-1,2,3-triazol-2-yl)piperidine-1-carboxylate

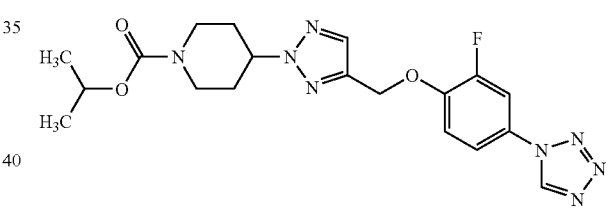

The title compound was synthesized using 1-(4-((2H-1,2,3-triazol-4-yl)methoxy)-3-fluorophenyl)-1H-tetrazole (Intermediate 8) and isopropyl chloroformate in a manner similar to that described in Example 35. $^{1}$H NMR (CDCl$_{3}$): δ 8.93 (1H, s), 7.71 (1H, s), 7.52 (1H, dd), 7.43 (1H, m), 7.31 (1H, t), 5.3 (2H, s), 4.94 (1H, m), 4.63 (1H, m), 4.2 (2H, br), 3.03 (2H, m), 2.15 (4H, m), 1.26 (6H, d).

Example 38

5-Ethyl-2-((trans)-3-fluoro-4-(4-((2-fluoro-4-(1H-tetrazol-1-yl)phenoxy)methyl)-2H-1,2,3-triazol-2-yl)piperidin-1-yl)pyrimidine

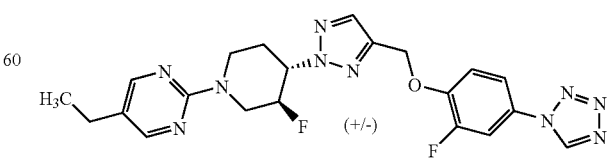

The title compound was synthesized using 1-(4-((2H-1,2,3-triazol-4-yl)methoxy)-3-fluorophenyl)-1H-tetrazole (Intermediate 16) and cis-1-(5-ethylpyrimidin-2-yl)-3-fluoropiperidin-4-ol (Intermediate 17) in a manner similar to that described in Example 29. $^1$H NMR (CDCl$_3$): δ 8.92 (1H, s), 8.21 (2H, s), 7.76 (1H, s), 7.51 (1H, dd), 7.41 (1H, d), 7.26 (1H, m), 5.31 (2H, s), 5.17 (1H, m), 5.03 (1H, m), 4.83 (2H, m), 3.11 (2H, m), 2.50 (2H, q), 2.22 (2H, m), 1.22 (3H, t).

Example 39

5-(4-(4-((6-(1H-Tetrazol-1-yl)pyridin-3-yloxy)methyl)-2H-1,2,3-triazol-2-yl)piperidin-1-ylsulfonyl)-2,4-dimethylthiazole

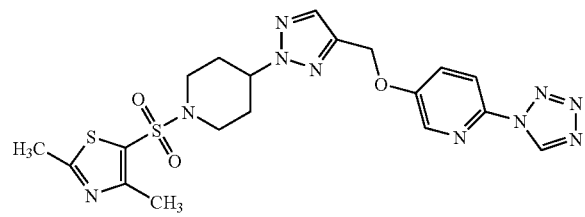

To a solution of 5-((2-(piperidin-4-yl)-2H-1,2,3-triazol-4-yl)methoxy)-2-(1H-tetrazol-1-yl)pyridine hydrochloride (Intermediate 15, 0.050 g, 0.153 mmol), dichloromethane (1.5 mL), and triethyl amine (0.043 mL, 0.306 mmol) was added 2,4-dimethyl-thiazole-5-sulfonyl chloride (0.049 g, 0.229 mmol) and the reaction stirred at room temperature for 2 hours. The solution was concentrated and purified by flash column chromatography on silica gel eluting with 0-100% ethyl acetate in hexanes to afford the desired product.

$^1$H NMR (DMSO-d$_6$): δ 10.01 (1H, s), 8.41 (1H, d), 8.00 (1H, d), 7.94 (1H, s), 7.85 (1H, dd), 5.34 (2H, s), 4.66 (1H, m), 3.69 (2H, m), 2.81 (2H, m), 2.64 (3H, s), 2.51 (3H, s), 2.24 (2H, m), 2.02 (2H, m).

Example 40

5-((2-(1-(1H-Imidazol-4-ylsulfonyl)piperidin-4-yl)-2H-1,2,3-triazol-4-yl)methoxy)-2-(1H-tetrazol-1-yl)pyridine

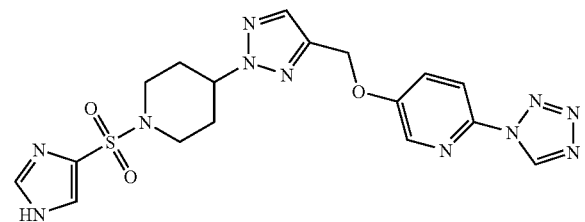

The title compound was synthesized using Intermediate 15 and 1H-imdazole-4-sulfonyl chloride in a similar manner as described in Example 39. $^1$H NMR (DMSO-d$_6$): δ 12.89 (1H, bs), 10.07 (1H, s), 8.41 (1H, d), 7.99 (1H, d), 7.92 (1H, s), 7.86 (2H, m), 7.79, (1H, dd), 5.32 (2H, s), 4.59 (1H, m), 3.62 (2H, m), 2.77 (2H, m), 2.17 (2H, m), 1.95 (2H, M).

Example 41

5-((2-(1-(Cyclopropylsulfonyl)piperidin-4-yl)-2H-1,2,3-triazol-4-yl)methoxy)-2-(1H-tetrazol-1-yl)pyridine

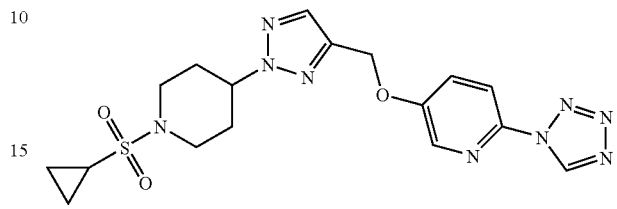

The title compound was synthesized using Intermediate 15 and cyclopropanesulfonyl chloride in a similar manner as described in Example 39. $^1$H NMR (DMSO-d$_6$): δ 9.45 (1H, s), 8.28 (1H, d), 8.03 (1H, d), 7.73 (1H, s), 7.58 (1H, dd), 5.28 (2H, s), 4.62 (1H, m), 3.87 (2H, m), 3.12 (2H, m) 2.31 (5H, m), 1.86 (2H, m), 1.02 (2H, m).

Example 42

5-((2-(1-(1-Methyl-1H-imidazol-4-ylsulfonyl)piperidin-4-yl)-2H-1,2,3-triazol-4-yl)methoxy)-2-(1H-tetrazol-1-yl)pyridine

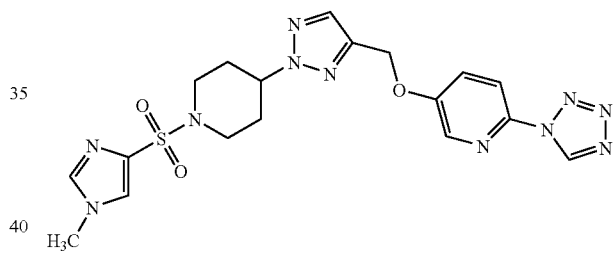

The title compound was synthesized using Intermediate 15 and 1-methyl-1-imidazole-4-sulfonyl chloride in a similar manner as described in Example 39. $^1$H NMR (DMSO-d$_6$): δ 10.07 (1H, s), 8.41 (1H, d), 8.00 (1H, d), 7.93 (1H, s), 7.87 (1H, dd), 7.82 (2H, s), 5.34 (2H, s), 4.59 (1H, m), 3.69 (3H, s), 3.36 (2H, m), 2.74 (2H, m), 2.19 (2H, m), 2.00 (2H, m).

Example 43

4-(4-(4-((6-(1H-Tetrazol-1-yl)pyridin-3-yloxy)methyl)-2H-1,2,3-triazol-2-yl)piperidin-1-ylsulfonyl)-3,5-dimethylisoxazole

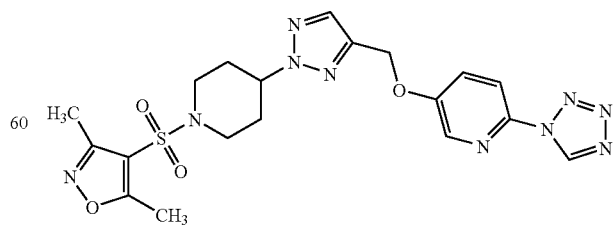

The title compound was synthesized using Intermediate 15 and 3,5-dimethylisoxazole-4-sulfonyl chloride in a similar manner as described in Example 39. ¹H NMR (DMSO-d₆): δ 10.07 (1H, s), 8.41 (1H, d), 8.00 (1H, d), 7.94 (1H, s), 7.86 (1H, dd), 5.34 (2H, s), 4.65 (1H, m), 3.68 (2H, m), 2.86 (2H, m), 2.61 (3H, s), 2.33 (3H, s), 2.24 (2H, m), 2.00 (2H, m).

Example 44

5-((2-(1-(Cyclohexylsulfonyl)piperidin-4-yl)-2H-1,2,3-triazol-4-yl)methoxy)-2-(1H-tetrazol-1-yl)pyridine

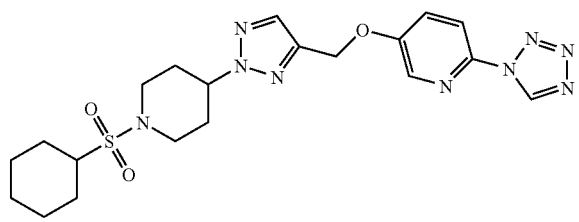

The title compound was synthesized using Intermediate 15 and cyclohexanesulfonyl chloride in a similar manner as described in Example 39. ¹H NMR (DMSO-d₆): δ 10.08 (1H, s), 8.42 (1H, d), 8.01 (1H, d), 7.95 (1H, s), 7.86 (1H, dd), 3.52 (2H, s), 4.74 (1H, m), 3.68 (2H, m), 3.11 (3H, m) 2.51 (1H, m), 2.17 (2H, m) 1.92 (3H, m), 1.73 (1H, m), 1.23 (7H, m).

Example 45

5-((2-(1-(Isopropylsulfonyl)piperidin-4-yl)-2H-1,2,3-triazol-4-yl)methoxy)-2-(1H-tetrazol-1-yl)pyridine

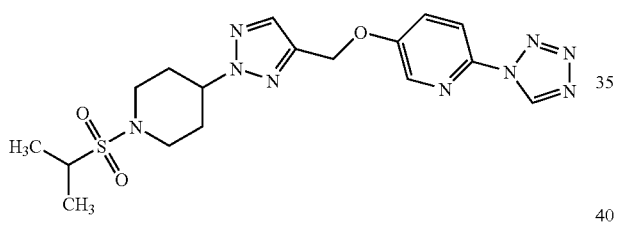

The title compound was synthesized using Intermediate 15 and isopropylsulfonyl chloride in a similar manner as described in Example 39. ¹H NMR (DMSO-d₆): δ 10.08 (1H, s), 8.41 (1H, d), 8.01 (1H, d), 7.95 (1H, s), 7.86 (1H, dd), 5.35 (2H, s), 4.75 (1H, m), 3.69 (2H, m), 3.31 (1H, m), 3.13 (2H, m), 2.17 (2H, m), 1.97 (2H, m), 1.20 (6H, d).

Example 46

5-((2-(1-(Butylsulfonyl)piperidin-4-yl)-2H-1,2,3-triazol-4-yl)methoxy)-2-(1H-tetrazol-1-yl)pyridine

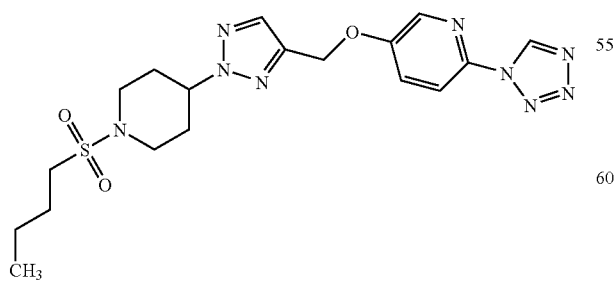

The title compound was synthesized using Intermediate 15 and 1-butanesulfonyl chloride in a similar manner as described in Example 39. ¹H NMR (DMSO-d₆): δ 10.08 (1H, s), 8.41 (1H, d), 8.00 (1H, d), 7.96 (1H, s), 7.86 (1H, dd), 5.36 (2H, s), 4.71 (1H, m), 3.63 (2H, m), 3.01 (4H, m), 2.2 (2H, m), 1.99 (2H, m), 1.64 (2H, m), 1.39 (2H, m), 0.89 (3H, t).

Example 47

5-((2-(1-(Benzylsulfonyl)piperidin-4-yl)-2H-1,2,3-triazol-4-yl)methoxy)-2-(1H-tetrazol-1-yl)pyridine

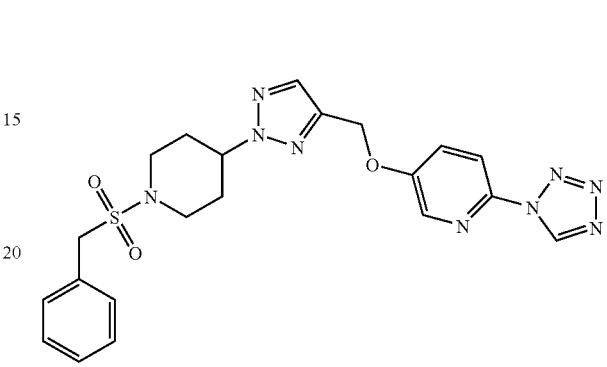

The title compound was synthesized using Intermediate 15 and phenylmethanesulfonyl chloride in a similar manner as described in Example 39. ¹H NMR (DMSO-d₆): δ 10.07 (1H, s), 8.41 (1H, d), 8.00 (1H, d), 7.96 (1H, s), 7.86 (1H, dd), 7.36 (5H, m), 5.35 (2H, s), 4.68 (1H, m), 4.43 (2H, s) 3.54 (2H, m), 2.99 (2H, m), 2.12 (2H, m), 1.91 (2H, m).

Example 48

2-(4-(4-((2-Methylpyridin-3-yloxy)methyl)-2H-1,2,3-triazol-2-yl)piperidin-1-ylsulfonyl)-5-(trifluoromethyl)pyrimidine

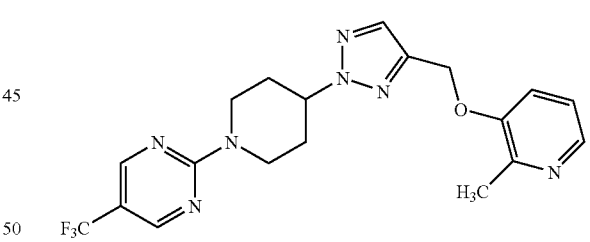

Step 1: 2-Methyl-3-(prop-2-ynyloxy)pyridine

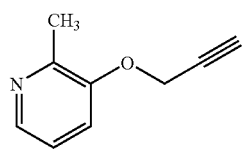

The title compound was synthesized using 3-hydroxy-2-methylpyridine and propargyl chloride in a manner similar to that described in Intermediate 13, Step 2.

Step 2: (5-((2-Methylpyridin-3-yloxy)methyl)-1H-1,2,3-triazol-1-yl)methyl pivalate

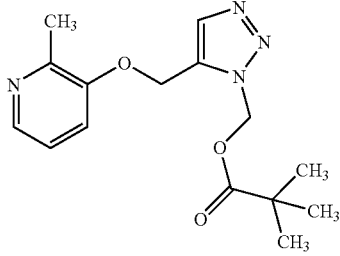

The title compound was synthesized using 2-methyl-3-(prop-2-ynyloxy)pyridine and azidomethyl pivalate in a manner similar as that described in Intermediate 13, Step 3.

Step 3: 3-((1H-1,2,3-Triazol-5-yl)methoxy)-2-methylpyridine

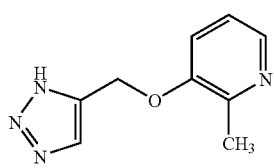

The title compound was synthesized using (5-((2-methylpyridin-3-yloxy)methyl)-1H-1,2,3-triazol-1-yl)methyl pivalate and sodium hydroxide in a manner similar as that described in Intermediate 13, Step 4.

Step 4: 2-(4-(4-((2-Methylpyridin-3-yloxy)methyl)-2H-1,2,3-triazol-2-yl)piperidin-1-yl)-5-(trifluoromethyl)pyrimidine

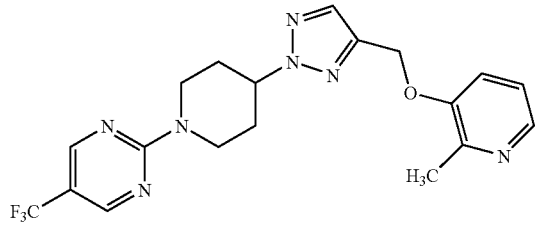

To a solution of 3-((1H-1,2,3-triazol-5-yl)methoxy)-2-methylpyridine (0.20 g, 1.05 mmol), in THF (2 mL) at 0° C., was added 1-(5-(trifluoromethyl)pyrimidin-2-yl)piperidin-4-ol (0.391 g, 1.58 mmol) (Intermediate 20), polymer bound triphenylphosphine (0.527 g, 1.58 mmol), and di-tert-butylazodicarboxylate (0.363, 1.58 mmol). The reaction was allowed to warm to room temperature overnight and was then filtered through a pad of celite washing with THF. The solution was concentrated in vacuo and purified by flash column chromatography on silica gel eluting with 0-60% ethyl acetate in hexane to afford the desired product. $^1$H NMR (DMSO-$d_6$): δ 8.71 (2H, s), 8.00 (1H, dd), 7.89 (1H, s), 7.47 (1H, dd), 7.19 (1H, dd), 5.18 (2H, s), 4.90 (1H, m), 4.68 (2H, s), 3.31 (2H, m), 2.31 (3H, s), 2.19 (2H, m), 1.92 (2H, m).

Example 49

(trans)-tert-Butyl 3-fluoro-4-(4-((2-fluoro-4-(1H-tetrazol-1-yl)phenoxy)methyl)-2H-1,2,3-triazol-2-yl)piperidine-1-carboxylate

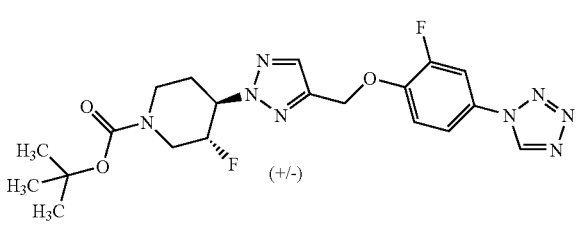

The title compound was synthesized using Intermediate 18 and Intermediate 16 in a similar manner to that described in Example 29. $^1$H NMR (CDCl$_3$): δ 8.98 (1H, s), 7.74 (1H, s), 7.51 (1H, dd), 7.43 (1H, m), 7.26 (1H, t), 5.29 (2H, s), 4.94 (1H, m), 4.7 (1H, m), 4.43 (1H, m), 4.1 (1H, m), 2.96 (2H, m), 2.16 (2H, m), 1.45 (9H, s).

Example 50 tert-Butyl 4-(2-(4-(-((6-(1H-tetrazol-1-yl)pyridine-3-yloxy)methyl)-2H-1,2,3-triazol-2-yl)piperidin-1-yl)-2-oxoethyl)piperidine-1-carboxylate

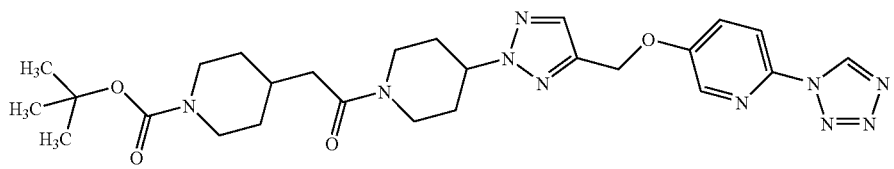

To a stirred solution of 5-((2-(Piperidin-4-yl)-2H-1,2,3-triazol-4-yl)methoxy)-2-(1H-tetrazol-1-yl)pyridine (225 mg, 0.688 mmol) (Intermediate 15) dissolved in DMF (10 mL) was added triethylamine (4 eq.) and o-benzotriazol-1-yl-N,N,N',N'-tetramethyluronium tetrafluoroborate (TBTU) (2 eq.). The solution was stirred for 5 minutes and 2-(1-(tert-butoxycarbonyl)piperidin-4-yl)acetic acid (1.5 eq.) was added and was stirred at room temperature for 3 h. The reaction was quenched with water and extracted with ethyl acetate. The organic layer was washed with brine, and dried over sodium sulfate. The solution was filtered and concentrated in vacuo. The crude product was purified by flash column chromatography on silica gel eluting with ethyl acetate and hexanes to afford the desired product. $^1$H NMR (DMSO-$d_6$): δ 10.07 (1H, s), 8.40 (1H, d), 8.00 (1H, d), 7.93 (1H, s), 7.86 (1H, dd), 5.34 (2H, s), 4.78 (1H, m), 4.35 (1H, m), 3.85-3.94 (3H, m), 3.21 (1H, m), 2.64-2.82 (3H, m), 2.27 (2H, d), 2.10 (2H, m), 1.86 (3H, m), 1.60 (2H, d), 1.35 (9H, s), 1.99 (2H, m).

Example 51

1-(4-(4-((6-(1H-Tetrazol-1-yl)pyridin-3-yloxy)methyl)-2H-1,2,3-triazol-2-yl)piperidin-1-yl)-2-(piperidin-4-yl)ethanone hydrochloride

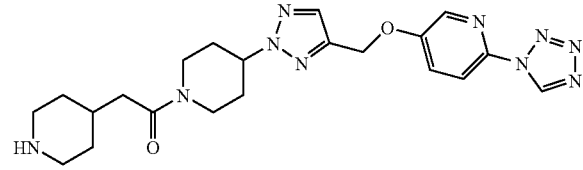

To a solution of tert-butyl 4-(2-(4-(-((6-(1H-tetrazol-1-yl)pyridin-3-yloxy)methyl)-2H-1,2,3-triazol-2-yl)piperidin-1-yl)-2-oxoethyl)piperidine-1-carboxylate (110 mg, 0.20 mmol) in dichloromethane (5 mL) cooled to 0° C. was added hydrochloric acid (4M in 1,4-dioxane, 5 eq.) dropwise. After the reaction was stirred for 3 h the solvents were removed in vacuo to afford the desired HCl salt. $^1$H NMR (DMSO-$d_6$): δ 10.06 (1H, s), 8.78 (1H, br), 8.40 (1H, d), 7.98 (1H, d), 7.94 (1H, s), 7.87 (1H, dd), 5.35 (2H, s), 4.79 (1H, m), 4.34 (1H, m), 3.92 (1H, m), 3.20 (3H, m), 2.83 (2H, m), 2.31 (2H, d), 2.10 (2H, m), 1.93 (2H, m), 1.77 (3H, m), 1.32 (2H, m).

Example 52

Methyl 2-(2-(4-(4-((6-(1H-tetrazol-1-yl)pyridin-3-yloxy)methyl)-2H-1,2,3-triazol-2-yl)piperidin-1-yl)pyrimidin-5-yl)acetate

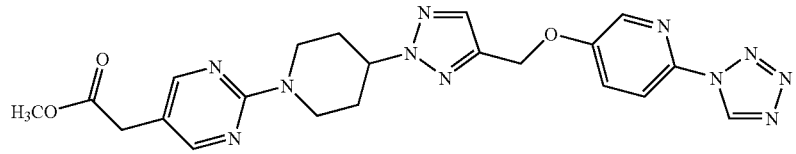

To a solution of 5-((2-(Piperidin-4-yl)-2H-1,2,3-trazol-4-yl)methoxy)-2-(1H-tetrazol-1-yl)pyridine (85 mg, 0.26 mmol) in DMF (5 mL) was added triethylamine (3 eq.) and methyl 2-(2-(methylsulfonyl)pyrimidin-5-yl)acetate (2 eq.). The reaction was stirred overnight at room temperature, then was partitioned between ethyl acetate and water. The organic layer was washed with brine, dried over sodium sulfate, filtered, and concentrated in vacuo. The crude material was purified by flash chromatography on silica gel eluting with ethyl acetate and hexanes to afford the title compound. $^1$H NMR (CDCl$_3$): δ 9.44 (1H, s), 8.27 (1H, d), 8.25 (2H, s), 8.02 (1H, d), 7.70 (1H, s), 7.59 (1H, dd), 5.27 (2H, s), 4.78 (3H, m), 3.45 (2H, s), 3.36 (3H, s), 3.20 (2H, m), 2.27 (2H, m), 2.17 (2H, m).

Example 53

(S)-tert-Butyl 1-(4-(4-((6-(1H-tetrazol-1-yl)pyridin-3-yloxy)methyl)-2H-1,2,3-triazol-2-yl)piperidin-1-yl)-1-oxopropan-2-ylcarbamate

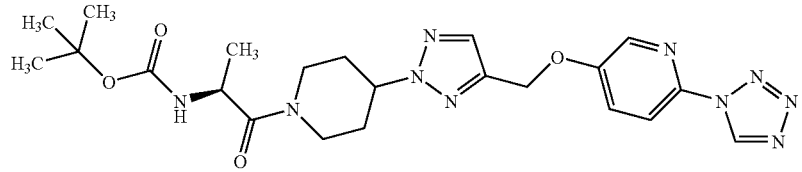

The title compound was prepared in a manner analogous to Example 50 above. ¹H NMR (CDCl₃): δ 9.45 (1H, s), 8.28 (1H, d), 8.03 (1H, d), 7.72 (1H, s), 7.58 (1H, dd), 5.52 (1H, m), 5.28 (2H, s), 4.71 (2H, m), 4.41-4.67 (1H, m), 4.04 (1H, m), 2.97-3.40 (2H, m), 2.25 (4H, m), 1.44 (9H, s), 1.32 (3H, m).

Example 54

(S)-tert-Butyl 1-(4-(4-((6-(1H-tetrazol-1-yl)pyridin-3-yloxy)methyl)-2H-1,2,3-triazol-2-yl)piperidin-1-yl)-1-oxopropan-2-ylcarbamate

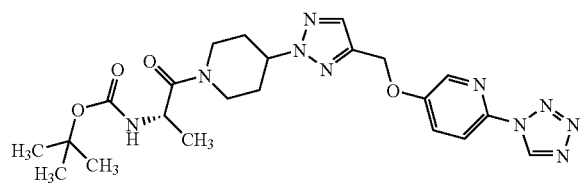

The title compound was prepared in a manner similar to that described in Example 50. ¹H NMR (CDCl₃): δ 9.44 (1H, s), 8.27 (1H, d), 8.03 (1H, d), 7.72 (1H, s), 7.58 (1H, dd), 5.52 (1H, m), 5.29 (2H, s), 4.71 (2H, m), 4.45 (1H, m), 3.99 (1H, m), 2.96-3.11 (2H, m), 2.19 (4H, m), 1.44 (9H, s), 1.32 (3H, m).

Example 55

(S)-1-(4-(4-((6-(1H-tetrazol-1-yl)pyridin-3-yloxy)methyl)-2H-1,2,3-triazol-2-yl)piperidin-1-yl)-2-aminopropan-1-one hydrochloride

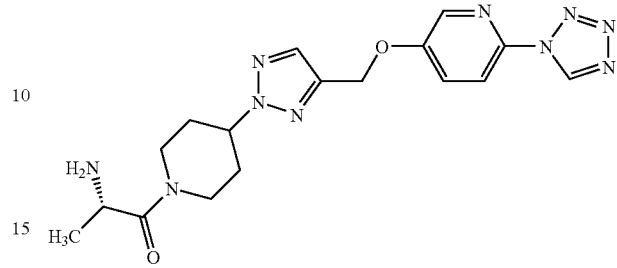

The title compound was prepared from (S)-tert-butyl 1-(4-(4-((6-(1H-tetrazol-1-yl)pyridin-3-yloxy)methyl)-2H-1,2,3-triazol-2-yl)piperidin-1-yl)-1-oxopropan-2-ylcarbamate (Example 54) in a manner similar to that described in Example 51. LCMS: (ES⁺-MS found: 398.6).

Example 56

(S)-tert-Butyl 4-(4-(4-((6-(1H-tetrazol-1-yl)pyridin-3-yloxy)methyl)-2H-1,2,3-triazol-2-yl)piperidin-1-yl)-4-oxo-1-(2,4,5-trifluorophenyl)butan-2-ylcarbamate

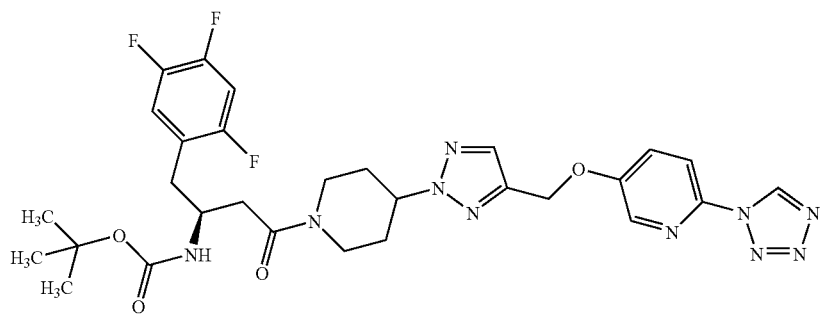

The title compound was prepared in a manner similar to that described in Example 50. ¹H NMR (CDCl₃): δ 9.44 (1H, s), 8.27 (1H, s), 8.03 (1H, d), 7.72 (1H, d), 7.58 (1H, dd), 7.08 (1H, m), 6.90 (1H, m), 5.58 (1H, m), 5.28 (2H, s), 4.71 (1H, m), 4.54 (1H, m), 4.13 (1H, m), 3.87 (1H, m), 3.25 (1H, m), 2.96 (3H, m), 2.60 (2H, m), 2.11-2.27 (4H, m), 1.37 (9H, s).

Example 57

(S)-1-(4-(4-((6-(1H-tetrazol-1-yl)pyridin-3-yloxy)methyl)-2H-1,2,3-triazol-2-yl)piperidin-1-yl)-3-amino-4-(2,4,5-trifluorophenyl)butan-1-one hydrochloride

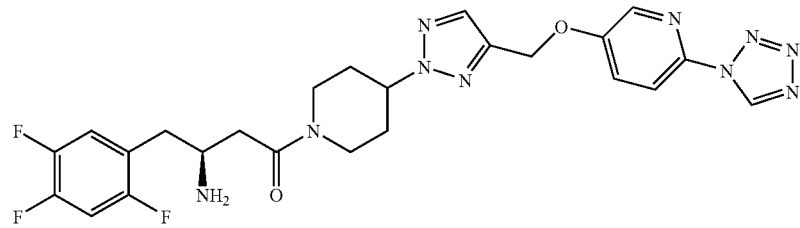

The title compound was prepared from (S)-tert-Butyl 4-(4-(4-((6-(1H-tetrazol-1-yl)pyridin-3-yloxy)methyl)-2H-1,2,3-triazol-2-yl)piperidin-1-yl)-4-oxo-1-(2,4,5-trifluorophenyl)butan-2-ylcarbamate (Example 56) in a manner similar to that described in Example 51. LCMS: (ES+-MS found: 542.6).

Example 58

Ethyl 4-(2-(4-(4-((6-(1H-tetrazol-1-yl)pyridin-3-yloxy)methyl)-2H-1,2,3-triazol-2-yl)piperidin-1-yl)pyrimidin-5-yl)butanoate

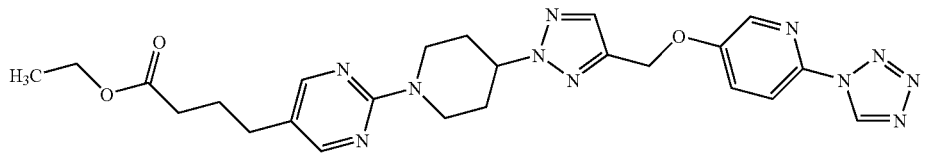

The title compound was prepared from Intermediate 15 in a manner similar to that described in Example 9. LCMS (ES+-MS found: 520.0).

Example 59

(trans)-1-tert-Butyl 2-methyl 4-(4-((6-(1H-tetrazol-1-yl)pyridin-3-yloxy)methyl)-2H-1,2,3-triazol-2-yl)piperidine-1,2-dicarboxylate

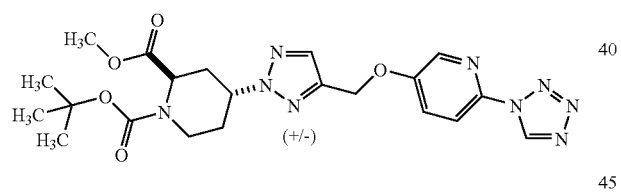

To a solution of 5-((2H-1,2,3-triazol-4-yl)methoxy)-2-(1H-tetrazol-1-yl)pyridine (600 mg, 2.45 mmol), triphenylphosphine (1.5 eq.), and (2R,4S)-N-Boc-4-hydroxypiperidine-2-carboxylic acid methyl ester (1.5 eq.) dissolved in THF (20 mL) at 0° C. was added a solution of di-tertbutylazodicarboxylate (1.5 eq.) in THF (5 mL) drop wise. The reaction was allowed to warm to room temperature overnight and the solvents removed in vacuo The crude material was purified by flash column chromatography on silica gel to afford the desired product. $^1$H NMR (CDCl$_3$): δ 9.44 (1H, s), 8.27 (1H, d), 8.03 (1H, d), 7.71 (1H, s), 7.58 (1H, dd), 5.27 (2H, s), 4.99-5.19 (1H, m), 4.57 (1H, m), 4.11-4.31 (1H, m), 3.79 (3H, s), 3.04-3.24 (1H, m), 2.75 (1H, m), 2.18-2.32 (2H, m), 2.05 (1H, m), 1.50 (9H, s). ES+-MS found: 486.1.

Example 60

Ethyl 4-(2-(4-(4-((6-(1H-tetrazol-1-yl)pyridin-3-yloxy)methyl)-2H-1,2,3-triazol-2-yl)piperidin-1-yl)pyrimidine-5-carboxylate

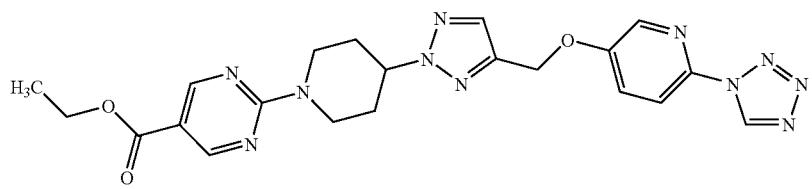

The title compound was prepared in a manner similar to that described in Example 52 above. $^1$H NMR (CDCl$_3$): δ 9.45 (1H, s), 8.86 (2H, s), 8.27 (1H, d), 8.03 (1H, d), 7.72 (1H, s), 7.58 (1H, dd), 5.27 (2H, s), 4.92 (2H, m), 4.80 (1H, m), 4.35 (2H, q), 3.31 (2H, m), 2.32 (2H, m), 2.18 (2H, m), 1.37 (3H, t). LCMS: (ES+-MS found: 478.2).

Example 61

2-(4-(4-((6-(1H-tetrazol-1-yl)pyridin-3-yloxy)methyl)-2H-1,2,3-triazol-2-yl)piperidin-1-yl)pyrimidin-5-yl)(morpholino)methanone

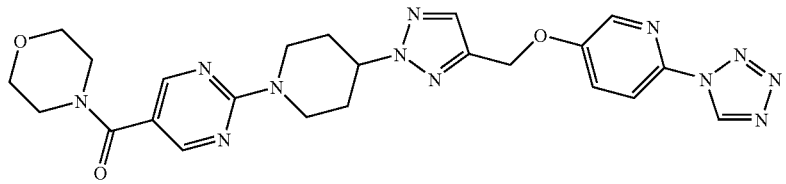

Step 1: Preparation of 2-(4-(4-((6-(1H-tetrazol-1-yl)pyridin-3-yloxy)methyl)-2H-1,2,3-triazol-2-yl)piperidin-1-yl)pyrimidine-5-carboxylic acid

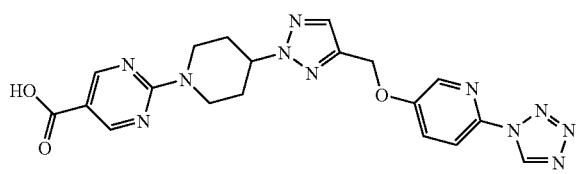

Ethyl 4-(2-(4-(4-((6-(1H-tetrazol-1-yl)pyridin-3-yloxy)methyl)-2H-1,2,3-triazol-2-yl)piperidin-1-yl)pyrimidine-5-carboxylate (0.8 g, 0.00167 mol) (Example 60) was dissolved in MeOH (20 mL). An aqueous solution of NaOH (10 eq., 40 mL) was added and the reaction mixture was heated at 60° C. for three hours. The methanol was removed in vacuo and the remaining reaction mixture was cooled to 0° C. and concentrated HCl was added drop wise until the pH reached 2-3. The aqueous solution was extracted with DCM, dried over sodium sulfate, filtered, and concentrated in vacuo to afford the title compound.

Step 2: Preparation of 2-(4-(4-((6-(1H-tetrazol-1-yl)pyridin-3-yloxy)methyl)-2H-1,2,3-triazol-2-yl)piperidin-1-yl)pyrimidin-5-yl)(morpholino)methanone

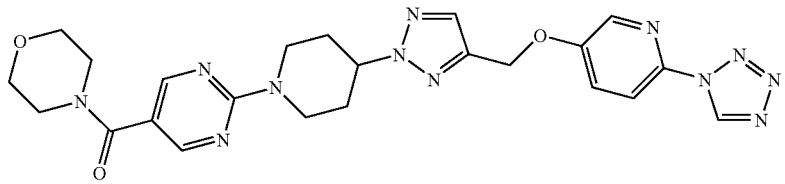

The title compound was prepared from 2-(4-(4-((6-(1H-tetrazol-1-yl)pyridin-3-yloxy)methyl)-2H-1,2,3-triazol-2-yl)piperidin-1-yl)pyrimidine-5-carboxylic acid (Step 1) in a manner similar to that described in Example 50 above. $^1$H NMR (CDCl$_3$): δ 9.44 (1H, s), 8.46 (2H, s), 8.27 (1H, d), 8.02 (1H, d), 7.71 (1H, s), 7.58 (1H, dd), 5.27 (2H, s), 4.82 (3H, m), 3.72 (8H, m), 3.28 (2H, m), 2.30 (2H, m), 2.23 (2H, m). LCMS: (ES$^+$-MS found: 519.0).

Example 62

(4-(4-((6-(1H-tetrazol-1-yl)pyridin-3-yloxy)methyl)-2H-1,2,3-triazol-2-yl)piperidin-1-yl)(5-bromopyrimidin-2-yl)methanone

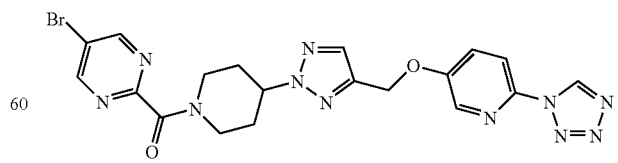

The title compound was prepared from 2-(4-(4-((6-(1H-tetrazol-1-yl)pyridin-3-yloxy)methyl)-2H-1,2,3-triazol-2-yl)piperidin-1-yl)pyrimidine-5-carboxylic acid (Example 61, Step 1) in a manner similar to that described in Example 50 above. LCMS: (ES$^+$-MS found: 512.0 & 514.0).

Example 63 tert-Butyl 4-(4-((6(1H-tetrazol-1-yl)pyridin-3-yloxy)methyl)-2H-1,2,3-triazol-2-yl)octahydroquinoline-1(2H)-carboxylate

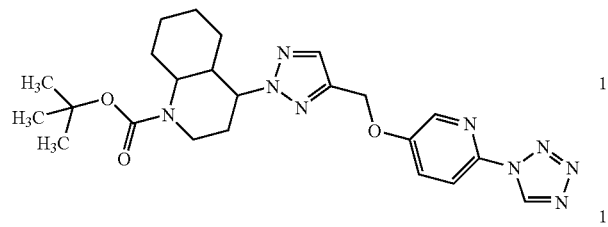

The title compound was prepared in a manner similar to that described in Example 59. $^1$H NMR (CDCl$_3$): δ 9.44 (1H, s), 8.25 (1H, s), 8.03 (1H, d), 7.65 (1H, s), 7.61 (1H, dd), 5.27 (2H, s), 4.93 (1H, m), 4.11-4.13 (1H, m), 3.40 (1H, m), 3.12 (1H, m), 2.49 (1H, m), 2.41 (1H, m), 2.15 (1H, m), 1.96 (1H, m), 1.50-1.74 (3H, m), 1.50 (9H, s), 1.08-1.34 (3H, m), 0.49 (1H, m).

Example 64

2-(4-(4-((2-Methyl-6-(1H-1,2,4-triazol-1-yl)pyridin-3-yloxy)methyl)-2H-1,2,3-triazol-2-yl)piperidin-1-yl)-5-(trifluoromethyl)pyrimidine

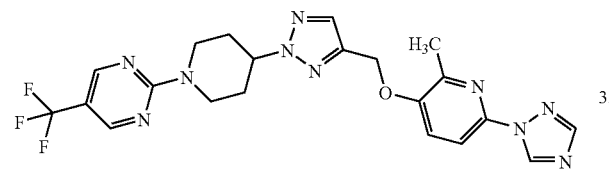

The title compound was prepared from Intermediate 26 and 2-methyl-6-(1H-1,2,4-triazol-1-yl)pyridin-3-ol in a manner similar to that described in Example 1. $^1$H NMR (CDCl$_3$): δ 9.08 (1H, s), 8.50 (2H, s), 8.06 (1H, s), 7.69 (1H, s), 7.67 (1H, m), 7.40 (1H, d), 5.21 (2H, s), 4.87-4.79 (3H, m), 3.31 (2H, m), 2.49 (3H, s), 2.29 (2H, m), 2.17 (2H, m). LCMS: (ES$^+$-MS found: 487.1).

Example 65

5-Ethyl-2-(4-(4-((2-methyl-6-(1H-1,2,4-triazol-1-yl)pyridin-3-yloxy)methyl)-2H-1,2,3-triazol-2-yl)piperidin-1-yl)pyrimidine

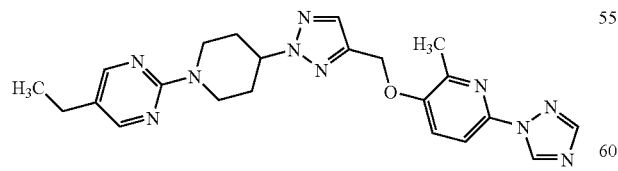

The title compound was prepared from Intermediate 30 and 2-methyl-6-(1H-1,2,4-triazol-1-yl)pyridin-3-ol in a manner similar to that described in Example 1 $^1$H NMR (CDCl$_3$): δ 9.07 (1H, s), 8.20 (2H, s), 8.05 (1H, s), 7.67 (1H, s), 7.65 (1H, d), 7.40 (1H, d), 5.20 (2H, s), 4.79-4.71 (3H, m), 3.18 (2H, m), 2.49 (2H, m), 2.48 (3H, s), 2.28 (2H, m), 2.21 (2H, m), 1.20 (3H, m). LCMS: (ES$^+$-MS found: 446.8).

Example 66

5-Ethyl-2-(4-(4-((2-fluoro-4-(1H-tetrazol-1-yl)phenoxy)methyl)-3-(trifluoromethyl)-1H-pyrazol-1-yl)piperidin-1-yl)pyrimidine

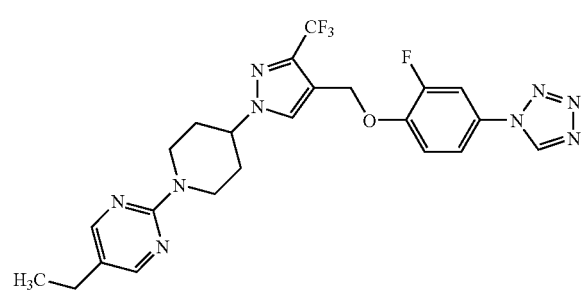

Step 1: Ethyl 1-(1-(5-ethylpyrimidin-2-yl)piperidin-4-yl)-3-(trifluoromethyl)-1H-pyrazole-4-carboxylate

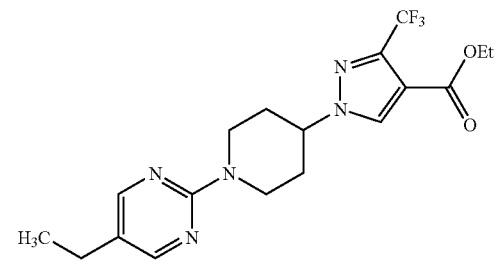

The compound was synthesized using ethyl 3-(trifluoromethyl)-1H-pyrazole-4-carboxylate and 1-(5-ethylpyrimidin-2-yl)piperidin-4-yl methanesulfonate in a manner similar to that described in Intermediate 1, Step 1. The reaction afforded two regioisomers, ethyl 1-(1-(5-ethylpyrimidin-2-yl)piperidin-4-yl)-3-(trifluoromethyl)-1H-pyrazole-4-carboxylate and ethyl 1-(1-(5-ethylpyrimidin-2-yl)piperidin-4-yl)-5-(trifluoromethyl)-1H-pyrazole-4-carboxylate which were separated by flash column chromatography on silica gel.

Step 2: (1-(1-(5-Ethylpyrimidin-2-yl)piperidin-4-yl)-3-(trifluoromethyl)-1H-pyrazol-4-yl)methanol

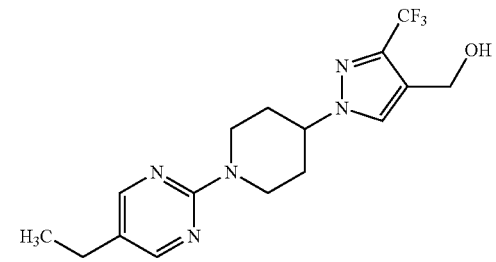

The compound was synthesized using ethyl 1-(1-(5-Ethylpyrimidin-2-yl)piperidin-4-yl)-3-(trifluoromethyl)-1H- pyrazole-4-carboxylate and sodium borohydride in a manner similar to that described in *Journal of Medicinal Chemistry*, 1996, 29, 341.

Step 3: (1-(1-(5-Ethylpyrimidin-2-yl)piperidin-4-yl)-3-(trifluoromethyl)-1H-pyrazol-4-yl)methyl methanesulfonate

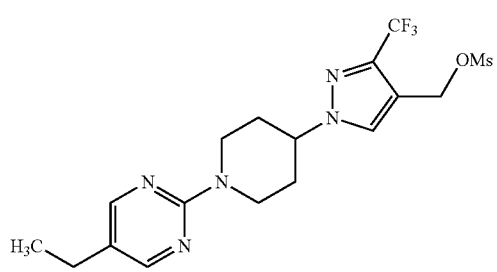

The title compound was synthesized using (1-(1-(5-ethylpyrimidin-2-yl)piperidin-4-yl)-3-(trifluoromethyl)-1H-pyrazol-4-yl)methanol in a manner similar to that described in Intermediate 1, Step 3.

Step 4: 5-Ethyl-2-(4-(4-((2-fluoro-4-(1H-tetrazol-1-yl)phenoxy)methyl)-3-(trifluoromethyl)-1H-pyrazol-1-yl)piperidin-1-yl)pyrimidine

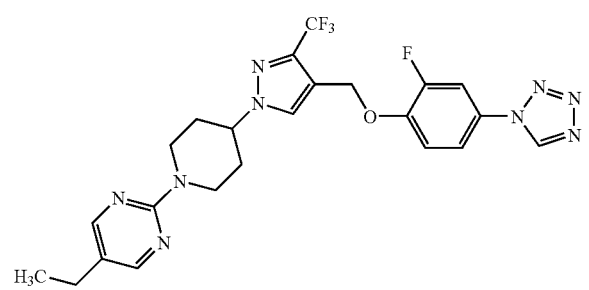

The compound was synthesized using (1-(1-(5-ethylpyrimidin-2-yl)piperidin-4-yl)-3-(trifluoromethyl)-1H-pyrazol-4-yl)methyl methanesulfonate and 2-fluoro-4-(1H-tetrazol-1-yl)phenol in a manner similar to that described in Example 1. $^1$H NMR (CDCl$_3$): δ 8.99 (1H, s), 8.15 (2H, s), 7.64 (1H, s), 7.50 (1H, m), 7.41 (1H, m), 7.17 (1H, m), 5.13 (2H, s), 4.86 (2H, m), 4.42 (1H, m), 2.99 (2H, m), 2.44 (2H, q), 2.20 (2H, m), 1.93 (2H, m), 1.16 (3H, t).

Example 67

5-Ethyl-2-(4-(4-((2-fluoro-4-(methylsulfonyl)phenoxy)methyl)-3-(trifluoromethyl)-1H-pyrazol-1-yl)piperidin-1-yl)pyrimidine

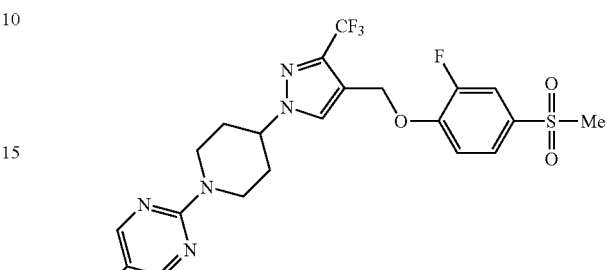

The compound was synthesized using (1-(1-(5-ethylpyrimidin-2-yl)piperidin-4-yl)-3-(trifluoromethyl)-1H-pyrazol-4-yl)methyl methanesulfonate and 2-fluoro-4-(methylsulfonyl)phenol in a manner similar to that described in Example 1. $^1$H NMR (CDCl$_3$): δ 8.25 (2H, s), 8.17 (1H, s), 7.71 (2H, m), 7.52 (1H, m), 5.30 (2H, s), 4.90 (2H, m), 4.65 (1H, m), 3.13 (3H, s), 3.05 (2H, m), 2.47 (2H, q), 2.20 (2H, m), 1.98 (2H, m), 1.18 (3H, t).

Example 68

5-Ethyl-2-(4-(4-((2-fluoro-4-(1H-tetrazol-1-yl)phenoxy)methyl)-5-(trifluoromethyl)-1H-pyrazol-1-yl)piperidin-1-yl)pyrimidine

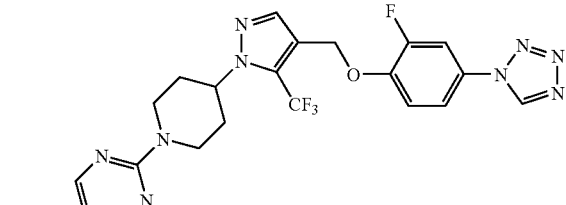

Step 1: ethyl 1-(1-(5-ethylpyrimidin-2-yl)piperidin-4-yl)-5-(trifluoromethyl)-1H-pyrazole-4-carboxylate

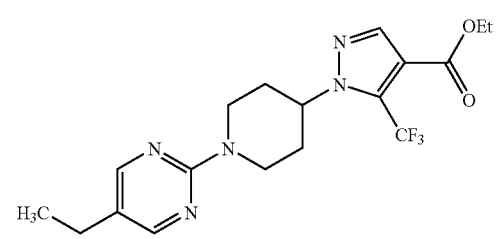

The title compound was obtained in Example 66, Step 1.

Step 2: (1-(1-(5-Ethylpyrimidin-2-yl)piperidin-4-yl)-5-(trifluoromethyl)-1H-pyrazol-4-yl)methanol

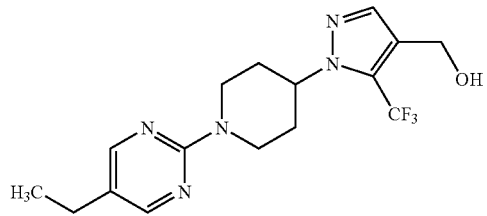

The title compound was synthesized using ethyl 1-(1-(5-ethylpyrimidin-2-yl)piperidin-4-yl)-5-(trifluoromethyl)-1H-pyrazole-4-carboxylate and sodium borohydride in a manner similar to that described in Example 66, Step 2.

Step 3: 2-(4-(4-(chloromethyl)-5-(trifluoromethyl)-1H-pyrazol-1-yl)piperidin-1-yl)-5-ethylpyrimidine

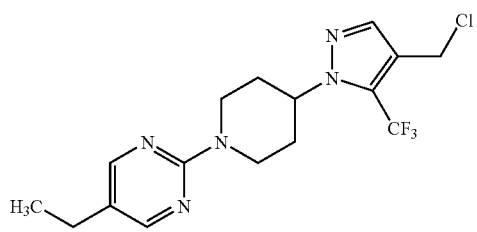

To a solution (1-(1-(5-ethylpyrimidin-2-yl)piperidin-4-yl)-5-(trifluoromethyl)-1H-pyrazol-4-yl)methanol (0.13 g, 0.366 mmol) in dichloromethane (3 mL) was added thionyl chloride (1.2 mL) and the solution was stirred at room temperature for 2 h. The reaction was concentrated in vacuo and the crude product was used in the next step without further purification.

Step 4: 5-Ethyl-2-(4-(4-((2-fluoro-4-(1H-tetrazol-1-yl)phenoxy)methyl)-5-(trifluoromethyl)-1H-pyrazol-1-yl)piperidin-1-yl)pyrimidine

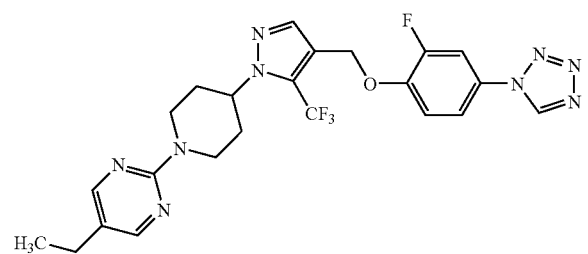

The title compound was synthesized using 2-(4-(4-(chloromethyl)-5-(trifluoromethyl)-1H-pyrazol-1-yl)piperidin-1-yl)-5-ethylpyrimidine and 2-fluoro-4-(1H-tetrazol-1-yl)phenol in manner similar to that described in Example 1. $^1$H NMR (CDCl$_3$): δ 8.95 (1H, s), 8.18 (2H, s), 7.64 (1H, s), 7.52 (1H, m), 7.43 (1H, m), 7.19 (1H, m), 5.16 (2H, s), 4.92 (2H, m), 4.50 (1H, m), 3.02 (2H, m), 2.47 (2H, q), 2.22 (2H, m), 2.01 (2H, m), 1.19 (3H, t).

Example 69

5-Chloro-2-(4-(4-((2-fluoro-4-(1H-tetrazol-1-yl)phenoxy)methyl)-2H-1,2,3-triazol-2-yl)-2-methylpiperidin-1-yl)pyrimidine

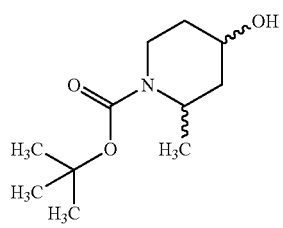

Step 1: tert-Butyl 4-hydroxy-2-methylpiperidine-1-carboxylate

To a solution of tert-butyl 2-methyl-4-oxopiperidine-1-carboxylate (0.94 g, 4.41 mmol) in methanol (5 mL) was added sodium borohydride (0.22 g, 5.73 mmol) and the reaction was stirred at room temperature for 1 h. Water was added slowly, followed by ethyl acetate. The layers were separated and the aqueous phase was extracted with ethyl acetate. The combined organic phases were dried over sodium sulfate, filtered and concentrated in vacuo to afford the desired product as a mixture of four stereoisomers, which was used in the next step without further purification.

Step 2: tert-Butyl 4-(4-((2-fluoro-4-(1H-tetrazol-1-yl)phenoxy)methyl)-2H-1,2,3-triazol-2-yl)-2-methylpiperidine-1-carboxylate The title compound was synthesized from tert-butyl 4-hydroxy-2-methylpiperidine-1-carboxylate and 1-(4-((2H-1,2,3-triazol-4-yl)methoxy)-3-fluorophenyl)-1H-tetrazole (Intermediate 16) in a manner similar to that described in Example 48, Step 4. The title compound was isolated as a mixture of four stereoisomers.

Step 3: 4-(4-((2-fluoro-4-(1H-tetrazol-1-yl)phenoxy)methyl)-2H-1,2,3-triazol-2-yl)-2-methylpiperidine hydrochloride

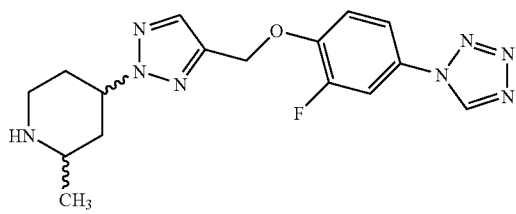

The title compound was synthesized from tert-butyl 4-(4-((2-fluoro-4-(1H-tetrazol-1-yl)phenoxy)methyl)-2H-1,2,3-triazol-2-yl)-2-methylpiperidine-1-carboxylate in a manner similar to that described in Intermediate 6. The title compound was isolated as a mixture of four stereoisomers.

Step 4: 5-Chloro-2-(4-(4-((2-fluoro-4-(1H-tetrazol-1-yl)phenoxy)methyl)-2H-1,2,3-triazol-2-yl)-2-methylpiperidin-1-yl)pyrimidine

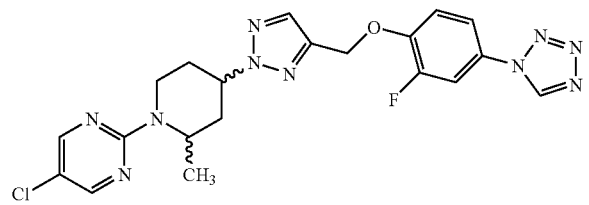

The title compound was synthesized from 4-(4-((2-fluoro-4-(1H-tetrazol-1-yl)phenoxy)methyl)-2H-1,2,3-triazol-2-yl)-2-methylpiperidine hydrochloride and 6-chloro-2-iodopyrimidine in a manner similar to that described in Example 9. The title compound was isolated as a mixture of four stereoisomers.

Example 70

2-(4-(4-((2-Fluoro-4-(1H-tetrazol-1-yl)phenoxy)methyl)-2H-1,2,3-triazol-2-yl)-2-methylpiperidin-1-yl)-5-(trifluoromethyl)pyrimidine

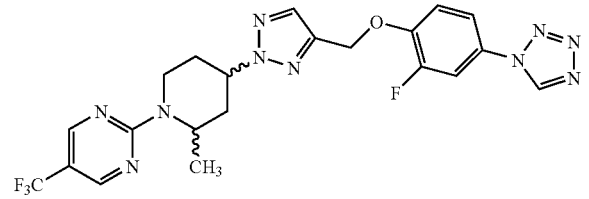

The title compound was synthesized from 4-(4-((2-fluoro-4-(1H-tetrazol-1-yl)phenoxy)methyl)-2H-1,2,3-triazol-2-yl)-2-methylpiperidine hydrochloride and 2-(methylsulfonyl)-5-(trifluoromethyl)pyrimidine in a manner similar to that described in Example 9. The title compound was isolated as a mixture of four stereoisomers.

Example 71 exo-3-(4-((6-(1H-Tetrazol-1-yl)pyridin-3-yloxy)methyl)-2H-1,2,3-triazol-2-yl)-8-(5-(trifluoromethyl)pyrimidin-2-yl)-8-azabicyclo[3.2.1]octane

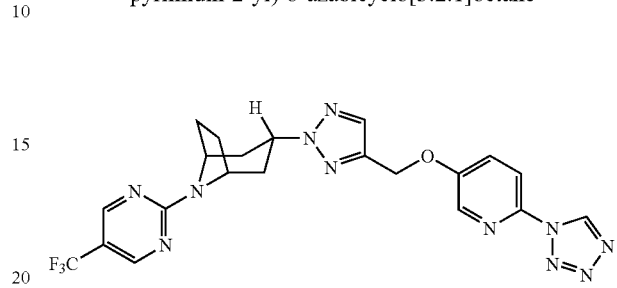

Step 1: 8-(5-(trifluoromethyl)pyrimidin-2-yl)-8-azabicyclo[3.2.1]octan-3-one

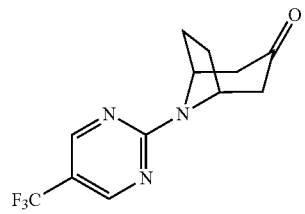

The title compound was synthesized from 2-(methylsulfonyl)-5-(trifluoromethyl)pyrimidine and 8-azabicyclo[3.2.1]octan-3-one in a manner similar to that described in Example 9.

Step 2: endo-8-(5-(trifluoromethyl)pyrimidin-2-yl)-8-azabicyclo[3.2.1]octan-3-ol

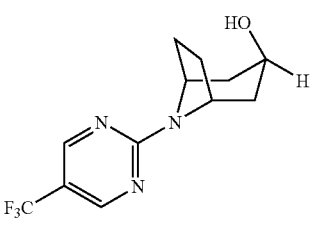

The title compound was synthesized from 8-(5-(trifluoromethyl)pyrimidin-2-yl)-8-azabicyclo[3.2.1]octan-3-one in a manner similar to that described in Example 69, Step 1 to afford endo and exo 8-(5-(trifluoromethyl)pyrimidin-2-yl)-8-azabicyclo[3.2.1]octan-3-ol. The two compounds were separated by flash column chromatography on silica gel eluting with 0-100% ethyl acetate in hexanes.

Step 3: exo-3-(4-((6-(1H-tetrazol-1-yl)pyridin-3-yloxy)methyl)-2H-1,2,3-triazol-2-yl)-8-(5-(trifluoromethyl)pyrimidin-2-yl)-8-azabicyclo[3.2.1]octane

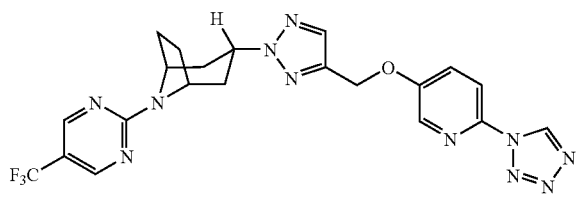

The title compound was synthesized from 8-(5-(trifluoromethyl)pyrimidin-2-yl)-8-azabicyclo[3.2.1]octan-3-ol and 5-((2H-1,2,3-triazol-4-yl)methoxy)-2-(1H-tetrazol-1-yl)pyridine (Intermediate 13) in a manner similar to that described in Example 48, Step 4. $^1$H NMR (CDCl$_3$): δ 9.42 (1H, s), 8.51 (2H, s), 8.23 (1H, d), 8.00 (1H, d), 7.65 (1H, s), 7.54 (1H, m), 5.22 (2H, s), 5.15 (1H, m), 5.00 (2H, s), 2.40-1.90 (8H, m).

Example 72 endo-tert-Butyl 3-(4-((6-(1H-tetrazol-1-yl)pyridin-3-yloxy)methyl)-2H-1,2,3-triazol-2-yl)-8-azabicyclo[3.2.1]octane-8-carboxylate

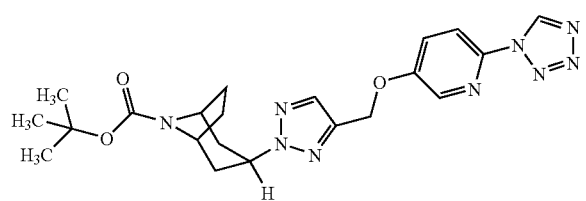

Step 1: tert-Butyl 3-oxo-8-azabicyclo[3.2.1]octane-8-carboxylate

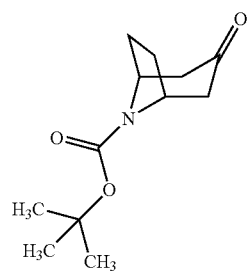

The title compound was synthesized from 8-azabicyclo[3.2.1]octan-3-one hydrochloride and di-tert-butyl dicarbonate in a manner similar to that described in *Journal of Organic Chemistry* 2005, 70, 10872-10874

Step 2: exo-tert-Butyl 3-hydroxy-8-azabicyclo[3.2.1]octane-8-carboxylate

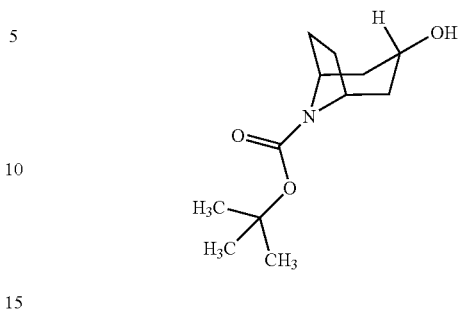

The title compound was synthesized from tert-butyl 3-oxo-8-azabicyclo[3.2.1]octane-8-carboxylate in a manner similar to that described in Example 69, Step 2.

Step 3: endo-tert-Butyl 3-(4-((6-(1H-tetrazol-1-yl)pyridin-3-yloxy)methyl)-2H-1,2,3-triazol-2-yl)-8-azabicyclo[3.2.1]octane-8-carboxylate

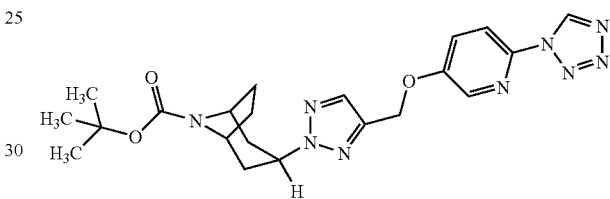

The title compound was synthesized from exo-tert-butyl 3-hydroxy-8-azabicyclo[3.2.1]octane-8-carboxylate and 5-((2H-1,2,3-triazol-4-yl)methoxy)-2-(1H-tetrazol-1-yl)pyridine (Intermediate 13) in a manner similar to that described in Example 48, Step 4. $^1$H NMR (CDCl$_3$): δ 9.46 (1H, s), 8.29 (1H, d), 8.02 (1H, d), 7.75 (1H, s), 7.62 (1H, dd), 5.33 (2H, s), 4.64 (1H, m), 4.26 (2H, m), 2.97 (2H, m), 2.43 (2H, m), 1.77 (2H, m), 1.50 (9H, s), 1.38 (2H, m).

Example 73 exo-tert-Butyl 3-(4-((6-(1H-tetrazol-1-yl)pyridin-3-yloxy)methyl)-2H-1,2,3-triazol-2-yl)-8-azabicyclo[3.2.1]octane-8-carboxylate

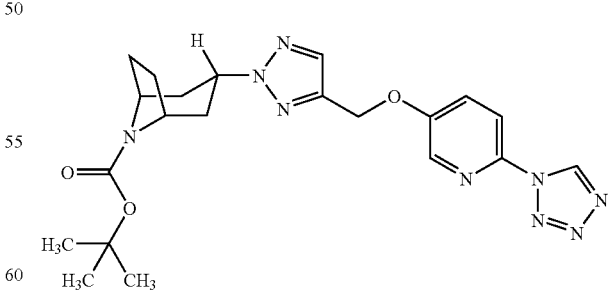

The title compound was synthesized from endo-tert-butyl 3-hydroxy-8-azabicyclo[3.2.1]octane-8-carboxylate and 5-((2H-1,2,3-triazol-4-yl)methoxy)-2-(1H-tetrazol-1-yl)pyridine (Intermediate 13) in a manner similar to that described in Example 48, Step 4. $^1$H NMR (CDCl$_3$): δ 9.48 (1H, s), 8.28

(1H, d), 8.02 (1H, d), 7.71 (1H, s), 7.63 (1H, m), 5.30 (2H, s), 5.02 (1H, m), 4.39 (2H, m), 2.40-1.85 (8H, m), 1.51 (9H, s).

Example 74 endo-3-(4-((6-(1H-tetrazol-1-yl)pyridin-3-yloxy)methyl)-2H-1,2,3-triazol-2-yl)-8-(5-fluoropyrimidin-2-yl)-8-azabicyclo[3.2.1]octane

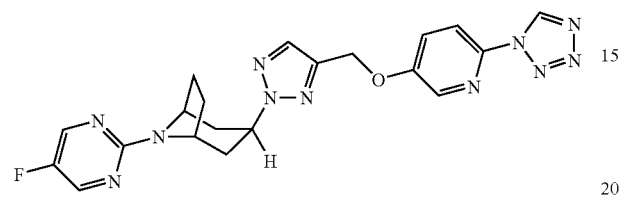

Step 1: endo-3-(4-((6-(1H-tetrazol-1-yl)pyridin-3-yloxy)methyl)-2H-1,2,3-triazol-2-yl)-8-azabicyclo[3.2.1]octane hydrochloride

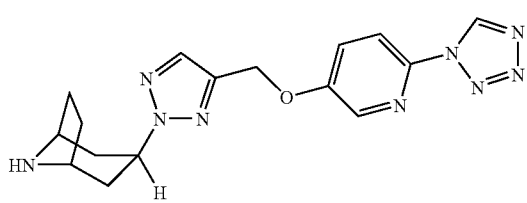

The title compound was synthesized from endo-tert-butyl 3-(4-((6-(1H-tetrazol-1-yl)pyridin-3-yloxy)methyl)-2H-1,2,3-triazol-2-yl)-8-azabicyclo[3.2.1]octane-8-carboxylate and 4N hydrochloric acid in dioxane in a manner similar to that described in Intermediate 6.

Step 2: endo-3-(4-((6-(1H-tetrazol-1-yl)pyridin-3-yloxy)methyl)-2H-1,2,3-triazol-2-yl)-8-(5-fluoropyrimidin-2-yl)-8-azabicyclo[3.2.1]octane

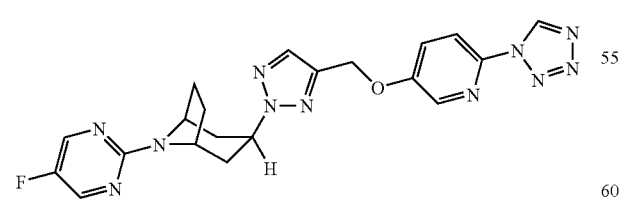

The compound was synthesized from endo-3-(4-((6-(1H-tetrazol-1-yl)pyridin-3-yloxy)methyl)-2H-1,2,3-triazol-2-yl)-8-azabicyclo[3.2.1]octane hydrochloride and 2-chloro-5-fluoro-pyrimidine in a manner similar to that described in Example 9. $^1$H NMR (CDCl$_3$): δ 9.45 (1H, s), 8.29 (1H, d), 8.25 (2H, s), 8.03 (1H, d), 7.75 (1H, s), 7.61 (1H, dd), 5.33 (2H, s), 4.59 (2H, s), 4.57 (1H, m), 3.01 (2H, m), 2.49 (2H, m), 1.88 (2H, m), 1.55 (2H, m).

Example 75 exo-3-(4-((6-(1H-Tetrazol-1-yl)pyridin-3-yloxy)methyl)-2H-1,2,3-triazol-2-yl)-8-(5-fluoropyrimidin-2-yl)-8-azabicyclo[3.2.1]octane

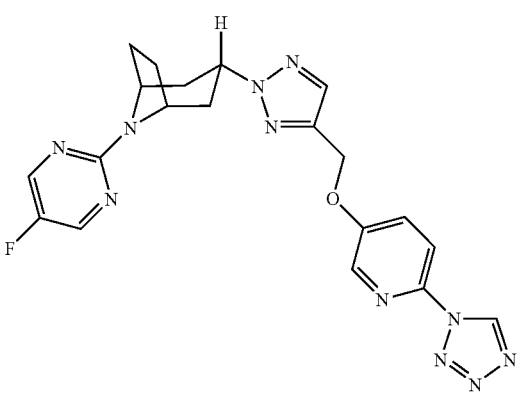

The title compound was synthesized in a manner similar to that described in Example 74. $^1$H NMR (CDCl$_3$): δ 9.45 (1H, s), 8.24 (3H, m), 8.01 (1H, m), 7.65 (1H, s), 7.56 (1H, m), 5.23 (2H, s), 5.14 (1H, m), 4.85 (2H, m), 2.40-1.95 (8H, m).

Example 76

Allyl 4-(4-((2-fluoro-4-(1H-tetrazol-1-yl)phenoxy)methyl)-2H-1,2,3-triazol-2-yl)piperidine-1-carboxylate

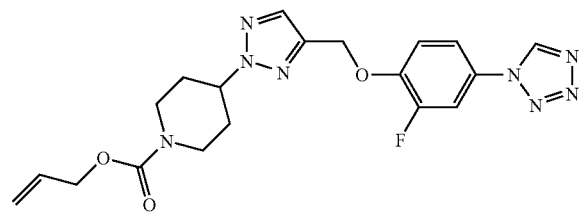

The title compound was synthesized from Intermediate 8 and allyl chloroformate in a manner similar to that described in *Journal of Medicinal Chemistry* 1998, 41, 4983-4994. $^1$H NMR (CDCl$_3$): δ 8.95 (1H, s), 7.72 (1H, s), 7.53 (1H, m), 7.45 (1H, m), 7.32 (1H, m), 5.95 (1H, m), 5.40-5.20 (4H, m), 4.64 (3H, m), 4.23 (2H, m), 3.09 (2H, m), 2.14 (4H, m).

Example 77

Allyl 4-(4-((6-(1H-tetrazol-1-yl)pyridin-3-yloxy)methyl)-2H-1,2,3-triazol-2-yl)piperidine-1-carboxylate

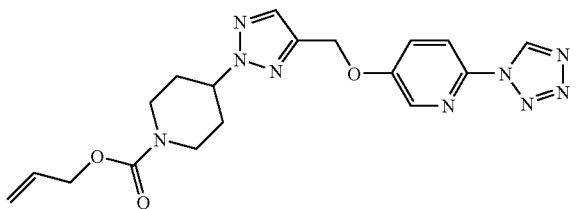

The title compound was synthesized from Intermediate 15 and allyl chloroformate in a manner similar to that described in *Journal of Medicinal Chemistry* 1998, 41, 4983-4994. $^1$H NMR (CDCl$_3$): δ 9.46 (1H, s), 8.28 (1H, m), 8.04 (1H, m), 7.73 (1H, s), 7.61 (1H, m), 5.95 (1H, m), 5.40-5.20 (4H, m), 4.64 (3H, m), 4.24 (2H, m), 3.10 (2H, m), 2.16 (4H, m).

The compounds in Examples 78-82 were synthesized from Intermediates 15 with the corresponding 2-fluoropyrimidine, 2-chloropyrimidine, 2-bromopyrimidine, 2-iodopyrimidine, 2-(methylsulfinyl)pyrimidine, 2-(methylsulfonyl)pyrimidine or 2-chlorothiazole in a manner similar to that described in Example 9. One skilled in the art of organic synthesis will appreciate that conditions such as solvent (DMF, CH$_3$CN), temperature, base (NEt$_3$, $^i$Pr$_2$NEt, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 78

2-(4-(4-((6-(1H-tetrazol-1-yl)pyridin-3-yloxy)methyl)-2H-1,2,3-triazol-2-yl)piperidin-1-yl)-5-pentylpyrimidine

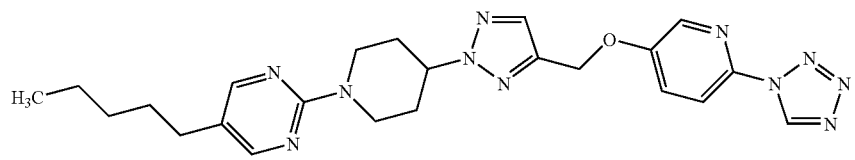

$^1$H NMR (CDCl$_3$): δ 8.17 (2H, s), 7.76 (1H, s), 7.66 (1H, s), 7.42 (1H, m), 7.27 (1H, s), 7.07 (1H, m), 5.12 (2H, s), 4.78 (3H, m), 3.16 (2H, m), 2.42 (2H, m), 2.25 (2H, m), 2.16 (2H, m), 1.28 (6H, m), 0.88 (3H, m).

Example 79

Methyl 2-(4-(4-((6-(1H-tetrazol-1-yl)pyridin-3-yloxy)methyl)-2H-1,2,3-triazol-2-yl)piperidin-1-yl)-6-methylpyrimidine-4-carboxylate

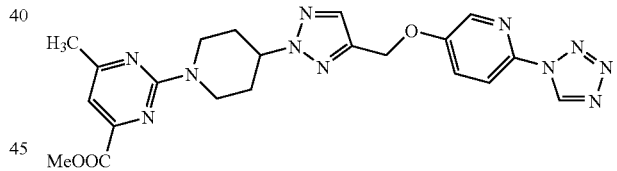

$^1$H NMR (CDCl$_3$): δ 9.44 (1H, s), 8.27 (1H, s), 8.02 (1H, m), 7.70 (1H, s), 7.59 (1H, m), 7.05 (1H, s), 5.28 (2H, s), 4.92 (2H, m), 4.75 (1H, m), 3.95 (3H, s), 3.21 (2H, m), 2.43 (3H, s), 2.28 (2H, m), 2.17 (2H, m).

Example 80

2-(4-(4-((6-(1H-tetrazol-1-yl)pyridin-3-yloxy)methyl)-2H-1,2,3-triazol-2-yl)piperidin-1-yl)-5-(4-methoxyphenyl)pyrimidine

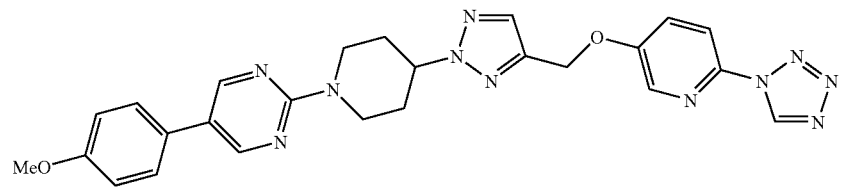

¹H NMR (CDCl₃): δ 9.44 (1H, s), 8.53 (2H, s), 8.27 (1H, d), 8.03 (1H, d), 7.71 (1H, s), 7.59 (1H, dd), 7.41 (2H, d), 6.98 (2H, d), 5.28 (2H, s), 4.86 (2H, m), 4.76 (1H, m), 3.85 (3H, s), 3.25 (2H, m), 2.29 (2H, m), 2.21 (2H, m).

Example 81

Ethyl 2-(4-(4-((6-(1H-tetrazol-1-yl)pyridin-3-yloxy)methyl)-2H-1,2,3-triazol-2-yl)piperidin-1-yl)thiazole-5-carboxylate

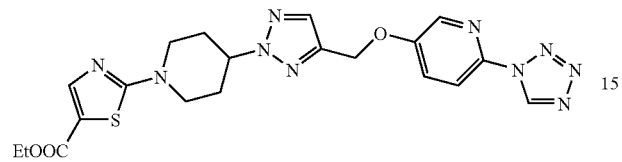

¹H NMR (CDCl₃): δ 9.44 (1H, s), 8.27 (1H, d), 8.03 (1H, d), 7.87 (1H, s), 7.73 (1H, s), 7.58 (1H, dd), 5.28 (2H, s), 4.76 (1H, m), 4.30 (2H, q), 4.13 (2H, m), 3.39 (2H, m), 3.33 (4H, m), 1.34 (3H, t).

Example 82

2-(4-(4-((6-(1H-tetrazol-1-yl)pyridin-3-yloxy)methyl)-2H-1,2,3-triazol-2-yl)piperidin-1-yl)-5-(trifluoromethyl)pyridine

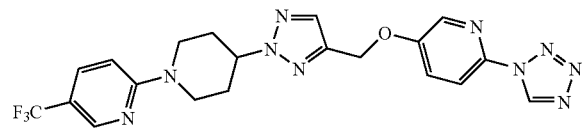

¹H NMR (CDCl₃): δ 9.44 (1H, s), 8.41 (1H, s), 8.27 (1H, d), 8.03 (1H, d), 7.71 (1H, s), 7.65 (1H, d), 7.58 (1H, dd), 6.72 (1H, d), 5.28 (2H, s), 4.77 (1H, m), 4.47 (2H, m), 3.23 (2H, m), 2.30 (2H, m), 2.20 (2H, m).

Example 83 tert-Butyl 4-(4-((6-(1H-tetrazol-1-yl)pyridin-3-yloxy)methyl)-2H-1,2,3-triazol-2-yl)-3-methylpiperidine-1-carboxylate

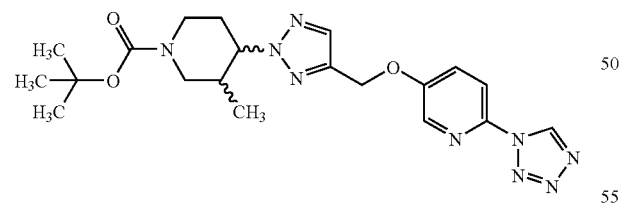

The title compound was synthesized from Intermediate 13 and tert-butyl 4-hydroxy-3-methylpiperidine-1-carboxylate in a manner similar to that described in Example 69. The compounds were isolated as a mixture of four stereoisomers. Characterized by LCMS (ES⁺-MS found: 464 (M+Na), 442 (M+H)).

The compounds in Examples 84-87 were synthesized from Intermediate 21 with the corresponding substituted 2-fluoropyrimidine, 2-chloropyrimidine, 2-bromopyrimidine, 2-iodopyrimidine, 2-(methylsulfinyl)pyrimidine, 2-(methylsulfonyl)pyrimidine or 2-chlorothiazole in a manner similar to that described in Example 9. One skilled in the art of organic synthesis will appreciate that conditions such as solvent (DMF, CH₃CN), temperature, base (NEt₃, ⁱPr₂NEt, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 84

2-(4-(4-((6-(1H-Tetrazol-1-yl)pyridin-3-yloxy)methyl)-2H-1,2,3-triazol-2-yl)-3-methylpiperidin-1-yl)-5-(trifluoromethyl)pyrimidine

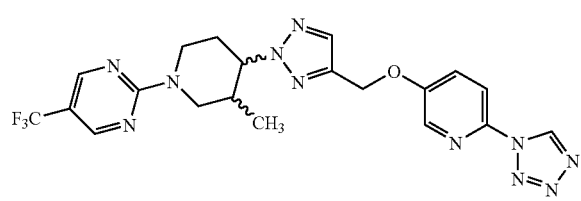

The compounds were isolated as a mixture of four stereoisomers. LCMS: (ES+-MS found: 488).

Example 85

2-(4-(4-((6-(1H-Tetrazol-1-yl)pyridin-3-yloxy)methyl)-2H-1,2,3-triazol-2-yl)-3-methylpiperidin-1-yl)-5-ethylpyrimidine

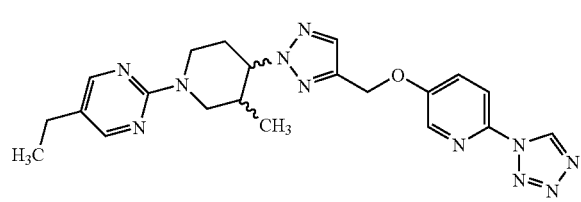

The compounds were isolated as a mixture of four stereoisomers. LCMS: (ES⁺-MS found: 448).

Example 86

2-(4-(4-((6-(1H-Tetrazol-1-yl)pyridin-3-yloxy)methyl)-2H-1,2,3-triazol-2-yl)-3-methylpiperidin-1-yl)-5-methylpyrimidine

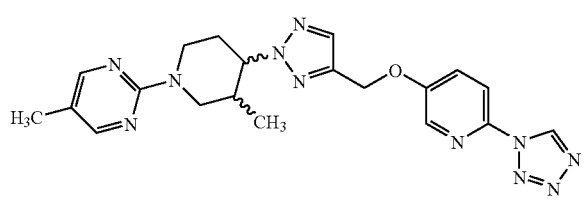

The compounds were isolated as a mixture of four stereoisomers. LCMS: (ES⁺-MS found: 434).

Example 87

2-(4-(4-((6-(1H-Tetrazol-1-yl)pyridin-3-yloxy)methyl)-2H-1,2,3-triazol-2-yl)-3-methylpiperidin-1-yl)-5-chloropyrimidine

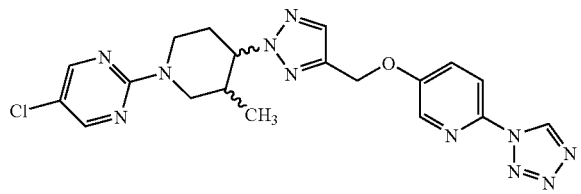

The compounds were isolated as a mixture of four stereoisomers. LCMS: (ES$^+$-MS found: 454).

The compounds in Examples 88-98 were synthesized from (2-(1-(5-chloropyrimidin-2-yl)piperidin-4-yl)-2H-1,2,3-triazol-4-yl)methyl methanesulfonate (Intermediate 24) and the corresponding phenol, pyrazol-3-ol or thiazol-2-ol in a similar manner to that described in Example 1. One skilled in the art of organic synthesis will appreciate that conditions such as solvent (DMF, CH$_3$CN); temperature, base (NEt$_3$, $^i$Pr$_2$NEt, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 88

2-(4-(4-((4-(1H-Tetrazol-1-yl)phenoxy)methyl)-2H-1,2,3-triazol-2-yl)piperidin-1-yl)-5-chloropyrimidine

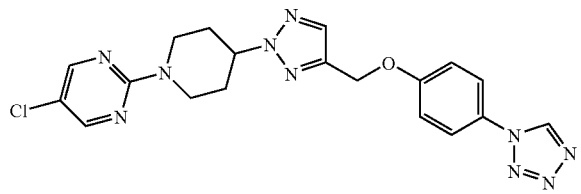

$^1$H NMR (CDCl$_3$): δ 8.90 (1H, s), 8.24 (2H, s), 7.68 (1H, s), 7.61 (2H, d), 7.16 (2H, d), 5.21 (2H, s), 4.75 (3H, m), 3.21 (2H, m), 2.26 (2H, m), 2.17 (2H, m).

Example 89

5-chloro-2-(4-(4-((2-Methyl-4-(1H-tetrazol-1-yl)phenoxy)methyl)-2H-1,2,3-triazol-2-yl)piperidin-1-yl)pyrimidine

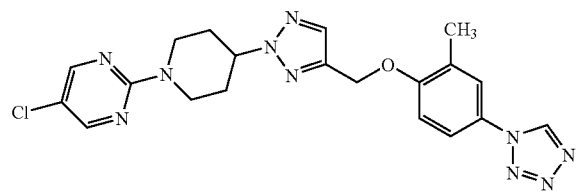

$^1$H NMR (CDCl$_3$): δ 8.91 (1H, s), 8.21 (2H, s), 7.66 (1H, s), 7.45 (2H, m), 7.07 (1H, m), 5.21 (2H, s), 4.72 (3H, m), 3.19 (2H, m), 2.26 (5H, m), 2.15 (2H, m).

Example 90

2-((2-(1-(5-Chloropyrimidin-2-yl)piperidin-4-yl)-2H-1,2,3-triazol-4-yl)methoxy)-5-methyl-4-(pyridin-3-yl)thiazole

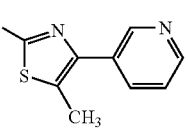

$^1$H NMR (CDCl$_3$): δ 8.58 (2H, m), 8.17 (2H, s), 7.63 (2H, m), 7.60 (1H, s), 5.42 (2H, s), 4.66 (3H, m), 3.14 (2H, m), 2.26 (3H, s), 2.18 (2H, m), 2.11 (2H, m).

Example 91

2-((2-(1-(5-Chloropyrimidin-2-yl)piperidin-4-yl)-2H-1,2,3-triazol-4-yl)methoxy)-5-methyl-4-(pyridin-4-yl)thiazole

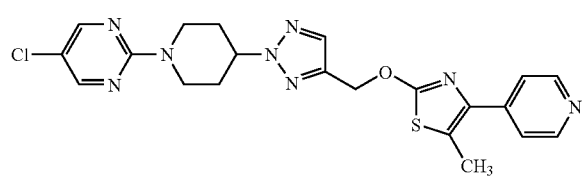

The title compound was isolated as a TFA salt. $^1$H NMR (CDCl$_3$): δ 8.78 (2H, m), 8.24 (2H, s), 8.09 (2H, m), 7.66 (1H, s), 5.52 (2H, s), 4.75 (1H, br.s), 4.71 (3H, m), 3.21 (2H, m), 2.38 (3H, s), 2.24 (2H, m), 2.15 (2H, m).

Example 92

2-(4-(4-((4-(1H-1,2,3-Triazol-1-yl)phenoxy)methyl)-2H-1,2,3-triazol-2-yl)piperidin-1-yl)-5-chloropyrimidine

$^1$H NMR (CDCl$_3$): δ 8.23 (2H, s), 7.91 (1H, s), 7.82 (1H, s), 7.68 (1H, s), 7.64 (2H, d), 7.11 (2H, d), 5.19 (2H, s), 4.72 (3H, m), 3.20 (2H, m), 2.25 (2H, m), 2.14 (2H, m).

Example 93

2-(4-(4-((4-(1H-1,2,4-Triazol-1-yl)phenoxy)methyl)-2H-1,2,3-triazol-2-yl)piperidin-1-yl)-5-chloropyrimidine

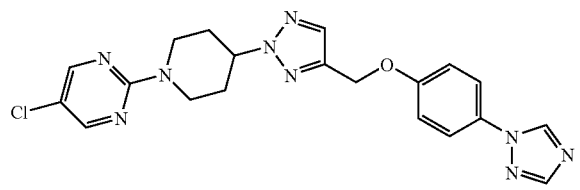

¹H NMR (CDCl₃): δ 8.45 (1H, s), 8.22 (2H, s), 8.07 (1H, s), 7.67 (1H, s), 7.56 (2H, d), 7.08 (2H, d), 5.17 (2H, s), 4.72 (3H, m), 3.19 (2H, m), 2.24 (2H, m), 2.13 (2H, m).

Example 94

2-(4-(4-((4-(1H-Imidazol-1-yl)phenoxy)methyl)-2H-1,2,3-triazol-2-yl)piperidin-1-yl)-5-chloropyrimidine

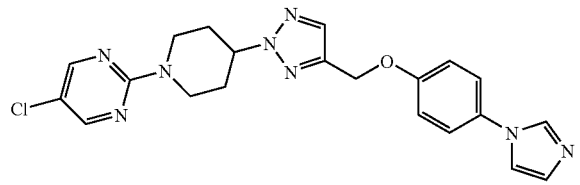

¹H NMR (CDCl₃): δ 8.73 (1H, s), 8.24 (2H, s), 7.68 (1H, s), 7.48 (1H, s), 7.40 (1H, s), 7.36 (2H, d), 7.15 (2H, d), 5.20 (2H, s), 4.74 (3H, m), 3.21 (2H, m), 2.25 (2H, m), 2.17 (2H, m).

Example 95

5-Chloro-2-(4-(4-((4-(Methylsulfonyl)phenoxy)methyl)-2H-1,2,3-triazol-2-yl)piperidin-1-yl)pyrimidine

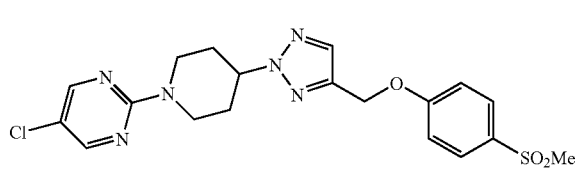

¹H NMR (CDCl₃): δ 8.24 (2H, s), 7.87 (2H, d), 7.67 (1H, s), 7.11 (2H, d), 5.21 (2H, s), 4.71 (3H, m), 3.20 (2H, m), 3.03 (3H, s), 2.25 (2H, m), 2.14 (2H, m).

Example 96

5-Chloro-2-{4-[4-(2-[1,3,4]oxadiazol-2-yl-phenoxymethyl)-[1,2,3]triazol-2-yl]-piperidin-1-yl}-pyrimidine

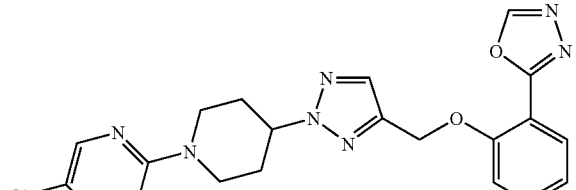

¹H NMR (DMSO-d₆): δ 9.31 (1H, s), 8.43 (2H, s), 7.87-7.85 (2H), 7.60 (1H, t, J=7.4 Hz), 7.42 (1H, d, J=8.4 Hz), 7.15 (1H, t, J=7.6 Hz), 5.32 (2H, s), 4.84-4.82 (1H, m), 4.57-4.53 (2H, m), 3.26-3.21 (2H, m), 2.18-2.14 (2H, m), 1.93-1.85 (2H, m).

Example 97

5-Chloro-2-{4-[4-(1-methyl-5-trifluoromethyl-1H-pyrazol-3-yloxymethyl)-[1,2,3]triazol-2-yl]-piperidin-1-yl}-pyrimidine

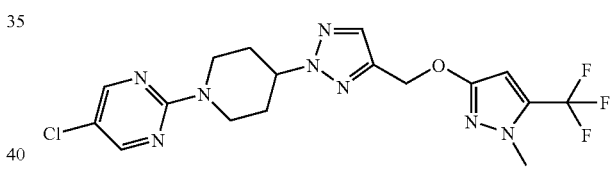

¹H NMR (DMSO-d₆): δ 8.43 (2H, s), 7.85 (1H, s), 6.41 (1H, s), 5.19 (2H, s), 4.88-4.83 (1H, m), 4.57-4.54 (2H, m), 3.26-3.20 (2H, m), 2.17-2.15 (2H, m), 1.93-1.85 (2H, m).

Example 98

5-Chloro-2-{4-[4-(6-chloro-pyridin-3-yloxymethyl)-[1,2,3]triazol-2-yl]-piperidin-1-yl}-pyrimidine

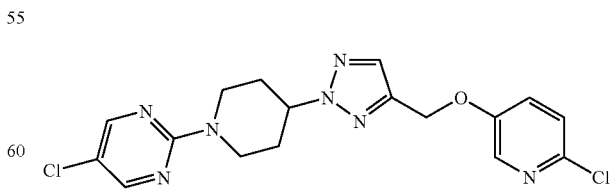

¹H NMR (DMSO-d₆): δ 8.42 (2H, s), 8.19 (1H, d, J=2.8 Hz), 7.89 (1H, s), 7.57 (1H, dd, J=2.8, 8.8 Hz), 7.43 (1H, d, J=8.8 Hz), 5.23 (2H, s), 4.89-4.84 (1H, m), 4.58-4.54 (2H, m), 3.26-3.20 (2H, m), 2.17-2.15 (2H, m), 1.94-1.85 (2H, m).

Example 99

1-(4-{2-[1-(5-Trifluoromethyl-pyrimidin-2-yl)-piperidin-4-yl]-2H-[1,2,3]triazol-4-ylmethoxy}-phenyl)-pyrrolidin-2-one

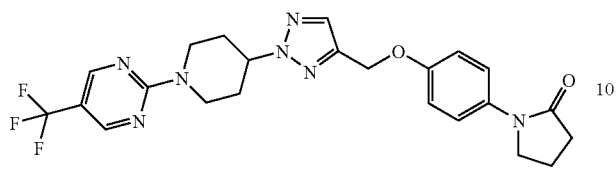

The title compound was synthesized from 1-(4-hydroxyphenyl)pyrrolidin-2-one and Intermediate 26 in a manner similar to that described in Example 1. $^1$H NMR (DMSO-d$_6$): δ 8.71 (2H, s), 7.86 (1H, s), 7.53 (2H, d, J=8.8 Hz), 7.01 (2H, d, J=8.8 Hz), 5.11 (2H, s), 4.93-4.86 (1H, m), 4.70-4.67 (2H, m), 3.76 (2H, t, J=6.8 Hz), 3.36-3.31 (2H, m), 2.43 (2H, t, J=8.0 Hz), 2.23-2.20 (2H, m), 2.06-1.87 (4H, m).

Example 100

Synthesis of 2-[4-(4-benzyloxymethyl-[1,2,3]triazol-2-yl)-piperidin-1-yl]-5-trifluoromethyl-pyrimidine

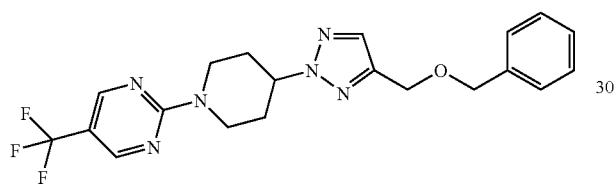

The title compound was synthesized from (2-(1-(5-(trifluoromethyl)pyrimidin-2-yl)piperidin-4-yl)-2H-1,2,3-triazol-4-yl)methanol (Intermediate 27) and benzyl alcohol in a manner similar to that described in Example 29. $^1$H NMR (CDCl$_3$): δ 8.50 (2H, s), 7.60 (1H, s), 7.36-7.30 (5H, m), 4.86-4.82 (2H, m), 4.79-4.72 (1H, m), 4.62 (2H, s), 4.59 (2H, s), 3.33-3.26 (2H, m), 2.30-2.16 (4H, m).

The compounds in Examples 101-104 were synthesized from one of Intermediates 7 or 8 with the corresponding chloroformate in a manner similar to that described in Example 35. One skilled in the art of organic synthesis will appreciate that conditions such as solvent (DMF, CH$_3$CN), temperature, base (NEt$_3$, $^i$Pr$_2$NEt, K$_2$CO$_3$, NaHCO$_3$, Na$_2$CO$_3$, Cs$_2$CO$_3$) and concentration can be selected through routine experimentation to optimize yields. Additionally, alternative coupling methods can be used that are well known in the art of organic synthesis.

Example 101

Isobutyl 4-(4-((2-fluoro-4-(1H-tetrazol-1-yl)phenoxy)methyl)-2H-1,2,3-triazol-2-yl)piperidine-1-carboxylate

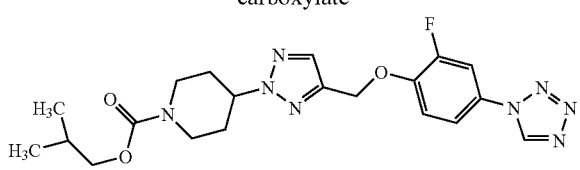

$^1$H NMR (CDCl$_3$): δ 8.92 (1H, s), 7.72 (1H, s), 7.51 (1H, m), 7.42 (1H, m), 7.30 (1H, m), 5.30 (2H, s), 4.64 (1H, m), 4.21 (2H, m), 3.89 (2H, d, J=6.80 Hz), 3.07 (2H, m), 2.10-2.18 (4H, m), 1.95 (1H, m), 0.95 (6H, t, d, J=6.80 Hz). LCMS: (ES$^+$-MS found: 445.3).

Example 102

Benzyl 4-(4-((2-fluoro-4-(1H-tetrazol-1-yl)phenoxy)methyl)-2H-1,2,3-triazol-2-yl)piperidine-1-carboxylate

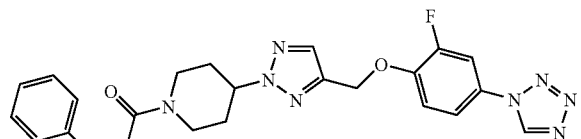

$^1$H NMR (CDCl$_3$): δ 8.92 (1H, s), 7.72 (1H, s), 7.51 (1H, m), 7.42 (1H, m), 7.29-7.38 (6H, m), 5.30 (2H, s), 5.15 (2H, s), 4.64 (1H, m), 4.23 (2H, m), 3.10 (2H, m), 2.10-2.18 (4H, m). LCMS: (ES$^+$-MS found: 479.1).

Example 103

Isobutyl 4-(4-((2-fluoro-4-(methylsulfonyl)phenoxy)methyl)-2H-1,2,3-triazol-2-yl)piperidine-1-carboxylate

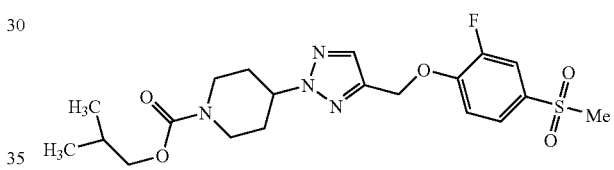

$^1$H NMR (CDCl$_3$): δ 7.65-7.70 (3H, m), 7.24-7.28 (1H, m), 5.30 (2H, s), 4.63 (1H, m), 4.22 (2H, m), 3.89 (2H, d, J=6.80 Hz), 3.07 (2H, m), 3.05 (3H, s), 2.10-2.21 (4H, m), 1.95 (1H, m), 0.95 (6H, t, d, J=6.80 Hz). LCMS: (ES$^+$-MS found: 455.3).

Example 104

Benzyl 4-(4-((2-fluoro-4-(methylsulfonyl)phenoxy)methyl)-2H-1,2,3-triazol-2-yl)piperidine-1-carboxylate

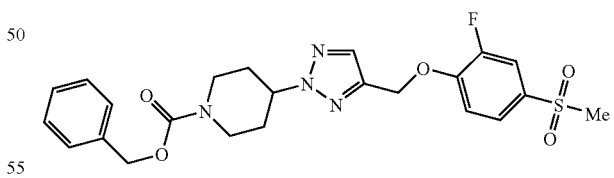

$^1$H NMR (CDCl$_3$): δ 7.65-7.70 (3H, m), 7.33-7.37 (4H, m), 7.24-7.28 (2H, m), 5.30 (2H, s), 5.15 (2H, s), 4.63 (1H, m), 4.23 (2H, m), 3.09 (2H, m), 3.04 (3H, s), 2.10-2.18 (4H, m). LCMS: (ES$^+$-MS found: 489.0).

The compounds in Examples 105-107 were synthesized from one of Intermediates 7 or 8 with the corresponding substituted 2-fluoropyrimidine, 2-chloropyrimidine, 2-bromopyrimidine, 2-iodopyrimidine, 2-(methylsulfinyl)pyrimidine or 2-(methylsulfonyl)pyrimidine in a manner similar to that described in Example 9. One skilled in the art of organic synthesis will appreciate that conditions such as solvent (DMF, CH₃CN), temperature, base (NEt₃, $^i$Pr₂NEt, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 105

Ethyl 2-(4-(4-((2-fluoro-4-(methylsulfonyl)phenoxy) methyl)-2H-1,2,3-triazol-2-yl)piperidin-1-yl)pyrimidine-5-carboxylate

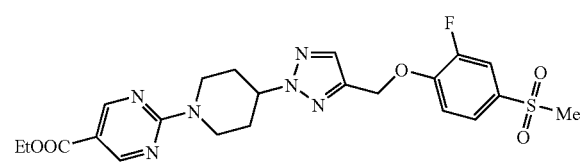

$^1$H NMR (CDCl₃): δ 8.86 (1H, s), 7.65-7.70 (3H, m), 7.24-7.28 (2H, m), 5.30 (2H, s), 4.90 (2H, m), 4.78 (1H, m), 4.35 (2H, q), 3.31 (2H, m), 2.32 (2H, m), 2.19 (2H, m), 1.38 (3H, t). LCMS: (ES⁺-MS found: 504.9).

Example 106

Ethyl 2-(4-(4-((2-fluoro-4-(1H-tetrazol-1-yl)phenoxy)methyl)-2H-1,2,3-triazol-2-yl)piperidin-1-yl)pyrimidine-5-carboxylate

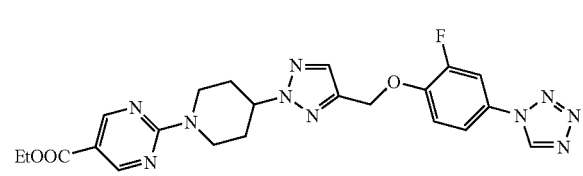

$^1$H NMR (CDCl₃): δ 8.91 (1H, s), 8.86 (2H, s), 7.72 (1H, s), 7.51 (1H, m), 7.41 (1H, m), 7.29 (1H, m), 5.30 (2H, s), 4.90 (2H, m), 4.79 (1H, m), 4.34 (2H, q), 3.32 (2H, m), 2.32 (2H, m), 2.19 (2H, m), 1.38 (3H, t). LCMS: (ES⁺-MS found: 495.0).

Example 107

5-Fluoro-2-(4-(4-((2-fluoro-4-(methylsulfonyl)phenoxy)methyl)-2H-1,2,3-triazol-2-yl)piperidin-1-yl)pyrimidine

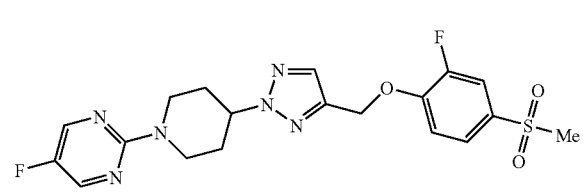

$^1$H NMR (CDCl₃): δ 8.22 (2H, s), 7.65-7.70 (3H, m), 7.24-7.28 (1H, m), 5.30 (2H, s), 4.72 (3H, m), 3.19 (2H, m), 3.04 (3H, s), 2.25 (2H, m), 2.16 (2H, m). LCMS: (ES⁺-MS found: 451.2).

The compounds in Examples 108-112 were synthesized from Intermediates 8 and the corresponding carboxylic acid in a manner similar to that described in Example 50. One skilled in the art of organic synthesis will appreciate that conditions such as solvent (DMF, CH₃CN), temperature, base (NEt₃, $^i$Pr₂NEt, K₂CO₃, NaHCO₃, Na₂CO₃, Cs₂CO₃) and concentration can be selected through routine experimentation to optimize yields. Additionally, alternative coupling methods can be used that are well known in the art of organic synthesis.

Example 108

(4-(4-((2-Fluoro-4-(1H-tetrazol-1-yl)phenoxy)methyl)-2H-1,2,3-triazol-2-yl)piperidin-1-yl)(pyridin-2-yl)methanone

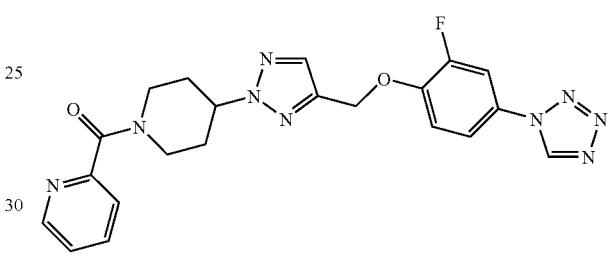

$^1$H NMR (DMSO-d₆): δ 10.00 (1H, s), 8.58 (1H, d), 7.94 (1H, s), 7.92 (1H, d), 7.89 (1H, m), 7.72 (1H, d), 7.61 (1H, m), 7.58 (1H, d), 7.46 (1H, m), 5.34 (2H, s), 4.87 (1H, m), 4.48 (1H, m), 3.73 (1H, m), 3.29 (1H, m), 3.12 (1H, m), 2.22 (1H, m), 2.06 (1H, m), 1.97 (2H, m). LCMS: (ES⁺-MS found: 450.2).

Example 109

(4-(4-((2-Fluoro-4-(1H-tetrazol-1-yl)phenoxy)methyl)-2H-1,2,3-triazol-2-yl)piperidin-1-yl)(6-hydroxypyridin-2-yl)methanone

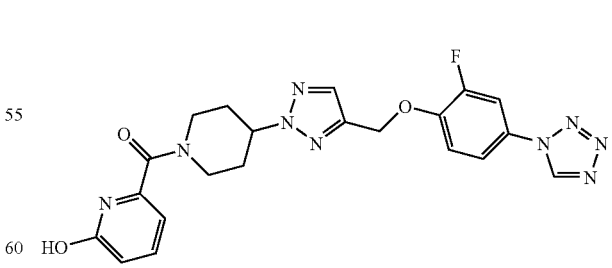

$^1$H NMR (DMSO-d₆): δ 10.00 (1H, s), 7.94 (1H, s), 7.90 (1H, m), 7.73 (1H, d), 7.59 (1H, m), 7.52 (1H, d), 6.45 (2H, m), 5.34 (2H, s), 4.86(2H, m), 4.37(1H, m), 3.62 (1H, m), 3.06 (1H, m), 1.99-2.19 (4H, m). LCMS: (ES⁺-MS found: 466.1).

Example 110

(4-(4-((2-Fluoro-4-(1H-tetrazol-1-yl)phenoxy)methyl)-2H-1,2,3-triazol-2-yl)piperidin-1-yl)(3-hydroxypyridin-2-yl)methanone

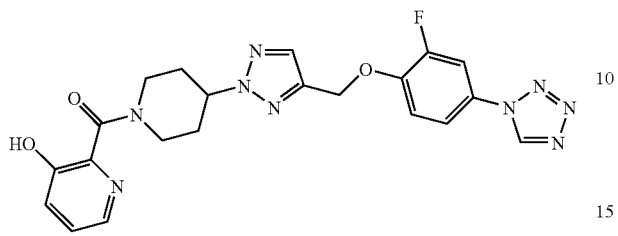

$^1$H NMR (DMSO-d$_6$): δ 10.39 (1H, br), 9.99 (1H, s), 8.03 (1H, d), 7.93 (1H, s), 7.91 (1H, m), 7.71 (1H, m), 7.59 (1H, d), 7.29 (2H, m), 5.34 (2H, s), 4.86 (1H, m), 4.49 (1H, m), 3.22 (1H, m), 3.07 (1H, m), 2.19 (1H, m), 1.93-2.04 (4H, m). LCMS: (ES$^+$-MS found: 466.2).

Example 111

(4-(4-((2-Fluoro-4-(1H-tetrazol-1-yl)phenoxy)methyl)-2H-1,2,3-triazol-2-yl)piperidin-1-yl)(3-methylpyridin-2-yl)methanone

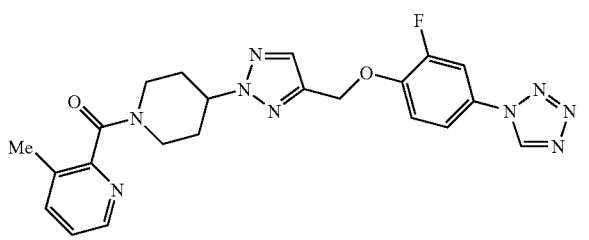

$^1$H NMR (DMSO-d$_6$): δ 10.00 (1H, s), 8.38 (1H, d), 7.94 (1H, s), 7.90 (1H, m), 7.72 (2H, m), 7.59 (1H, d), 7.34 (1H, m), 5.34 (2H, s), 4.87 (1H, m), 4.49 (1H, m), 3.22 (1H, m), 3.07 (1H, m), 2.23 (3H, s), 2.04 (1H, m), 1.93 (4H, m). LCMS: (ES$^+$-MS found: 464.4).

Example 112

(4-(4-((2-Fluoro-4-(1H-tetrazol-1-yl)phenoxy)methyl)-2H-1,2,3-triazol-2-yl)piperidin-1-yl)(pyridin-3-yl)methanone

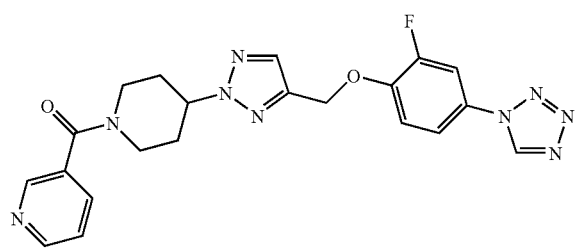

$^1$H NMR (DMSO-d$_6$): δ 10.00 (1H, s), 8.66 (2H, d), 7.94 (1H, s), 7.90 (2H, m), 7.72 (1H, m), 7.59 (1H, d), 7.34 (1H, m), 5.34 (2H, s), 4.86 (1H, m), 4.45 (1H, m), 3.59 (1H, m), 3.07 (1H, m), 1.99-2.35 (5H, m). LCMS: (ES$^+$-MS found: 450.0).

Example 113

5-Ethyl-2-(4-(3-((2-fluoro-4-(1H-tetrazol-1-yl)phenoxy)methyl)-1H-pyrazol-1-yl)piperidin-1-yl)pyrimidine

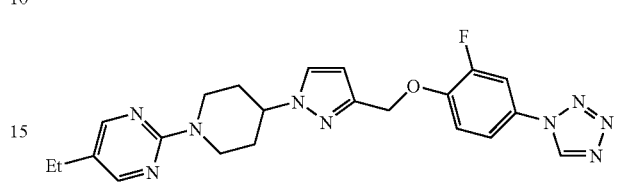

The title compound was synthesized using Intermediate 31 and 2-chloro-5-ethylpyrimidine in a similar manner as that described in Example 9.

$^1$H NMR (CDCl$_3$): δ 8.19 (2H, s), 7.41 (1H, m), 7.05 (1H, m), 6.77 (1H, m), 6.67 (1H, m), 6.35 (1H, s), 6.26 (1H, m), 5.09 (2H, m), 4.86 (2H, m), 4.37 (1H, m), 3.02 (2H, m), 2.47 (2H, m), 2.20 (2H, m), 1.95 (2H, m), 1.20 (3H, t).

Biological Example 1

Stimulation of cAMP

Generation of IC-GPCR2 Stable Cell Line

The compounds of the present invention were evaluated in an assay demonstrating agonism of IC-GPCR2. This assay was developed using a stable cell line expressing IC-GPCR-2, generated as follows. IC-GPCR2 (Seq. ID No. 1) was cloned into Gateway pDEST 40vector (Invitrogen), using the Gateway cloning system (invitrogen) according to the manufacturers instructions. A stable cell line was generated by transfecting a 10 cm plate of CHO cells (source) with 8 ug of this construct using Transit-CHO transfection kit (Mirus). CHO cells were plated the day prior to transfection at a density of 3,000,000 cells/plate. Clones were selected using the antibiotic G418 at 500 ug/ml. 23 clones were picked and assayed for the expression of the receptor by measuring changes in intracellular cAMP levels in response to an IC-GPCR2 agonist (Arena 51).

To measure cAMP activity in response to IC-GPCR2 agonist, the clones were plated in 96 well plates at 17500 cells per well. On the day after plating, cells were incubated with the IC-CPCR2 agonist at 10 uM for 30 minutes in Ham's F12 Media (Gibco) with 0.04% DMSO. cAMP was measured using the cAMP dynamic kit from Cis Bio (Bedford, Mass.) according to the manufacturers instructions. Briefly, cells were lysed, and cAMP levels determined by competitive immunoassay using D2 labeled cAMP, and europium cryptate tagged anti cAMP antibody. When in close proximity, the D2 and europium cryptate undergo fluorescence resonance energy transfer (FRET), which is measured as a fluorescence ratio (665 nm/620 nm). Unlabelled cAMP in the cell lysate competed with the D2 labeled cAMP for the europium cryptate labeled antibody. The resulting decrease in FRET signal corresponded to intracellular cAMP levels. Fluorescence was read on a BMG Labtech PHERAstar, software version 1.50.

The clone with the greatest response to IC-GPCR2 agonist was selected for the screening assay.

Determination of Activity of Compounds

Compounds were dissolved in 100% DMSO to a concentration of 10 uM to provide stock solutions. To determine activity against IC-GPCR2, compounds were incubated with IC-GPCR2 stably expressing cells (described above), at 6-8 concentrations ranging from 0.00003 to 10 micromolar, in 96 well plates, in 50 ul of Hams F12 media for 30 minutes. Cells were plated at 17500 cells per well 1 day before running the assay. All compounds were also screened against the parental CHO cells. cAMP was measured using the cAMP dynamic kit from Cis Bio (Bedford, Mass.), according to the manufacturer's instructions. Briefly, cells were lysed and cAMP levels determined by competitive immunoassay using D2 labeled cAMP, and europium cryptate tagged anti cAMP antibody. When in close proximity, the D2 and europium cryptate undergo fluorescence resonance energy transfer (FRET), which is measured as a fluorescence ratio (665 nm/620 nm). Unlabelled cAMP in the cell lysate competed with the D2 labeled cAMP for the europium cryptate labeled antibody. The resulting decrease in FRET signal corresponded to intracellular cAMP levels To determine percent activity for a tested compound, the FRET signal value obtained at a particular concentration are compared to the Maximal FRET signal value obtained for 5-Ethyl-2-{4-[4-(4-tetrazol-1-yl-phenoxymethyl)-thiazol-2-yl]-piperidin-1-yl}-pyrimidine. The maximal activity of 5-Ethyl-2-{4-[4-(4-tetrazol-1-yl-phenoxymethyl)-thiazol-2-yl]-piperidin-1-yl}-pyrimidine is designated as 100% activity. Typically, the concentration of 5-Ethyl-2-{4-[4-(4-tetrazol-1-yl-phenoxymethyl)-thiazol-2-yl]-piperidin-1-yl}-pyrimidine in the assay was approximately 0.1 μM. The synthesis of 5-Ethyl-2-{4-[4-(4-tetrazol-1-yl-phenoxymethyl)-thiazol-2-yl]-piperidin-1-yl}-pyrimidine is disclosed in co-owned pending U.S. patent application Ser. No. 11/964,461, herein incorporated by reference. Activities of compounds that were tested are shown in Table 1 below and are expressed as % activity at 3 μM compound compared to the maximal activity of 5-Ethyl-2-{4-[4-(4-tetrazol-1-yl-phenoxymethyl)-thiazol-2-yl]-piperidin-1-yl}-pyrimidine at 3 μM. Examples 39, 42, 43, 53, 79, and 97 were tested did not exhibit activity when tested at 3 μM but are contemplated to have activity at higher concentrations and therefore are not included in Table 1.

TABLE 1

| Example No. | % activity at 3 μM |
|---|---|
| 1 | 64.46 |
| 3 | 79.02 |
| 4 | 79.18 |
| 5 | 75.78 |
| 6 | 79.51 |
| 7 | 78.16 |
| 8 | 77.16 |
| 9 | 65.75 |
| 10 | 71.04 |
| 13 | 61.30 |
| 14 | 74.80 |
| 15 | 75.63 |
| 16 | 70.31 |
| 17 | 68.23 |
| 18 | 77.67 |
| 19 | 80.10 |
| 21 | 63.66 |
| 22 | 78.44 |
| 29 | 48.76 |
| 30 | 53.41 |
| 31 | 59.95 |
| 32 | 75.55 |
| 33 | 88.32 |
| 34 | 87.61 |
| 35 | 72.14 |
| 36 | 70.06 |
| 37 | 62.88 |
| 38 | 85.32 |
| 40 | 7.10 |
| 41 | 42.63 |
| 44 | 70.92 |
| 45 | 67.58 |
| 46 | 79.78 |
| 47 | 74.90 |
| 48 | 83.24 |
| 49 | 78.48 |
| 50 | 49.51 |
| 51 | 57.93 |
| 52 | 52.86 |
| 54 | 36.82 |
| 55 | 31.89 |
| 56 | 7.31 |
| 57 | 27.80 |
| 58 | 79.55 |
| 59 | 33.25 |
| 60 | 27.86 |
| 61 | 43.59 |
| 62 | 32.06 |
| 64 | 66.18 |
| 65 | 70.03 |
| 66 | 80.00 |
| 67 | 57.87 |
| 68 | 74.11 |
| 69 | 55.22 |
| 70 | 66.77 |
| 71 | 70.78 |
| 72 | 60.55 |
| 73 | 84.07 |
| 74 | 61.88 |
| 75 | 47.94 |
| 76 | 56.39 |
| 77 | 69.86 |
| 78 | 57.13 |
| 80 | 77.53 |
| 81 | 32.98 |
| 82 | 64.90 |
| 83 | 63.14 |
| 84 | 78.05 |
| 85 | 76.12 |
| 86 | 71.39 |
| 87 | 75.63 |
| 88 | 60.96 |
| 89 | 48.60 |
| 90 | 13.60 |
| 91 | 5.82 |
| 92 | 58.28 |
| 93 | 50.84 |
| 94 | 49.73 |
| 95 | 51.03 |
| 96 | 28.90 |
| 98 | 17.16 |
| 99 | 56.81 |
| 100 | 10.69 |
| 101 | 50.67 |
| 102 | 38.98 |
| 103 | 51.30 |
| 104 | 28.40 |
| 105 | 10.65 |
| 106 | 11.46 |
| 107 | 36.83 |
| 108 | 41.78 |
| 109 | 7.45 |
| 110 | 1.30 |
| 111 | 24.12 |
| 112 | 42.30 |
| 113 | 57.71 |

Biological Example 2

Insulin Secretion (Islet Perifusion)

To determine the effect of IC-GPCR2 agonists on insulin secretion from islets, islets from Sprague Dawley rats are isolated. 200-250 g Sprague Dawley rats (Charles River laboratories) are maintained on regular chow (Purina 5001). Before the procedure rats are anesthetized with intra peritoneal injection of pentobarbital at 200 mg/kg. The bile duct is clamped where it enters the duodenum, then a catheter is placed in the bile duct between the liver and the pancreas. The pancreas is infused through the catheter with a solution of 0.75 mg/ml collagenase P (Roche) in HBSS buffer (Biowhitaker) supplemented with 0.1% glucose and 0.02% BSA. The pancreas is then excised from the rat and placed in 5 ml of the collagenase P solution in a 37° C. waterbath for 8 minutes. After 8 minutes the digested pancreas is shaken vigorously by hand for 30 seconds. The resulting digest is washed four times in the HBSS buffer, then applied to a discontinuous ficoll gradient. To make the gradient, the digest is resuspended in 7.5 ml of ficoll DL400 solution (Sigma) density 1.108, in a 15 ml tube. Three 2 ml layers of ficoll solution of decreasing density (1.096, 1.069, 1.037) are then added to the tube to create a density gradient. The gradient is centrifuged at 1500 rpm for 15 minutes after which islets are picked from the top two layers. Islets are washed four times in HBSS buffer, then cultured in RPMI 1640 media (Gibco) supplemented with 1% fetal bovine serum. The following day, 25 size-matched islets are placed in a perifusion chamber and exposed to Krebs Ringer Buffer (KRB; 119 mM NaCl, 4.7 mM KCl, 25 mM $NaHCO_3$, 2.5 mM $CaCl_2$, 1.2 mM $MgSO_4$, 1.2 mM $KH2PO_4$) at a rate of 1 ml/minute, using a Cellex Acu-sys S perifusion culture system. The islets are exposed to KRB containing glucose at 2 mM for 30 minutes, followed with buffer containing 16 mM glucose for 30 minutes, then returned to 2 mM glucose for a further 30 minutes, in the presence of 0.1-100 uM of the IC-GPCR2 agonist or vehicle (DMSO). Perifusate is collected at 1 minute intervals using a fraction collector, and assayed for insulin using an ELISA kit (Mercodia Ultrasensitive Rat Insulin ELISA Kit, ALPCO). Insulin secretion rate in response to glucose is plotted against time, and the AUC of the curve determined in order to quantify the insulin secretory response to 16 mM glucose during the 30 minute perifusion. Statistical significance of differences in AUC between treated and untreated islets are determined by paired Students t test.

Biological Example 3

Oral Glucose Tolerance 8-10 week old male C57/6J mice (Harlan) were maintained on regular chow diet (Purina 5001). The day of the experiment mice were fasted for 6 hours, then randomized into groups (n=8) to receive the tested IC-GPCR2 agonist at doses ranging from 0.3-30 mg/kg or the vehicle (1% CMC, 2% TWEEN 80). Compounds were delivered orally via gavage at 10 ml/kg. Blood glucose levels were measured by glucometer (Ascensia Elite XL, Bayer) at time 0, before administration of compound. Blood glucose was measured again after 30 minutes, and then the mice were dosed orally with 2 g/kg glucose at 10 ml/kg. Blood glucose measurements were taken 15, 30, 60, 90 and 120 minutes after glucose administration, by glucometer (Ascensia Elite XL, Bayer).

Glucose levels were plotted against time, and the incremental area under the curve (AUC) of the glucose excursion was determined from time 0 using Graphpad Prism 5.0. Outliers were excluded using Tukey's box plot outlier test, and statistical significance of differences in AUC of compound treatment compared to vehicle was determined by non-parametric Kruskal-Wallis test with Dunn's post test.

Table 2 below shows the mean percentage inhibition of the glucose excursion for the eight animals tested in each group. The compounds were tested at 30 mg/kg and the levels of blood glucose were determined in the presence and absence of the tested compounds. The percent of glucose reduction is reported. The tested compounds were selected as examples from the exemplified compounds. These results demonstrate that the IC-GPCR2 agonists can lower blood glucose in response to an oral glucose challenge.

TABLE 2

| Compound | % reduction AUC glucose excursion at 30 mg/kg |
|---|---|
| Compound 1 | 40.8 |
| Compound 1 | 58.8 |

Biological Example 4

Tissue Specific Expression

RNA was extracted from isolated rat and mouse islets, and used to prepare double stranded cDNA using standard techniques (see Sambrook et al., Molecular Cloning, A Laboratory Manual (3rd ed. 2001); Current Protocols in Molecular Biology (Ausubel et al., eds., 1994)). The cDNA was cloned into the pZL1 vector (Invitrogen) and the 3' ends of individual clones were sequenced in multiple rounds of sequencing reactions. Sequence data representing approximately 12,000 independent clones were used to construct oligonucleotide probes synthesized on a GENECHIP® (Affymetrix Inc., Santa Clara, Calif.), producing mouse and rat islet chips. RNA from five rat islet preparations (each preparation from a different mouse), and preparations from a panel of rat tissues, were hybridized to the rat chips. Expression data was analyzed with the Affymetrix MAS 4.0 algorithm to give relative gene expression values as average difference scores, and presence/absence calls. RNA from two preparations from a mouse beta cell line BHC-9, four mouse islet preparations (each preparation from a different mouse), and preparations from a panel of mouse tissues, were hybridized to the mouse chips. Expression data was analyzed with the Affymetrix MAS 5.0 algorithm to give relative gene expression values as signal, and presence/absence calls.

FIGS. 1 (rat) and 2 (mouse) show the tissue specific expression of the receptor for the novel agonists of the present invention, showing tissue specificity to pancreatic islet cells (including the beta cells therein).

Sequence ID No. 1
atggaatcatctttctcatttggagtgatccttgctgtcctggcctccctcatcattgct actaacacactagtggctgtggctgtgctgctgttgatccacaagaatgatggtgtcagt

```
-continued
ctctgcttcaccttgaatctggctgtggctgacaccttgattggtgtggccatctctggc ctactcacagaccagctctccagcccttctcggcccacacagaagaccctgtgcagcctg cggatggcatttgtcacttcctccgcagctgcctctgtcctcacggtcatgctgatcacc tttgacaggtaccttgccatcaagcagcccttccgctacttgaagatcatgagtgggttc gtggccggggcctgcattgccgggctgtggttagtgtcttacctcattggcttcctccca ctcggaatccccatgttccagcagactgcctacaaagggcagtgcagcttctttgctgta tttcaccctcacttcgtgctgaccctctcctgcgttggcttcttcccagccatgctcctc tttgtcttcttctactgcgacatgctcaagattgcctccatgcacagccagcagattcga aagatggaacatgcaggagccatggctggaggttatcgatccccacggactcccagcgac ttcaaagctctccgtactgtgtctgttctcattgggagctttgctctatcctggaccccc ttccttatcactggcattgtgcaggtggcctgccaggagtgtcacctctacctagtgctg gaacggtacctgtggctgctcggcgtgggcaactccctgctcaacccactcatctatgcc tattggcagaaggaggtgcgactgcagctctaccacatggccctaggagtgaagaaggtg ctcacctcattcctcctctttctcttggccaggaattgtgcccagagaggcccagggaa agttcctgtcacatcgtcactatctccagctcagagtttgatggctaa Sequence ID No. 2
MESSFSFGVILAVLASLIIATNTLVAVAVLLLIHKNDGVSLCFTLNLAVADTLIGVAISG

LLTDQLSSPSRPTQKTLCSLRMAFVTSSAAASVLTVMLITFDRYLAIKQPFRYLKIMSGF

VAGACIAGLWLVSYLIGFLPLGIPMFQQTAYKGQCSFFAVFHPHFVLTLSCVGFFPAMLL

FVFFYCDMLKIASMHSQQIRKMEHAGAMAGGYRSPRTPSDFKALRTVSVLIGSFALSWTP

FLITGIVQVACQECHLYLVLERYLWLLGVGNSLLNPLIYAYWQKEVRLQLYHMALGVKKV

LTSFLLFLLARNCGPERPRESSCHIVTISSSEFDG
```

Biological Example 5

Incretin Measurement

The effect of IC-GPCR2 agonists on the secretion of insulin, Glucagon-like peptide-1 (GLP-1) and GIP in C57/6J mice are determined as follows.

8-10 week old male C57/6J mice (Harlan) are maintained on a regular chow diet (Purina 5001). On the day of the experiment mice are fasted for 6 hours then randomized into groups (n=8). All groups are treated with the DPPIV inhibitor sitagliptin at 100 mg/kg to prevent degradation of active GLP-1. IC-GPCR-2 agonist compounds are dosed at concentrations ranging from 0.3-300 mg/kg in 1% CMC, 2% TWEEN 80 at −30 minutes. Sitagliptin is administered in the same dosing solution. Oral glucose at 2 g/kg is administered at 0 minutes. At 10 minutes after glucose administration, animals are anesthetized with pentobarbital (40 mg/ml in 10% ethanol) and blood collected by heart puncture in microtainer tubes (BD) with potassium EDTA. For GLP-1 assay, the collection tubes also contain a DPP-IV inhibitor provided in the GLP-1 assay kit.

Insulin is measured using the Mercodia mouse Insulin ELISA Kit (ALPCO) according to the manufacturer's instructions. Bioactive GLP-1 is measured using Glucagon-like peptide-1 (active) ELISA assay kit (Linco) according to the manufacturers instructions. GIP is measured using rat/mouse GIP total ELISA assay kit (Linco), according to the manufacturer's instructions.

Biological Example 6

Improvement of Diabetes Parameters in Female ZDF Rat

Female ZDF rats (Charles River laboratories) are obtained at 6 weeks of age and acclimatized for 1 week before being placed on a high fat diet (RD 13004, Research Diets). Compounds are administered to the rats by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer), insulin is measured using rat insulin ELISA kit (ALPCO). Insulin and glucose levels are compared to those of vehicle treated animals to determine efficacy.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound of Formula (I):

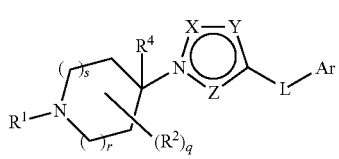

wherein,
X, Y and Z are each independently selected from the group consisting of N and $C(R^3)$;
the subscript r is 0, 1, 2 or 3;
the subscript s is 0, 1, 2 or 3, and the sum of r+s is $\leq 4$;
the subscript q is 0, 1, 2, 3 or 4;
L is $-(CH_2)_n-$ wherein the subscript n is 2, 3 or 4, and optionally at least one $CH_2$ is replaced by O, $NR^5$, S, S(O) or $S(O)_2$, and any remaining $CH_2$ is optionally substituted with one or two substituents selected from the group consisting of halo, $C_{1-4}$alkyl, $C_{3-6}$cycloalkyl and $C_{1-4}$haloalkyl;

Ar is an aryl or heteroaryl group, optionally substituted with one, two, three, four or five $R^6$ substituents; wherein the heteroaryl is selected from the group consisting of pyridyl, furanyl, thienyl, thiazolyl, isothiazolyl, triazolyl, imidazolyl, isoxazolyl, pyrrolyl, pyrazolyl, pyridazinyl, pyrazinyl, and pyrimidinyl; and when n is 2, the aryl is substituted with one, two, three, four or five $R^6$ substituents;

$R^1$ is selected from the group consisting of H, $C_{1-10}$alkyl, $C_{1-10}$substituted alkyl, $C_{3-7}$cycloalkyl, $C_{3-7}$subsituted cycloalkyl, $C_{2-10}$alkenyl, $C_{2-10}$alkynyl, $-X^1-C(O)R^a$, $-X^1-C(O)OR^a$, $-X^1-C(O)NR^aR^b$, $-S(O)_2R^a$, 4- to 7-membered heterocyclyl group, aryl and a 5- to 10-membered heteroaryl group, wherein each of said cycloalkyl group, heterocyclyl group, aryl group and heteroaryl group is optionally substituted with from one, two, three or four substituents independently selected from the group consisting of halo, $C_{1-10}$alkyl, $C_{1-10}$substituted alkyl, $C_{3-7}$cycloalkyl, $C_{2-10}$alkenyl, $C_{2-10}$alkynyl, aryl, heteroaryl, $-CN$, $-NR^aC(O)R^b$, $-NR^aC(O)NR^aR^b$, $-NO_2$, $-OR^a$, $-NR^aR^b$, $-C(O)R^a$, $-C(O)OR^a$, $-C(O)NR^aR^b$, $-SR^a$, $-S(O)R^a$, $-S(O)_2R^a$, $-NR^aS(O)_2R^b$, and $-S(O)_2NR^aR^b$, or optionally $R^a$ and $R^b$ are combined to form a 4-, 5- or 6- membered ring, and $X^1$ is selected from the group consisting of a bond, $C_{1-4}$alkylene, $C_{2-6}$alkenylene, $C_{2-6}$alkynylene, $-C(O)-$, and $-C(O)(CH_2)_{1-4}-$, wherein the aliphatic portions of $X^1$ are optionally substituted with one, two or three groups selected from the group consisting of halo, $C_{1-4}$alkyl, and $C_{1-4}$substituted alkyl;

each $R^2$ is independently selected from the group consisting of halo, $C_{1-5}$ alkyl, $C_{1-5}$substituted alkyl, $C_{3-7}$cycloalkyl, $C_{3-7}$substituted cycloalkyl, —C(O)$R^a$, —C(O)O$R^a$, —C(O)N$R^aR^b$, —O$R^a$, —N$R^aR^b$, —N$R^a$C(O)$R^b$, —S(O)$R^a$, —S(O)$_2R^a$ and —S(O)$_2$N$R^aR^b$, and wherein when the subscript q is 2, 3, or 4, two $R^2$ groups can optionally cyclize to form a ring;

each $R^3$ is independently selected from the group consisting of H, halo, $C_{1-4}$ alkyl, $C_{1-4}$ haloalkyl, $C_{3-7}$ cycloalkyl, aryl and —O$R^a$; provided that when L-Ar is —O—CH$_2$—Ar, $R^3$ is independently selected from the group consisting of H, halo, $C_{1-4}$ alkyl, $C_{1-4}$ haloalkyl, $C_{3-7}$ cycloalkyl, and —O$R^a$;

$R^4$ is selected from the group consisting of H, halo, $C_{1-6}$ alkyl, and $C_{1-6}$substituted alkyl;

$R^5$ is selected from the group consisting of H, $C_{1-4}$alkyl, $C_{1-4}$haloalkyl, $C_{3-6}$cycloalkyl, —C(O)$R^a$ and —S(O)$_2R^a$;

each $R^6$ is independently selected from the group consisting of H, halo, $C_{1-10}$alkyl, $C_{1-10}$ substituted alkyl, $C_{3-7}$cycloalkyl, $C_{3-7}$cycloalkyl, $C_{2-10}$alkenyl, $C_{2-10}$alkynyl, —CN, —NO$_2$, —O$R^a$, —N$R^aR^b$, —C(O)$R^a$, —C(O)O$R^a$, —C(O)N$R^aR^b$, —N$R^a$C(O)$R^b$, —N$R^a$C(O)O$R^b$, —N$R^a$C(O)N$R^aR^b$, —S$R^a$, —S(O)$R^a$, S(O)$_2R^a$, —N$R^a$S$R^b$, —N$R^a$S(O)$R^b$, —N$R^a$S(O)$_2R^b$, —S(O)$_2$N$R^aR^b$, a 4- to 7-membered heterocyclyl group, aryl and a 5- to 10-membered heteroaryl group, wherein each of said heterocyclyl groups, said aryl and heteroaryl groups are optionally substituted with from one to four substituents independently selected from halo, oxo, $C_{1-4}$alkyl, $C_{1-4}$ haloalkyl, $C_{3-7}$cycloalkyl, —CN, —NO$_2$, —O$R^a$, —N$R^aR^b$, —C(O)$R^a$, —C(O)O$R^a$, —C(O)N$R^aR^b$, —N$R^a$C(O)$R^b$, —N$R^a$C(O)O$R^b$, —N$R^a$C(O)N$R^aR^b$, —S$R^a$, —S(O)$R^a$, —S(O)$_2R^a$, —N$R^a$S(O)$R^b$, —N$R^a$S(O)$_2R^b$ and —S(O)$_2$N$R^aR^b$ or optionally $R^a$ and $R^b$ are combined to form a 4-, 5- or 6-membered ring;

and each $R^a$ and $R^b$ is independently selected from the group consisting of H, $C_{1-10}$ alkyl, $C_{1-10}$haloalkyl, $C_{3-10}$cycloalkyl, heterocyclyl, $C_{2-10}$alkenyl, $C_{2-10}$alkynyl, aryl, 5- to 6-membered heteroaryl and aryl$C_{1-4}$ alkyl; and wherein the aliphatic portions of each of said $R^a$ and $R^b$ is optionally substituted with from one to three groups selected from the group consisting of halo, —O$R''$, —OC(O)$R''$, —OC(O)N($R''$)$_2$, —S$R''$, —S(O)$R''$, —S(O)$_2R^2$, —S(O)$_2$N($R''$)$_2$, —N$R''$S(O)$_2R''$, —C(O)N($R''$)$_2$, —C(O)$R''$, —N$R''$C(O)$R''$, —N$R''$C(O)N($R''$)$_2$, —C(O)O$R''$, —N$R''$C(O)O$R''$, —CN, —NO$_2$, —N($R''$)$_2$ and —N$R''$S(O)$_2$N($R''$)$_2$, wherein each $R''$ is independently H, $C_{1-3}$haloalkyl or an unsubstituted $C_{1-6}$ alkyl; and wherein the aryl and heteroaryl portions are optionally substituted with from one to three groups selected from halo, —O$R'''$, —OC(O)N($R'''$)$_2$, —S$R'''$, —S(O)$R'''$, —S(O)$_2R'''$, —S(O)$_2$N($R'''$)$_2$, —N$R'''$S(O)$_2R'''$, —C(O)N($R'''$)$_2$, —C(O)$R'''$, —N$R'''$C(O)$R'''$, —N$R'''$C(O)N($R'''$)$_2$, —C(O)O$R'''$, —N$R'''$C(O)O$R'''$, —CN, —NO$_2$, —N($R'''$)$_2$ and —N$R'''$S(O)$_2$N($R'''$)$_2$, wherein each $R'''$ is independently H, $C_{1-3}$haloalkyl or an unsubstituted $C_{1-6}$ alkyl;

or a pharmaceutically acceptable salt, solvate, stereoisomer, and/or ester thereof.

2. The compound of claim 1, wherein the ring having X, Y and Z is selected from the group consisting of

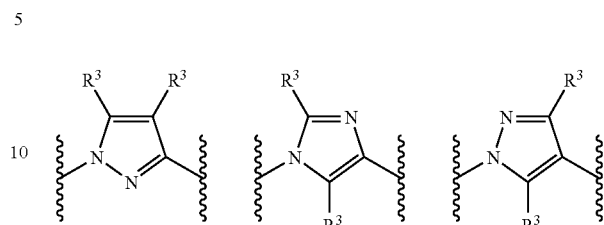

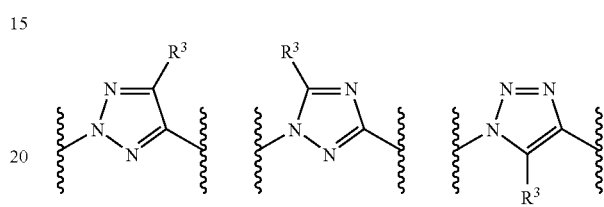

3. The compound of claim 2, wherein the ring having X, Y and Z is selected from the group consisting of

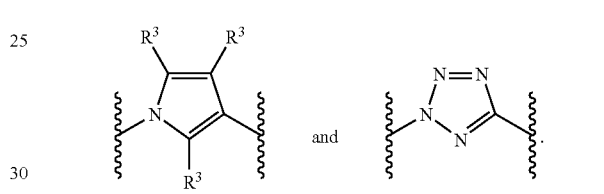

4. The compound of claim 1, wherein each $R^6$ is independently selected from the group consisting of H, halo, —N$R^aR^b$, —N$R^a$C(O)$R^b$, —S(O)$R^a$, —S(O)$_2R^a$, $C_{1-3}$alkyl, $C_{1-3}$haloalkyl, substituted heteroaryl and unsubstituted heteroaryl.

5. The compound of claim 4 wherein each $R^6$ is independently selected from the group consisting of H, fluoro, chloro, methyl, ethyl, —CF$_3$, imidazolyl, pyrazolyl, triazolyl, tetrazolyl, —S(O)$R^a$, and —S(O)$_2R^a$.

6. The compound of claim 1, wherein Ar is a six-membered aryl optionally substituted with from 1 to 3 $R^6$ substituents or a heteroaryl, optionally substituted with from 1 to 3 $R^6$ substituents.

7. The compound of claim 6, wherein Ar is selected from the group consisting of optionally substituted six-membered aryl, optionally substituted pyridyl, optionally substituted pyrimidinyl, optionally substituted pyrazinyl, and optionally substituted pyridazinyl.

8. The compound of claim 1, wherein the subscript n is 2.

9. The compound of claim 1, wherein $R^1$ is selected from the group consisting of —$X^1$—C(O)$R^a$, —$X^1$—C(O)O$R^a$, optionally substituted aryl group and optionally substituted heteroaryl group.

10. The compound of claim 9, wherein $R^1$ is —C(O)O$R^a$, pyrimidine optionally substituted with from one to two substituents independently selected from the group consisting of halo, $C_{3-6}$cycloalkyl, $C_{1-10}$alkyl, and $C_{1-10}$substituted alkyl, or oxadiazole.

* * * * *